US008901082B2

(12) United States Patent
Okano et al.

(10) Patent No.: US 8,901,082 B2
(45) Date of Patent: Dec. 2, 2014

(54) IMMUNITY-INDUCING AGENT AND METHOD FOR DETECTION OF CANCER

(75) Inventors: Fumiyoshi Okano, Kanagawa (JP); Masaki Shimizu, Ehime (JP); Takanori Saito, Kanagawa (JP)

(73) Assignee: Toray Industries, Inc., Tokyo (JP)

(*) Notice: Subject to any disclaimer, the term of this patent is extended or adjusted under 35 U.S.C. 154(b) by 163 days.

(21) Appl. No.: 13/002,629

(22) PCT Filed: Jul. 10, 2009

(86) PCT No.: PCT/JP2009/062574
§ 371 (c)(1),
(2), (4) Date: Feb. 16, 2011

(87) PCT Pub. No.: WO2010/005069
PCT Pub. Date: Jan. 14, 2010

(65) Prior Publication Data
US 2011/0130343 A1    Jun. 2, 2011

(30) Foreign Application Priority Data

Jul. 10, 2008  (JP) ................................. 2008-180548

(51) Int. Cl.
| A61K 38/08 | (2006.01) |
| A61K 38/00 | (2006.01) |
| C07K 7/06 | (2006.01) |
| C07K 14/00 | (2006.01) |
| A61P 35/00 | (2006.01) |
| C07K 14/47 | (2006.01) |
| A61K 31/711 | (2006.01) |
| A61K 39/00 | (2006.01) |
| G01N 33/574 | (2006.01) |

(52) U.S. Cl.
CPC ............... *C07K 14/47* (2013.01); *A61K 31/711* (2013.01); *A61K 39/0011* (2013.01); *G01N 33/57415* (2013.01); *G01N 33/57426* (2013.01); *A61K 38/00* (2013.01); *A61K 2039/55566* (2013.01)
USPC ........... 514/19.3; 530/327; 530/328; 530/350

(58) Field of Classification Search
CPC . A61K 31/711; A61K 38/00; A61K 39/0011; A61K 2039/55566; G01N 33/57426; G01N 33/57415; C07K 14/47
See application file for complete search history.

(56) References Cited

U.S. PATENT DOCUMENTS 5,595,756 A * 1/1997 Bally et al. ..................... 424/450

FOREIGN PATENT DOCUMENTS

| EP | 0419858 A1 | 4/1991 |
| JP | 2006-014637 | 1/2006 |
| WO | WO 0177332 A2 * | 10/2001 | ............. C12N 15/12 |
| WO | WO 03060080 A2 * | 7/2003 | |
| WO | WO-2004024750 A2 | 3/2004 | |
| WO | WO-2004048938 A2 | 6/2004 | |
| WO | WO-2005/083074 | 9/2005 | |
| WO | WO-2008/034076 | 3/2008 | |
| WO | WO 2008141197 A1 * | 11/2008 | ............. C07K 16/00 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. Biol (2002) 324, 373-386.*
Merck manual, Introduction, p. 1, Accessed Mar. 5, 2008.*
Merck manual, Clinical Aspects of Cancer, pp. 1-4, Accessed Mar. 5, 2008.*
Auerbach. R. et al, Angiogenesis assays: Problems and pitfalls, Cancer and Metastasis Reviews, 2000, 19, pp. 167-172.*
Gura, T. Systems for Identifying New Drugs Are Often Faulty, Science, 1997, 278, pp. 1041-1042.*
Jain R. K., Barriers to Drug Delivery in Solid Tumors, Scientific American, 1994, pp. 58-65.*
Zhu et al, Toll like receptor-3 ligand poly-ICLC promotes the efficacy of peripheral vaccinations with tumor antigen-derived peptide epitopes in murine CNS tumor models, Journal of Translational Medicine, 2007, 5, pp. 1-15.*

(Continued)

Primary Examiner — Julie Ha
Assistant Examiner — Li Ni Komatsu
(74) Attorney, Agent, or Firm — Wilmer Cutler Pickering Hale and Dorr LLP

(57) ABSTRACT

An immunity-inducing agent comprising as an effective ingredient(s) at least one polypeptide selected from the following polypeptides, the polypeptide(s) having an immunity-inducing activity/activities, or as an effective ingredient(s) a recombinant vector(s) which comprise(s) a polynucleotide(s) encoding the polypeptide(s) and is/are capable of expressing the polypeptide(s) in vivo can be used for therapy and/or prophylaxis of cancer: (a) a polypeptide consisting essentially of not less than 7 consecutive amino acids in any one of the amino acid sequences shown in the odd number IDs of SEQ ID NOs:3 to 95 in SEQUENCE LISTING; (b) a polypeptide having a sequence identity of not less than 90% with the polypeptide (a) and consisting essentially of not less than 7 amino acids; and (c) a polypeptide comprising the polypeptide (a) or (b) as a partial sequence thereof. Further, since the above polypeptide(s) react(s) with antibodies existing specifically in serum of a cancer patient, it is possible to detect cancer in a living body by measuring the antibodies in a sample.

7 Claims, 3 Drawing Sheets

(56) References Cited

OTHER PUBLICATIONS

Hollis et al, Immunoglobulin lamda light-chain-related genes 14.1 and 16.1 are expressed in pre-B cells and may encode the human immunoglobulin w light-chain protein, Proc. Natl. Acad. Sci. USA, 1989, 86, pp. 5552-5556.*

Cooper et al, Production of Antibodies, Current Protocols in Immunology, 1995, 2.4.1-2.4.9.*

Defination of prophylaxis, from http://dictionary.reference.com/browse/prophylaxis, pp. 1-3, accessed Aug. 9, 2012.*

Sporn, B and Suh, N, Chemoprevention of cancer, Carcinogenesis, 2000, 21, pp. 525-530.*

Cancer Drug Design and Discovery. Neidle, Stephen, ed., Elsevier/Academic Press, 2008, p. 427-431.*

Cellular and Molecular Basis of Cancer from Merck Manual, 2008, pp. 1-5, accessed Nov. 7, 2012.*

PubMed publication on amino acid mutation in protein in 2009, from http://www.ncbi.nlm.nih.gov/pubmed?term=((protein)%20AND%20amino%20acid%20m . . . , pages 1-3, accessed Jul. 12, 2013.*

Schirle et al, Combining computer algorithms with experimental approaches permits the rapid and accurate identification of T cell epitopes from defined antigens, Journal of Immunological Methods, 2001, 257, pp. 1-16.*

Mufson, Tumor antigen targets and tumor immunotherapy, Frontiers in Bioscience, 2006, 11, pp. 337-343.*

Human CD179b amino acid sequence-P15814, from http://www.uniprot.org/uniprot/P15814, pp. 1-9, accessed Dec. 1, 2013.*

Kiyokawa et al., "Diagnostic importance of CD179a/b as markers of precursor B-cell lymphoblastic lymphoma," Mod Pathol, vol. 17, pp. 423-429 (2004).

International Search Report mailed on Aug. 25, 2009 for International Patent Application No. PCT/JP2009/062574.

European Search Report for European Patent Application No. 09794513.3 mailed Oct. 9, 2012. 8 pages.

Oka, et al., "Induction of WT1 (Wilms' tumor gene)—Specific Cytotoxic T Lymphocytes by WT1 Peptide Vaccine and the Resultant Cancer Regression", PNAS, 101(38):13885-13890, Sep. 21, 2004, 6 pages.

* cited by examiner

IMMUNITY-INDUCING AGENT AND METHOD FOR DETECTION OF CANCER

This application is a U.S. National Phase Application under 35 U.S.C. 371 of International Patent Application No. PCT/JP2009/062574 filed Jul. 10, 2009, which claims priority to Japanese Application Serial No. 2008-180548 filed on Jul. 10, 2008, the contents of which are hereby incorporated by reference in their entireties.

TECHNICAL FIELD

The present invention relates to a novel immunity-inducing agent useful as a therapeutic and/or prophylactic agent for cancer. Further, the present invention relates to a novel method for detection of cancer.

BACKGROUND ART

Cancer is the commonest cause for death among all of the causes for death, and therapies carried out therefor at present are mainly surgical treatment in combination with radiotherapy and chemotherapy. In spite of the developments of new surgical methods and discovery of new anti-cancer agents in recent years, treatment results of cancers are not improved very much at present except for some cancers. In recent years, by virtue of the development in molecular biology and cancer immunology, cancer antigens recognized by cytotoxic T cells reactive with cancers, as well as the genes encoding the cancer antigens, were identified, and expectations for antigen-specific immunotherapies have been raised (Non-patent Literature 1).

In immunotherapy, to reduce side effects, it is necessary that the peptide, polypeptide or protein recognized as the antigen exist hardly in normal cells and exist specifically in cancer cells. In 1991, Boon et al. of Ludwig Institute in Belgium isolated a human melanoma antigen MAGE 1, which is recognized by CD8-positive T cells, by a cDNA-expression cloning method using an autologous cancer cell line and cancer-reactive T cells (Non-patent Literature 2). Thereafter, the SEREX (serological identifications of antigens by recombinant expression cloning) method, wherein tumor antigens recognized by antibodies produced in the living body of a cancer patient in response to the cancer of the patient himself are identified by application of a gene expression cloning method, was reported (Non-patent Literature 3; Patent Literature 1), and several cancer antigens have been isolated by this method (Non-patent Literatures 4 to 9). Using a part thereof as targets, clinical tests for cancer immunotherapy have started.

On the other hand, as in human, a number of tumors such as mammary gland cancer, leukemia and lymphoma are known in dogs and cats, and they rank high also in the statistics of diseases in dogs and cats. However, at present, no therapeutic agent and prophylactic agent exist which are effective for cancers in dogs and cats. Most of tumors in dogs and cats are realized by owners only after they advanced to grow bigger, and in many cases, it is already too late to visit a hospital to receive surgical excision of the tumor or administration of a human drug (an anticancer preparation or the like), so that those dogs and cats often die shortly after the treatment. Under such circumstances, if therapeutic agents and prophylactic agents for cancer effective for dogs and cats become available, their uses for canine cancers are expected to be developed.

Since early detection of cancer leads to good treatment results, a method for detecting cancer which can be easily carried out by testing serum, urine or the like without physical and economical burden to cancer patients is demanded. Recently, methods wherein tumor products such as tumor markers are measured have been widely used as diagnostic methods using blood or urine. Examples of the tumor products include tumor-related antigens, enzymes, specific proteins, metabolites, tumor genes, products of tumor genes, and tumor-suppressor genes, and, in some cancers, a carcinoembryonic antigen CEA, glycoproteins CA19-9 and CA125, a prostate-specific antigen PSA, calcitonin which is a peptide hormone produced in thyroid, and the like are utilized as tumor markers in cancer diagnosis (Non-patent Literature 10). However, in most types of cancers, there are no tumor markers useful for cancer diagnosis. Further, since most of the tumor markers currently known exist only in very small amounts (e.g., in the order of pg/mL) in body fluid, their detection requires a highly sensitive measurement method or a special technique. Under such circumstances, if a novel cancer detection method by which various cancers can be detected by simple operations is provided, its use for diagnosis of various cancers are expected to be developed.

CD179b is known to be a part of the surrogate light chain of immunoglobulin and to be expressed on the membrane surfaces of precursor cells of B cells (pre-B cells and pro-B cells). It disappears upon differentiation of B cells and is not expressed in mature B cells. However, CD179b is known to be expressed in leukemia (pre-B cell leukemia) cells produced by cancerization of pre-B cells (Non-patent Literatures 10 and 11). Further, CD179b is known to be expressed also in lymphoma (pre-B cell lymphoma) cells produced by cancerization of pre-B cells, and able to be used as a diagnostic marker for pre-B cell lymphoma (Non-patent Literature 12). However, its specific expression has not been reported for leukemia cells other than pre-B cell leukemia cells, lymphomas other than pre-B cell lymphoma, breast cancer cells and the like. Further, there has been no report suggesting that enhancement of immunity against CD179b is useful for therapy and/or prophylaxis of cancer.

PRIOR ART LITERATURES

Patent Literature

Patent Literature 1: U.S. Pat. No. 5,698,396 B

Non-Patent Literatures

Non-patent Literature 1: Tsuyoshi Akiyoshi, "Cancer and Chemotherapy", 1997, Vol. 24, pp. 551-519
Non-patent Literature 2: Bruggen P. et al., Science, 254:1643-1647 (1991)
Non-patent Literature 3: Proc. Natl. Acad. Sci. USA, 92:11810-11813 (1995)
Non-patent Literature 4: Int. J. Cancer, 72:965-971 (1997)
Non-patent Literature 5: Cancer Res., 58:1034-1041 (1998)
Non-patent Literature 6: Int. J. Cancer, 29:652-658 (1998)
Non-patent Literature 7: Int. J. Oncol., 14:703-708 (1999)
Non-patent Literature 8: Cancer Res., 56:4766-4772 (1996)
Non-patent Literature 9: Hum. Mol. Genet. 6:33-39 (1997)
Non-patent Literature 10: Adv. Immunol., 63:1-41 (1996)
Non-patent Literature 11: Blood, 92:4317-4324 (1998)
Non-patent Literature 12: Modern Pathology, 17:423-429 (2004)

DISCLOSURE OF THE INVENTION

Problems to be Solved by the Invention

The present invention aims to discover a novel polypeptide useful as an agent for therapy and/or prophylaxis and/or the like of cancer, thereby providing use of the polypeptide for an immunity-inducing agent. The present invention also aims to provide a method for detection of cancer, which is useful for diagnosis of cancer.

Means for Solving the Problems

The present inventors intensively studied to obtain, by the SEREX method using serum from a canine patient from which a canine breast cancer tissue-derived cDNA library was prepared, cDNA encoding a protein which binds to antibodies existing in the serum derived from the tumor-bearing living body, and, based on a the cDNA, canine CD179b polypeptides having the amino acid sequences shown in the odd number IDs of SEQ ID NOs:5 to 95 (that is, SEQ ID NOs:5, 7, 9, 11, 13, 15, ..., 91 and 93) in SEQUENCE LISTING were prepared. Further, based on a human homologous gene of the obtained genes, a human CD179b polypeptide having the amino acid sequence shown in SEQ ID NO:3 was prepared, and, similarly, based on a bovine homologous gene, a bovine CD179b polypeptide having the amino acid sequence shown in SEQ ID NO:95 was prepared. The present inventors then discovered that that these CD179b polypeptides are specifically expressed in breast cancer, leukemia and lymphoma cells. Further, the present inventors discovered that, by administration of these CD179b to a living body, immunocytes against CD179b can be induced in the living body, and a tumor in the living body expressing CD179b can be regressed. Further, the present inventors discovered that a recombinant vector comprising a polynucleotide encoding a CD179b polypeptide or a fragment thereof such that it can be expressed induces an anti-tumor effect against cancer expressing CD179b in the living body.

Further, the present inventors discovered that a partial polypeptide in a CD179b protein has a capacity to be presented by antigen-presenting cells, thereby allowing activation and growth of cytotoxic T cells specific to the peptide (immunity-inducing activity), and therefore that the peptide is useful for therapy and/or prophylaxis of cancer, and, further, that antigen-presenting cells contacted with the peptide and T cells contacted with the antigen-presenting cells are useful for the therapy and/or prophylaxis of cancer. Further, the present inventors discovered that, since a recombinant polypeptide prepared based on the amino acid sequence of the above CD179b protein specifically reacts only with serum of a tumor-bearing living body, cancer can be detected therewith. Based on the above discoveries, the present inventors completed the present invention.

Thus, the present invention has the following characteristics.

(1) An immunity-inducing agent comprising as an effective ingredient(s) at least one polypeptide selected from the polypeptides (a) to (c) below, the polypeptide(s) having an immunity-inducing activity/activities, or as an effective ingredient(s) a recombinant vector(s) which comprise(s) a polynucleotide(s) encoding the polypeptide(s) and is/are capable of expressing the polypeptide(s) in vivo:

(a) a polypeptide consisting essentially of not less than 7 consecutive amino acids in any one of the amino acid sequences shown in the odd number IDs of SEQ ID NOs:3 to 95 in SEQUENCE LISTING;

(b) a polypeptide having a sequence identity of not less than 90% with the polypeptide (a) and consisting essentially of not less than 7 amino acids; and (c) a polypeptide comprising the polypeptide (a) or (b) as a partial sequence thereof.

(2) The immunity-inducing agent according to (1) above, wherein the polypeptide (b) has a sequence identity of not less than 95% with the polypeptide (a).

(3) The immunity-inducing agent according to (1) above, wherein each of the polypeptide(s) having an immunity-inducing activity/activities is a polypeptide consisting essentially of not less than 7 consecutive amino acids in any one of the amino acid sequences shown in the odd number IDs of SEQ ID NOs:3 to 95 in SEQUENCE LISTING, or a polypeptide comprising the polypeptide as a partial sequence thereof.

(4) The immunity-inducing agent according to (3) above, wherein each of the polypeptide(s) having an immunity-inducing activity/activities is a polypeptide having any one of the amino acid sequences shown in the odd number IDs of SEQ ID NOs:3 to 95 in SEQUENCE LISTING.

(5) The immunity-inducing agent according to (3) above, wherein each of the polypeptide(s) having an immunity-inducing activity/activities is a polypeptide consisting essentially of not less than 7 consecutive amino acids in the region of aa1-34 or aa52-75 in any one of the amino acid sequences shown in the odd number IDs of SEQ ID NOs:3 to 95 in SEQUENCE LISTING, or a polypeptide comprising the polypeptide as a partial sequence thereof.

(6) The immunity-inducing agent according to (5) above, wherein each of the polypeptide(s) having an immunity-inducing activity/activities is a polypeptide consisting essentially of the amino acid sequence shown in SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116 or SEQ ID NO:117 in SEQUENCE LISTING, or a polypeptide comprising as a partial sequence thereof the amino acid sequence shown in SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116 or SEQ ID NO:117 in SEQUENCE LISTING, the polypeptide having 8 to 12 amino acid residues.

(7) The immunity-inducing agent according to any one of (1) to (6) above, comprising one or more of the polypeptides as an effective ingredient(s).

(8) The immunity-inducing agent according to (7) above, wherein the polypeptide(s) is/are an agent(s) for treating antigen-presenting cells.

(9) The immunity-inducing agent according to any one of (1) to (8) above, which is for therapy and/or prophylaxis of an animal cancer(s).

(10) The immunity-inducing agent according to (9) above, wherein the cancer(s) is/are a cancer(s) expressing the CD179b gene.

(11) The immunity-inducing agent according to (10), wherein the cancer(s) is/are breast cancer, leukemia and/or lymphoma.

(12) The immunity-inducing agent according to any one of (1) to (11) above, further comprising an immunoenhancer.

(13) An isolated antigen-presenting cell comprising a complex between the polypeptide having an immunity-inducing activity and an HLA molecule.

(14) An isolated T cell which selectively binds to a complex between the polypeptide having an immunity-inducing activity and an HLA molecule.

(15) A method for inducing immunity, the method comprising administering to an individual at least one polypeptide selected from the polypeptides (a) to (c) below, the polypeptide(s) having an immunity-inducing activity/activities, or a recombinant vector(s) which comprise(s) a polynucleotide(s)

encoding the polypeptide(s) and is/are capable of expressing the polypeptide(s) in vivo:

(a) a polypeptide consisting essentially of not less than 7 consecutive amino acids in any one of the amino acid sequences shown in the odd number IDs of SEQ ID NOs:3 to 95 in SEQUENCE LISTING;

(b) a polypeptide having a sequence identity of not less than 90% with the polypeptide (a) and consisting essentially of not less than 7 amino acids; and (c) a polypeptide comprising the polypeptide (a) or (b) as a partial sequence thereof.

(16) A method for detecting a cancer(s), which method is applied to a sample separated from a living body and comprises measuring expression of at least one of the polypeptides (a) to (c) below:

(a) a polypeptide consisting essentially of not less than 7 consecutive amino acids in any one of the amino acid sequences shown in the odd number IDs of SEQ ID NOs:3 to 95 in SEQUENCE LISTING;

(b) a polypeptide having a sequence identity of not less than 90% with the polypeptide (a) and consisting essentially of not less than 7 amino acids.

(c) a polypeptide comprising the polypeptide (a) or (b) as a partial sequence thereof.

(17) The method according to (16) above, wherein the measurement of expression of the polypeptide(s) is carried out by measuring an antibody/antibodies which may be contained in the sample by immunoassay, which antibody/antibodies was/were induced in the living body against the polypeptide(s) to be measured.

(18) A method for detecting a cancer(s), which is applied to a sample separated from a living body and comprises investigation of expression of the CD179b gene having a coding region having any one of the base sequences shown in SEQ ID NO:1 and the even number IDs of SEQ ID NOs:4 to 94 in SEQUENCE LISTING in a sample derived from a cancer patient, and comparison thereof with the expression level of the gene in a sample derived from a healthy individual.

(19) A reagent for detecting a cancer(s), the reagent comprising a polypeptide which undergoes antigen-antibody reaction with an antibody induced in a living body against the polypeptide of any one of (a) to (c) below:

(a) a polypeptide consisting essentially of not less than 7 consecutive amino acids in any one of the amino acid sequences shown in the odd number IDs of SEQ ID NOs:3 to 95 in SEQUENCE LISTING;

(b) a polypeptide having a sequence identity of not less than 90% with the polypeptide (a) and consisting essentially of not less than 7 amino acids; and (c) a polypeptide comprising the polypeptide (a) or (b) as a partial sequence thereof.

Effect of the Invention

By the present invention, a novel immunity-inducing agent useful for therapy and/or prophylaxis and/or the like of cancer is provided. As particularly described in later-mentioned Examples, by administering the polypeptide used in the present invention to a tumor-bearing animal, immunocytes can be induced in the body of the tumor-bearing animal, and a cancer which has already occurred can be reduced or regressed.

Further, by the present invention, a novel method for detection of cancer is provided. Since measurement of expression of the polypeptide in a sample by the method of the present invention enables detection of invisible small cancers and cancers which exist in deep parts of a body, the method is also useful for early detection of cancers in medical examinations and the like. If the method of the present invention is used in following-up of patients after cancer therapy, recurrence of the cancer can be detected in its early stage. Moreover, the method of the present invention makes it possible to assess the stage of cancer progression such as growth of the tumor, invasion of the tumor to the surrounding tissues, and metastasis of the cancer to lymph nodes and distant organs.

BRIEF DESCRIPTION OF THE DRAWINGS

In FIG. 1, reference numeral 1 in the ordinate represents the expression pattern of the gene identified as described above, and reference numeral 2 represents the expression pattern of the GAPDH gene as the control for comparison.

BEST MODE FOR CARRYING OUT THE INVENTION

<Polypeptide>

Figure 1:
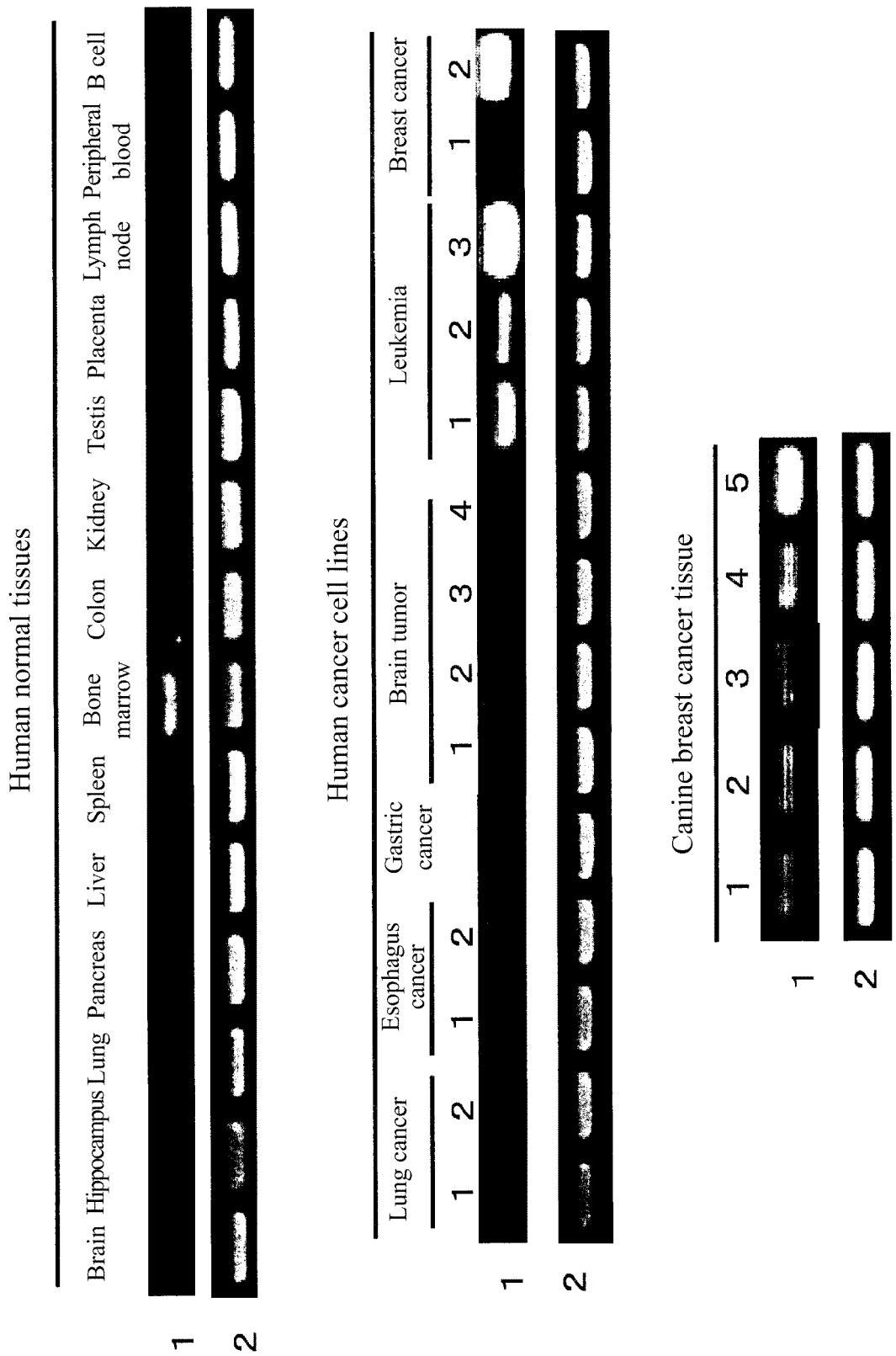
FIG. 1 is a diagram showing the expression patterns of the gene encoding the CD179b protein in normal tissues and tumor cell lines. Reference numeral 1 represents the expression pattern of the gene encoding the CD179b protein; and reference numeral 2 represents the expression pattern of the GAPDH gene.

Examples of the polypeptide contained in the immunity-inducing agent of the present invention as an effective ingredient include one or more polypeptide(s) selected from the polypeptides of (a), (b) and (c) below:

(a) a polypeptide which consists essentially of not less than 7 consecutive amino acids in a polypeptide having any one of the amino acid sequences shown in the odd number IDs of SEQ ID NOs:3 to 95 in SEQUENCE LISTING (that is, SEQ ID NO:3, 5, 7, 9, 11, 13, 15, . . . , 93 and 95) and has an immunity-inducing activity;

(b) a polypeptide having a sequence identity of not less than 90% with the polypeptide (a), consisting essentially of not less than 7 amino acids, and having an immunity-inducing activity; and (c) a polypeptide comprising the polypeptide (a) or (b) as a partial sequence thereof and having an immunity-inducing activity.

As used herein, the term "polypeptide" means a molecule formed by a plurality of amino acids linked together by peptide bonds, and includes not only polypeptide molecules having large numbers of amino acids constituting them, but also low-molecular-weight molecules having small numbers of amino acids (oligopeptides), and full-length molecules. In the present invention, proteins constituted by the total lengths of SEQ ID NO:3, 5, 7, 9, 11, 13, 15, ..., 93 and 95 are also included therein.

As used herein, the term "having an amino acid sequence" means that amino acid residues are arrayed in a specific order. Therefore, for example, "a polypeptide having the amino acid sequence shown in SEQ ID NO:3" means a polypeptide having the amino acid sequence of Leu Leu Arg Pro ... (snip) ... Ala Glu Cys Ser shown in SEQ ID NO:3, which polypeptide has a size of 176 amino acid residues. Further, for example, "polypeptide having the amino acid sequence shown in SEQ ID NO:3" may also be abbreviated as "polypeptide of SEQ ID NO:3". This also applies to the term "having a base sequence".

As used herein, the term "immunity-inducing activity" means an ability to induce immunocytes which secrete cytokines such as interferon in a living body.

Whether or not a polypeptide has an immunity-inducing activity can be confirmed using, for example, the known ELISPOT assay. More particularly, for example, as described in the Examples below, cells such as peripheral blood mononuclear cells are obtained from a living body to which a polypeptide whose immunity-inducing activity is to be evaluated was administered, which cells are then cocultivated with the polypeptide, followed by measuring the amount(s) of a cytokine(s) and/or a chemokine(s) such as IFN-γ and/or interleukin (IL) produced by the cells using a specific antibody/antibodies, thereby measuring the number of immunocytes in the cells, which enables evaluation of the immunity-inducing activity.

Alternatively, as described in the later-mentioned Examples, when a recombinant polypeptide prepared based on the amino acid sequence of SEQ ID NO:3, 5, 7, 9, 11, 13, 15, ..., 93 or 95 is administered to a tumor-bearing animal, the tumor can be reduced or regressed by its immunity-inducing activity. Thus, the above immunity-inducing activity can be evaluated also as an ability to suppress the growth of cancer cells expressing the polypeptide of SEQ ID NO:3, 5, 7, 9, 11, 13, 15, ..., 93 or 95, or to cause reduction or disappearance of a cancer tissue (tumor) (hereinafter referred to as "anti-tumor activity"). The anti-tumor activity of a polypeptide can be confirmed by, for example, observation of whether or not the tumor is reduced or regressed when the polypeptide was administered to a tumor-bearing living body, as more particularly described in the Examples below.

Alternatively, the anti-tumor activity of a polypeptide can be evaluated also by observation of whether or not T cells stimulated with the polypeptide (that is, T cells brought into contact with antigen-presenting cells presenting the polypeptide) show a cytotoxic activity against tumor cells in vitro. The contact between the T cells and the antigen-presenting cells can be carried out by cocultivation of the both in a liquid medium, as mentioned below. Measurement of the cytotoxic activity can be carried out by, for example, a known method called $^{51}$Cr release assay described in Int. J. Cancer, 58: p 317, 1994.

In cases where the polypeptide is used for therapy and/or prophylaxis of cancer, the evaluation of the immunity-inducing activity is preferably carried out using the anti-tumor activity as an index, although the index is not restricted.

The amino acid sequence shown in each of SEQ ID NOs:3, 5, 7, 9, 11, 13, 15, ... 93 and 95 in SEQUENCE LISTING is the amino acid sequence of a polypeptide which binds to an antibody specifically existing in serum derived from a tumor-bearing dog in the SEREX method using serum of the canine patient from which a canine mammary gland cancer-derived cDNA library was prepared, or the amino acid sequence of CD179b isolated as a human homologous factor (homologue) of the polypeptide (see Example 1 below). The polypeptide (a) is a polypeptide which consists essentially of not less than 7 consecutive amino acids, preferably 8, 9 or not less than 10 consecutive amino acids in a polypeptide having any one of the amino acid sequences shown in SEQ ID NO:3, 5, 7, 9, 11, 13, 15, ..., 93 and 95 in SEQUENCE LISTING and has an immunity-inducing activity. As known in the art, a polypeptide having not less than about 7 amino acid residues can exert its antigenicity and immunogenicity. Thus, a polypeptide having not less than 7 consecutive amino acid residues in the amino acid sequence shown in SEQ ID NO:3, 5, 7, 9, 11, 13, 15, ..., 93 or 95 can have an immunity-inducing activity, so that it can be used for preparation of the immunity-inducing agent of the present invention.

As a principle of immune induction by administration of a cancer antigenic polypeptide, the following process is known: the polypeptide is incorporated into an antigen-presenting cell and then degraded into smaller fragments by peptidases in the cell, followed by presentation of the fragments on the surface of the cell. The fragments are then recognized by a cytotoxic T cell or the like, which selectively kills cells presenting the antigen. The size of the polypeptide presented on the surface of the antigen-presenting cell is relatively small and about 7 to 30 amino acids. Therefore, from the view point of presenting thereof on the surface of the antigen-presenting cell, one preferred mode of the polypeptide (a) is a polypeptide composed of about 7 to 30 consecutive amino acids in the amino acid sequence shown in SEQ ID NO:3, 5, 7, 9, 11, 13, 15, ..., 93 or 95, and more preferably, a polypeptide composed of 8 to 30 or 9 to 30 amino acids is sufficient as the polypeptide (a). In some cases, these relatively small polypeptides are presented directly on the surface of the antigen-presenting cells without incorporation thereof into the antigen-presenting cells.

Further, since a polypeptide incorporated into an antigen-presenting cell is cleaved at random sites by peptidases in the cell to yield various polypeptide fragments, which are then presented on the surface of the antigen-presenting cell, administration of a large polypeptide such as the entire region of SEQ ID NO:3, 5, 7, 9, 11, 13, 15, ..., 93 or 95 inevitably causes production of polypeptide fragments by degradation thereof in the antigen-presenting cell, which fragments are effective for immune induction via the antigen-presenting cell. Therefore, also for immune induction via antigen-presenting cells, a large polypeptide can be used, and the polypeptide may be composed of not less than 30, preferably not less than 100, more preferably not less than 200 amino acids, which polypeptide may be still more preferably composed of the entire region of SEQ ID NO:3, 5, 7, 9, 11, 13, 15, ..., 93 or 95.

Further, the polypeptides of the present invention can be checked with a checking medium by which epitope peptides having binding motifs of various types of HLA and composed of 8 to 12, preferably 9 to 10 amino acids can be searched, for example, HLA Peptide Binding Predictions (<http://www-bimas.cit.nih.gov/molbio/hla_bind/>) in Bioinformatics & Molecular Analysis Selection (BIMAS), to screen peptides which may be epitope peptides. More particularly, a polypeptide composed of not less than 7 consecutive amino acids in the region of aa1-34 or aa52-75 in the amino acid sequence shown in SEQ ID NO:3, 5, 7, 9, 11, 13, 15, ..., 93 or 95 is preferred, and, in the polypeptide of SEQ ID NO:3, the polypeptides shown in SEQ ID NOs: 108 to 117 are more preferred.

The polypeptide (b) is the same polypeptide as the polypeptide (a) except that a small number of amino acid residues are substituted, deleted, added and/or inserted, which has a sequence identity of not less than 80%, preferably not less than 90%, more preferably not less than 95%, still more preferably not less than 98%, not less than 99% or not less than 99.5% to the original sequence, and has an immunity-inducing activity. It is well known in the art that, in general, there are cases where a protein antigen retains substantially the same antigenicity or immunogenicity as the original even if the amino acid sequence of the protein is modified such that a small number of amino acids are substituted, deleted, added and/or inserted. Therefore, since the polypeptide (b) may also exert an immunity-inducing activity, it can be used for preparation of the immunity-inducing agent of the present invention. Further, the polypeptide (b) is also preferably the same polypeptide as one having the amino acid sequence shown in SEQ ID NO:3, 5, 7, 9, 11, 13, 15, ..., 93 or 95 except that one or several amino acid residues are substituted, deleted, added and/or inserted.

As used herein, the term "sequence identity" in relation to amino acid sequences or base sequences means the value calculated by aligning two amino acid sequences (or base sequences) to be compared such that the number of matched amino acid residues (or bases) is maximum between the amino acid sequences (or base sequences), and dividing the number of matched amino acid residues (or the number of matched bases) by the total number of amino acid residues (or the total number of bases), which value is represented as a percentage (%). When the alignment is carried out, a gap(s) is/are inserted into one or both of the two sequences to be compared as required. Such alignment of sequences can be carried out using a well-known program such as BLAST, FASTA or CLUSTAL W (Karlin and Altschul, Proc. Natl. Acad. Sci. U.S.A., 87:2264-2268, 1993; Altschul et al., Nucleic Acids Res., 25:3389-3402, 1997). When a gap(s) is/are inserted, the above-described number of the total amino acid residues (or the total bases) is the number of residues (or bases) calculated by counting one gap as one amino acid residue (or base). When the thus counted numbers of the total amino acid residues (or bases) are different between the two sequences to be compared, the identity (%) is calculated by dividing the number of matched amino acid residues (or bases) by the number of the total amino acid residues (or the total bases) in the longer sequence.

Among substitutions of amino acid residues, conservative amino acid substitutions are preferred. The 20 types of amino acids constituting the naturally occurring proteins may be classified into groups each of which has similar properties, for example, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp, His). It is known that, in most cases, substitutions of amino acids within the same group, that is, conservative substitutions, do not change the properties of the polypeptide. Therefore, in cases where an amino acid residue(s) in the polypeptide (a) of the present invention is/are substituted, the probability that the immunity-inducing activity can be maintained may be made high by conducting the substitution(s) within the same group.

The polypeptide (c) comprises the polypeptide (a) or (b) as a partial sequence thereof and has an immunity-inducing activity. That is, the polypeptide (c) has another/other amino acid(s) or polypeptide(s) added at one end or the both ends of the polypeptide (a) or (b), and has an immunity-inducing activity. Such a polypeptide can also be used for preparation of the immunity-inducing agent of the present invention.

The above-described polypeptides can be synthesized by, for example, a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers. Further, the polypeptide of interest can be obtained using known genetic engineering techniques, by preparing a polynucleotide encoding the above polypeptide and incorporating the polynucleotide into an expression vector, which is then transfected into a host cell, followed by allowing the polypeptide to be produced in the host cell.

The polynucleotide encoding the above polypeptide can be easily prepared by a known genetic engineering technique or a conventional method using a commercially available nucleic acid synthesizer. For example, DNA having the base sequence shown in SEQ ID NO:4 can be prepared by carrying out PCR using a canine chromosomal DNA or cDNA library as a template, and a pair of primers designed such that the base sequence shown in SEQ ID NO:4 can be amplified therewith. In the case of DNA having the base sequence of SEQ ID NO:1, this can be similarly prepared by using a human chromosomal DNA or cDNA library as the template. The reaction conditions for the PCR can be set appropriately, and examples thereof include, but are not limited to, repeating the reaction process of 94° C. for 30 seconds (denaturation), 55° C. for 30 seconds to 1 minute (annealing) and 72° C. for 2 minutes (extension) for, for example, 30 cycles, followed by the reaction at 72° C. for 7 minutes. Methods, conditions and the like of PCR are described in, for example, Ausubel et al., Short Protocols in Molecular Biology, 3rd ed., A compendium of Methods from Current Protocols in Molecular Biology (1995), John Wiley & Sons (in particular, Chapter 15). Further, the desired DNA can be isolated by preparing an appropriate probe(s) or primer(s) based on the information of the base sequences and the amino acid sequences shown in SEQ ID NO:1 to 95 in SEQUENCE LISTING in the present specification, and screening a cDNA library of human, dog, bovine or the like using the probe(s) or primer(s). The cDNA library is preferably prepared from a cell, organ or tissue expressing the protein of SEQ ID NO:3, 5, 7, 9, 11, 13, 15, ..., 93 or 95. The above-described operations such as preparation of the probe(s) or primer(s), construction of a cDNA library, screening of the cDNA library and cloning of the gene of interest are known to those skilled in the art, and can be carried out according to the methods described in, for example, Sambrook et al., Molecular Cloning, Second Edition, Current Protocols in Molecular Biology (1989); and Ausubel et al. (described above). From the thus obtained DNA, DNA encoding the polypeptide (a) can be obtained. Further, since codons encoding each amino acid are known, a base sequence of a polynucleotide encoding a specific amino acid sequence can be easily specified. Therefore, the base sequences of polynucleotides encoding the polypeptide (b) and polypeptide (c) can also be easily specified, so that such polynucleotides can also be easily synthesized using a commercially available nucleic acid synthesizer according to a conventional method.

The host cells are not restricted as long as they can express the above-described polypeptide, and examples thereof include, but are not limited to, prokaryotic cells such as *E. coli*; and eukaryotic cells such as mammalian cultured cells including monkey kidney cells COS1, Chinese hamster ovary cells CHO, a human embryonic kidney cell line HEK293 and a mouse embryonic skin cell line NIH3T3; budding yeast; fission yeast; silkworm cells; and *Xenopus laevis* egg cells.

In cases where prokaryotic cells are used as the host cells, an expression vector having the origin that enables its replication in a prokaryotic cell, promoter, ribosome binding site, multicloning site, terminator, drug resistant gene, nutrient complementary gene and/or the like is used. Examples of the expression vector for *E. coli* include the pUC system, pBluescriptII, pET expression system and pGEX expression system. By incorporating a DNA encoding the above polypeptide into such an expression vector and transforming prokaryotic host cells with the vector, followed by culturing the resulting transformants, the polypeptide encoded by the DNA can be expressed in the prokaryotic host cells. In this process, the polypeptide can also be expressed as a fusion protein with another protein (e.g., green fluorescent protein (GFP) or glutathione S-transferase (GST)).

In cases where eukaryotic cells are used as the host cells, an expression vector for eukaryotic cells having a promoter, splicing site, poly(A) addition site and/or the like is used as the expression vector. Examples of such an expression vector include pKA1, pCDM8, pSVK3, pMSG, pSVL, pBK-CMV, pBK-RSV, EBV vector, pRS, pcDNA3, pMSG and pYES2. In the same manner as described above, by incorporating a DNA encoding the above polypeptide into such an expression vector and transforming eukaryotic host cells with the vector, followed by culturing the resulting transformants, the polypeptide encoded by the DNA can be expressed in the eukaryotic host cells. In cases where pIND/V5-His, pFLAG-CMV-2, pEGFP-N1, pEGFP-C1 or the like is used as the expression vector, the above polypeptide can be expressed as a fusion protein to which a tag such as His tag (e.g., $(His)_6$ to $(His)_{10}$), FLAG tag, myc tag, HA tag or GFP was added.

For the introduction of the expression vector into the host cells, well-known methods such as electroporation, the calcium phosphate method, the liposome method, the DEAE dextran method and microinjection can be used.

Isolation and purification of the polypeptide of interest from the host cells can be carried out by a combination of known separation operations. Examples of the known separation operations include, but are not limited to, treatment with a denaturant such as urea, or a surfactant; ultrasonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method include, as mentioned above, those in the form of a fusion protein with another arbitrary protein. Examples thereof include fusion proteins with glutathion S-transferase (GST) and with a His tag. Such a polypeptide in the form of a fusion protein is also included within the scope of the present invention as the polypeptide (c). Further, in some cases, a polypeptide expressed in a transformed cell is modified in various ways in the cell after translation thereof. Such a polypeptide modified after translation thereof is also included within the scope of the present invention as long as it has an immunity-inducing activity. Examples of such a post-translational modification include elimination of N-terminus methionine, N-terminus acetylation, glycosylation, limited degradation by an intracellular protease, myristoylation, isoprenylation and phosphorylation.

<Immunity-Inducing Agent>

As described concretely in the following Examples, the above-described polypeptide having an immunity-inducing activity can cause regression of an already occurred tumor when administered to a tumor-bearing animal. Therefore, the immunity-inducing agent of the present invention can be used as a therapeutic and/or prophylactic agent for cancer.

The terms "cancer" and "tumor" used in the present specification mean a malignant neoplasm, and are used interchangeably.

In this case, cancers to be treated are those expressing the CD179b gene, such as cancers expressing the gene encoding the polypeptide of SEQ ID NO: 3, 5, 7, 9, 11, 13, 15, . . . , 93 or 95, preferably breast cancer, leukemia and lymphoma. Examples of these particular cancers include, but are not limited to, breast cancers (mammary gland cancer, combined mammary gland cancer, mammary gland malignant mixed tumor, intraductal papillary adenocarcinoma and the like), leukemias (chronic lymphocytic leukemia and the like), lymphomas (gastrointestinal lymphoma, digestive organ lymphoma, small/medium cell lymphoma and the like).

The above-described polypeptide, or a recombinant vector comprising a polynucleotide encoding the polypeptide and capable of expressing the polypeptide in vivo can be used as a therapeutic method for immune induction. Further, it can be used as a therapeutic method for the purpose(s) of therapy and/or prophylaxis of animal cancer, and can also be used as a therapeutic method further comprising an immunoenhancer.

The subject animal is a mammal such as a primate, pet animal, domestic animal or sport animal, preferably human, dog or cat.

The administration route of the immunity-inducing agent of the present invention to a living body may be either oral administration or parenteral administration, and is preferably parenteral administration such as intramuscular administration, subcutaneous administration, intravenous administration or intraarterial administration. In cases where the immunity-inducing agent is used for therapy of cancer, it may be administered to a regional lymph node in the vicinity of the tumor to be treated, as described in the Examples below, in order to enhance its anticancer activity. The dose may be any dose as long as the dose is effective for immune induction, and, for example, in cases where the agent is used for therapy and/or prophylaxis of cancer, the dose may be one effective for therapy and/or prophylaxis of the cancer. Further, the dose may vary depending on the body weight, sex (male or female), symptoms and the like. The dose effective for therapy and/or prophylaxis of cancer is appropriately selected depending on the size of the tumor, the symptom and the like, and usually, 0.0001 µg to 1000 µg, preferably 0.001 µg to 1000 µg per subject animal per day, which may be administered once or in several times. The agent is preferably administered in several times, every several days to several months.

As concretely shown in the Examples below, the immunity-inducing agent of the present invention can cause reduction or regression of an already occurred tumor. Therefore, since the agent can exert its anticancer activity also against a small number of cancer cells in the early stage, development or recurrence of cancer can be prevented by using the agent before development of the cancer or after therapy for the cancer. That is, the immunity-inducing agent of the present invention is effective for both therapy and prophylaxis of cancer.

The immunity-inducing agent of the present invention may contain only a polypeptide or may be formulated by mixing as appropriate with an additive such as a pharmaceutically acceptable carrier, diluent or vehicle suitable for each administration mode. Formulation methods and additives which may be used are well-known in the field of formulation of pharmaceuticals, and any of the methods and additives may be used. Specific examples of the additives include, but are not limited to, diluents such as physiological buffer solutions; vehicles such as sucrose, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the formulation include oral preparations such as tablets, capsules, granules, powders and syrups; and parenteral preparations such as inhalants, injection solutions, suppositories and solutions. These formulations may be prepared by commonly known production methods.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Here, the patient is an animal, especially a mammal, preferably human, dog or cat.

Examples of the immunoenhancer include adjuvants. Adjuvants can enhance the immune response by providing a reservoir of antigen (extracellularly or within macrophages), activating macrophages and stimulating specific sets of lymphocytes, thereby enhancing the immune response and hence the anticancer action. Therefore, especially in cases where the immunity-inducing agent of the present invention is used for therapy and/or prophylaxis of cancer, the immunity-inducing agent preferably comprises an adjuvant, in addition to the above-described polypeptide as an effective ingredient. Many types of adjuvants are well-known in the art, and any of these adjuvants may be used. Specific examples of the adjuvants include MPL (SmithKline Beecham) and homologues of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*; DQS21 described in WO96/33739 (SmithKline Beecham); QS-7, QS-17, QS-18 and QS-L1 (So et al., "Molecules and cells", 1997, Vol. 7, p. 178-186); Freund's incomplete adjuvant; Freund's complete adjuvant; vitamin E; Montanide; alum; CpG oligonucleotides (for example, Kreig et al., Nature, Vol. 374, p. 546-549); poly-I:C and derivatives thereof (e.g., poly ICLC); and various water-in-oil emulsions prepared from biodegradable oils such as squalene and/or tocopherol. Among these, Freund's incomplete adjuvant; Montanide; poly-I:C and derivatives thereof; and CpG oligonucleotides are preferred. The mixing ratio between the above-described adjuvant and the polypeptide is typically about 1:10 to 10:1, preferably about 1:5 to 5:1, more preferably about 1:1. However, the adjuvant is not limited to the above-described examples, and adjuvants known in the art other than those described above (for example, Goding, "Monoclonal Antibodies: Principles and Practice, 2nd edition", 1986) may be used when the immunity-inducing agent of the present invention is administered.

Preparation methods for mixtures or emulsions of a polypeptide and an adjuvant are well-known to those skilled in the art of vaccination.

Further, in addition to the above-described adjuvants, factors that stimulate the immune response of the subject may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples thereof include, but are not limited to, interleukin-12 (IL-12), GM-CSF, IL-18, interferon-α, interferon-β, interferon-ω, interferon-γ, and Flt3 ligand, which have been shown to enhance the prophylactic action of vaccines. Such factors may also be used as the above-described immunoenhancer, and can be contained in the immunity-inducing agent of the present invention, or can be prepared as a separate composition to be used in combination with the immunity-inducing agent of the present invention, to be administered to a patient <Antigen-Presenting Cells>

As concretely described in the Examples below, by bringing the above-described polypeptide used in the present invention into contact with antigen-presenting cells in vitro, the antigen-presenting cells can be made to present the polypeptide. That is, the polypeptides (a) to (c) described above can be used as agents for treating antigen-presenting cells. Examples of the antigen-presenting cells include dendritic cells and B cells, and dendritic cells and B cells having MHC class I molecules are preferably employed. The agents for treating antigen-presenting cells mean agents for pulsing antigen-presenting cells, and, since pulsed antigen-presenting cells can have an ability to stimulate peripheral blood lymphocytes, the cells can be used as a vaccine.

Various MHC class I molecules have been identified and well-known. MHC molecules in human are called HLA. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

The dendritic cells or B cells having MHC class I molecules can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system.

By administering an effective amount of such dendritic cells, a response desired for therapy of a cancer can be induced. As the cells to be used, bone marrow or umbilical cord blood donated by a healthy individual, or bone marrow, peripheral blood or the like from the patient himself may be used. When autologous cells of the patient are used, high safety can be attained and serious side effects are expected to be avoided. The peripheral blood or bone marrow may be a fresh sample, cold-stored sample or frozen sample. As for the peripheral blood, whole blood may be cultured or the leukocyte components alone may be separated and cultured, and the latter is efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. As for the cytokine to be used, the production method thereof is not restricted and naturally-occurring or recombinant cytokine or the like may be employed as long as its safety and physiological activity have been confirmed. Preferably, a preparation with assured quality for medical use is used in a minimum necessary amount. The concentration of the cytokine(s) to be added is not restricted as long as the dendritic cells are induced, and usually, the total concentration of the cytokine(s) is preferably about 10 to 1000 ng/mL, more preferably about 20 to 500 ng/mL. The culture may be carried out using a well-known medium usually used for culture of leukocytes. The culturing temperature is not restricted as long as the proliferation of the leukocytes is attained, and about 37° C. which is the body temperature of human is most preferred. The atmospheric environment during the culturing is not restricted as long as the proliferation of the leukocytes is attained, and 5% $CO_2$ is preferably allowed to flow. The culturing period is not restricted as long as a necessary number of the cells is induced therewith, and is usually 3 days to 2 weeks. As for the apparatuses used for separation and culturing of the cells, appropriate apparatuses, preferably those whose safety when applied to medical uses have been confirmed, and whose operations are stable and simple, may be employed. In particular, as for the cell-culturing apparatus, not only the general vessels such as a Petri dish, flask and bottle, but also a layer type vessel, multistage vessel, roller bottle, spinner type bottle, bag type culturing vessel, hollow fiber column and the like may be used.

Bringing the above-described peptide into contact with the antigen presenting cells in vitro may be carried out by a well-known method. For example, it may be carried out by culturing the antigen-presenting cells in a culture medium containing the above-described polypeptide. The concentration of the peptide in the medium is not restricted, and usually about 1 μg/ml to 100 μg/ml, preferably about 5 μg/ml to 20 μg/ml. The cell density during the culturing is not restricted and usually about $10^3$ cells/ml to $10^7$ cells/ml, preferably about $5 \times 10^4$ cells/ml to $5 \times 10^6$ cells/ml. The culturing may be carried out according to a conventional method, and is preferably carried out at 37° C. under atmosphere of 5% $CO_2$. The maximum length of the peptide which can be presented on the surface of the antigen-presenting cells is usually about 30 amino acid residues. Therefore, in cases where the antigen-presenting cells are brought into contact with the polypeptide in vitro, the polypeptide may be prepared such that its length is not more than about 30 amino acid residues, although the length is not restricted.

By culturing the antigen-presenting cells in the coexistence of the above-described polypeptide, the polypeptide is incorporated into MHC molecules of the antigen-presenting cells and presented on the surface of the antigen-presenting cells. Therefore, using the above-described polypeptide, isolated antigen-presenting cells containing the complex between the polypeptide and the MHC molecules can be prepared. Such antigen-presenting cells can present the polypeptide against T cells in vivo or in vitro, and thereby induce, and allow proliferation of, cytotoxic T cells specific to the polypeptide.

By bringing the antigen-presenting cells prepared as described above having the complex between the above-described polypeptide and the MHC molecules into contact with T cells in vitro, cytotoxic T cells specific to the polypeptide can be induced and allowed to proliferate. This may be carried out by cocultivating the above-described antigen-presenting cells and T cells in a liquid medium. For example, it may be attained by suspending the antigen-presenting cells in a liquid medium, placing the suspension in vessels such as wells of a microplate, adding thereto T cells and then culturing the cells. The mixing ratio of the antigen-presenting cells to the T cells in the cocultivation is not restricted, and is usually about 1:1 to 1:100, preferably about 1:5 to 1:20 in terms of the ratio between the numbers of cells. The density of the antigen-presenting cells to be suspended in the liquid medium is not restricted, and is usually about 100 to 10,000,000 cells/ml, preferably about 10,000 to 1,000,000 cells/ml. The cocultivation is preferably carried out at 37° C. under atmosphere of 5% $CO_2$ in accordance with a conventional method. The culturing time is not restricted, and is usually 2 days to 3 weeks, preferably about 4 days to 2 weeks. The cocultivation is preferably carried out in the presence of one or more interleukins such as IL-2, IL-6, IL-7 and/or IL-12. In this case, the concentration of IL-2 and IL-7 is usually about 5 U/ml to 20 U/ml, the concentration of IL-6 is usually about 500 U/ml to 2000 U/ml, and the concentration of IL-12 is usually about 5 ng/ml to 20 ng/ml, but the concentrations of the interleukins are not restricted thereto. Here, "U" indicates the unit of activity. The above cocultivation may be repeated once to several times adding fresh antigen-presenting cells. For example, the operation of discarding the culture supernatant after the cocultivation and adding a fresh suspension of antigen-presenting cells to further conduct the cocultivation may be repeated once to several times. The conditions of the each cocultivation may be the same as described above.

By the above-described cocultivation, cytotoxic T cells specific to the polypeptide are induced and allowed to proliferate. Thus, using the above-described polypeptide, isolated T cells can be prepared which selectively bind the complex between the polypeptide and the MHC molecule.

As described in the Examples below, the genes encoding the polypeptides of SEQ ID NOs:3, 5, 7, 9, 11, 13, 15, ..., 93 and 95 are expressed specifically in breast cancer cells, leukemia cells and lymphoma cells. Therefore, it is thought that, in these cancer species, significantly higher numbers of the polypeptides of SEQ ID NOs:3, 5, 7, 9, 11, 13, 15, ..., 93 and 95 exist than in normal cells. When cytotoxic T cells prepared as described above are administered to a living body while a part of the polypeptides existing in cancer cells are presented by MHC molecules on the surfaces of the cancer cells, the cytotoxic T cells can damage the cancer cells using the presented polypeptides as markers. Since antigen-presenting cells presenting the above-described polypeptides can induce, and allow proliferation of, cytotoxic T cells specific to the polypeptides also in vivo, cancer cells can be damaged also by administering the antigen-presenting cells to a living body. That is, the cytotoxic T cells and the antigen-presenting cells prepared using the polypeptide are also effective as therapeutic and/or prophylactic agents for cancer, similarly to the immunity-inducing agent of the present invention.

In cases where the above-described isolated antigen-presenting cells or isolated T cells are administered to a living body, these are preferably prepared by treating antigen presenting cells or T cells collected from the patient to be treated with the polypeptide (a) to (c) as described above in order to avoid the immune response in the living body that attacks these cells as foreign bodies.

The therapeutic and/or prophylactic agent for cancer comprising as an effective ingredient the antigen-presenting cells or T cells is preferably administered via a parenteral administration route such as intravenous or intraarterial administration. The dose is appropriately selected depending on the symptom, the purpose of administration and the like, and is usually 1 cell to 10,000,000,000,000 cells, preferably 1,000,000 cells to 1,000,000,000 cells, which dose is preferably administered once per several days to once per several months. The formulation may be, for example, the cells suspended in physiological buffered saline, and the formulation may be used in combination with another/other anticancer preparation(s) and/or cytokine(s). Further, one or more additives well-known in the field of formulation of pharmaceuticals may also be added.

<Gene Vaccine>

Also by expression of the polynucleotide encoding the polypeptide (a) to (c) in the body of the subject animal, antibody production and cytotoxic T cells can be induced in the living body, and an effect comparable to that obtained in the case of administration of a polypeptide can be obtained. That is, the immunity-inducing agent of the present invention may be one comprising as an effective ingredient a recombinant vector having a polynucleotide encoding the polynucleotide (a) to (c), which recombinant vector is capable of expressing the polypeptide in a living body. Such a recombinant vector capable of expressing an antigenic polypeptide is also called gene vaccine.

The vector used for production of a gene vaccine is not restricted as long as it is a vector capable of expressing a polypeptide in a cell of the subject animal (preferably in a mammalian cell), and may be either a plasmid vector or a virus vector, and any known vector in the field of gene vaccines may be used. The polynucleotide such as DNA or RNA encoding the above-described polypeptide can be easily prepared, as mentioned above, by a conventional method. Incorporation of the polynucleotide into the vector can be carried out using a method well-known to those skilled in the art.

The administration route of the gene vaccine is preferably a parenteral route such as intramuscular, subcutaneous, intravenous or intraarterial administration, and the dose may be appropriately selected depending on the type of the antigen and the like, and usually about 0.1 μg to 100 mg, preferably about 1 μg to 10 mg in terms of the weight of the gene vaccine per 1 kg of body weight.

Methods using a virus vector include those wherein a polynucleotide encoding the above-described polypeptide is incorporated into an RNA virus or DNA virus, such as a retrovirus, adenovirus, adeno-associated virus, herpes virus, vaccinia virus, pox virus, poliovirus or Sindbis virus, and then the subject animal is infected with the resulting virus. Among these methods, those using a retrovirus, adenovirus, adeno-associated virus, vaccinia virus or the like are especially preferred.

Examples of other methods include a method wherein an expression plasmid is directly intramuscularly administered (DNA vaccine method), the liposome method, lipofectin method, microinjection method, calcium phosphate method and electroporation method, and the DNA vaccine method and liposome method are especially preferred.

Methods for actually making the gene encoding the above-described polypeptide used in the present invention act as a pharmaceutical include the in vivo method wherein the gene is directly transfected into the body, and the ex vivo method wherein a kind of cells are collected from the subject animal and the gene is transfected into the cells ex vivo, followed by returning the cells to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these papers and the like). The in vivo method is more preferred.

In cases where the gene is administered by the in vivo method, the gene may be administered through an appropriate administration route depending on the disease to be treated, symptom and so on. It may be administered by, for example, intravenous, intraarterial, subcutaneous, intramuscular administration or the like, or may be directly administered to the affected area in which a tumor exists. In cases where the gene is administered by the in vivo method, the gene may be formulated into a preparation such as a solution, and in general, it is formulated into an injection solution or the like containing DNA encoding the above-described peptide of the present invention as an effective ingredient. A commonly used carrier(s) may be added thereto as required. In the case of a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence shown in SEQ ID NO:1" includes not only the base sequence expressly written in SEQ ID NO:1, but also the sequence complementary thereto. Thus, "a polynucleotide having the base sequence shown in SEQ ID NO:1" includes a single-stranded polynucleotide having the base sequence expressly written in SEQ ID NO:1, a single-stranded polynucleotide having the base sequence complementary thereto, and a double-stranded polynucleotide composed of these single-stranded polynucleotides. When the polynucleotide encoding the polypeptide used in the present invention is prepared, any one of these base sequences should be appropriately selected, and those skilled in the art can easily carry out the selection.

<Detection of Cancer>

In a method of the present invention for detection of cancer, expression of the polypeptide used in the present invention is measured using a sample separated from a living body. The method for measuring the expression of a polypeptide using the sample includes a method in which an antibody against the polypeptide, which antibody is contained in the sample, is measured by immunoassay (Method 1); a method in which the polypeptide per se contained in the sample is measured by immunoassay (Method 2); and a method in which mRNA contained in the sample which encodes the polypeptide is measured (Method 3). In the method of the present invention, the expression of the polypeptide may be measured by any of these three methods. In the present invention, the term "measurement" includes detection, quantification and semi-quantification.

Here, CD179b was identified as a polypeptide which binds to an antibody (cancer-specific antibody) specifically existing in serum derived from a tumor-bearing dog, by the SEREX method using serum from a canine patient from which a canine breast cancer-derived cDNA library was prepared (see Example 1). That is, in the living body of a tumor-bearing dog, an antibody against CD179b is specifically induced. Thus, also by measuring an antibody against CD179b in a tumor-bearing living body, a cancer expressing CD179b can be detected (see Example 7). Further, a canine cancer can be detected also by measuring CD179b as an antigen by the above Method 2. Further, since, as described in the Examples below, mRNA encoding the antigen polypeptide is significantly more highly expressed in cancer, especially in breast cancer and leukemia cells, than in normal tissues (see Example 1), a canine cancer can be detected also by measuring the mRNA. As mentioned above, CD179b is known to be expressed on the membrane surfaces of precursor cells of B cells (pre-B cells), and therefore it is reported that CD179b is expressed in leukemia (pre-B cell leukemia) cells derived by cancerization of pre-B cells, but the fact that leukemia cells other than pre-B cell leukemia cells and breast cancer cells show expression of CD179b was first discovered in the present invention. Accordingly, detection of leukemia other than pre-B cell leukemia cells, lymphoma and breast cancer became possible by investigating expression of CD179b.

In Method 1 above, measurement of the cancer-specific antibody which may exist in the sample can be easily carried out by immunoassay using an antigenic substance which immunologically reacts with the antibody. The immunoassay per se is a conventional well-known method as explained in detail below. As the antigenic substance which may be used in the immunoassay, the polypeptide (a) to (c) may be used. As antibodies have cross-reactivity, a molecule may be bound to an antibody which is induced against another immunogen, as long as the molecule has any structure thereon which is similar to the epitope of the immunogen. For example, polypeptides having high amino acid sequence homology to each other often have epitopes with similar structures, and in such cases the both polypeptides may have the same antigenicity. As concretely described in the Examples below, the human-derived polypeptide of SEQ ID NO:3 immunologically reacts with the antibody induced in the body of a tumor-bearing dog. Therefore, in Method 1 of the present invention, any mammalian homologous factor may be used as an antigen in the immunoassay.

Antigenic substances having a large molecular weight and a complex structure, such as proteins, usually have a plurality of sites with different structures on their surface. Therefore, such an antigenic substance induces a plurality of kinds of antibodies which respectively recognize each of the sites in a living body. That is, an antibody induced in a living body against an antigenic substance such as a protein is a polyclonal antibody, which is a mixture of a plurality of kinds of antibodies. It should be noted that, in the present invention, the term "polyclonal antibody" means an antibody which exists in serum derived from a living body having an antigenic substance therein and is induced in the living body against the antigenic substance.

Measurement of the antibody in a sample may easily be carried out by immunoassay using the above-described polypeptide as an antigen. Immunoassays per se are well-known in the art, and includes, when classified based on the reaction mode, the sandwich method, competition method, agglutination method, Western blotting and the like. When classified based on the label, immunoassays include radioimmunoassay, fluorescence immunoassay, enzyme immunoassay, biotin immunoassay and the like, and the immunoassay of the above-described antibody may be carried out by any of these immunoassays. Although not restricted, the sandwich ELISA and agglutination method may be preferably used as an immunoassay of the above antibody in the present invention, as these methods are simple and do not require a large-scale apparatus. In cases where an enzyme is used as a label of an antibody, the used enzyme is not particularly restricted as long as it satisfies such conditions that the turnover number is large, that the enzyme is stable even when it is bound to an antibody, that it specifically colors its substrate and the like. For example, enzymes used in an ordinary enzyme immunoassay such as peroxidase, β-galactosidase, alkaline phosphatase, glucose oxidase, acetylcholinesterase, glucose-6-phosphate dehydrogenase, and malate dehydrogenase may be used. Enzyme inhibitors, coenzymes and the like may also be used. Binding of these enzymes with an antibody may be carried out by a known method using a cross-linking agent such as a maleimide compound. As a substrate, known substances may be used depending on the kind of the used enzyme. For example, in cases where peroxidase is used as the enzyme, 3,3',5,5'-tetramethylbenzidine may be used; and in cases where alkaline phosphatase is used as the enzyme, para-nitrophenol or the like may be used. As the radioisotope, those used in an ordinary radioimmunoassay such as $^{125}$I or $^3$H may be used. As the fluorescent dye, one used in an ordinary fluorescent antibody technique, such as fluorescein isothiocyanate (FITC), tetramethylrhodamine isothiocyanate (TRITC) or the like may be used.

These immunoassays per se are well-known in the art, and so it is not necessary to explain these immunoassays in the present specification. Briefly, in sandwich immunoassays, for example, the above-mentioned polypeptide used as an antigen is immobilized on a solid phase, and then reacted with a sample such as a serum. After washing the solid phase, the resultant is reacted with an appropriate secondary antibody. After washing the solid phase, the secondary antibody bound to the solid phase is measured. In the method for detecting cancer according to the present invention, it is preferred to immobilize an antigen polypeptide on a solid phase, because immobilization on a solid phase makes it possible to easily remove the unbound secondary antibody. As the secondary antibody, for example, anti-dog IgG antibody may be used in cases where the sample is obtained from dogs. The secondary antibody bound to the solid phase may be measured by labeling the secondary antibody with a labeling substance exemplified above. The thus measured amount of the secondary antibody corresponds to the amount of the above-mentioned antibody in a serum sample. In cases where an enzyme is used as the labeling substance, the amount of the antibody may be measured by adding a substrate which is decomposed by the enzymatic activity to develop a color, and then optically measuring the amount of decomposed substrate. In cases where a radioisotope is used as the labeling substance, the amount of radiation from the radioisotope may be measured with a scintillation counter or the like.

In Method 2 of the present invention, the polypeptide shown in SEQ ID NO:3, 5, 7, 9, 11, 13, 15, . . . , 93 or 95 is measured, which polypeptide may be contained in the sample obtained from a living body. As explained above, the abundance of the cancer-specific antibody which immunologically reacts with the polypeptide shown in SEQ ID NO:3, 5, 7, 9, 11, 13, 15, . . . , 93 or 95 or a homologous factor thereof is significantly high in cancer patients, which indicates that the production of the polypeptide or a homologous factor thereof, which is the antigen of the cancer-specific antibody, is significantly high in the cancer patients. Therefore, similarly to Method 1 above, cancers in a living body can be detected by measuring the polypeptide shown in SEQ ID NO:3, 5, 7, 9, 11, 13, 15, . . . , 93 or 95 or a homologous factor thereof.

Measurement of the polypeptide in a sample may easily be carried out by a well-known immunoassay. Specifically, for example, the polypeptide having the amino acid sequence shown in the odd number ID of SEQ ID NOs:3 to 95 or a homologous factor thereof which may exist in a sample may be measured by preparing an antibody or antigen-binding fragment thereof which immunologically reacts with the polypeptide having the amino acid sequence shown in the odd number ID of SEQ ID NOs:3 to 95 or a homologous factor thereof, and then carrying out an immunoassay using the prepared antibody or fragment thereof. The immunoassay per se is a well-known conventional method as described above.

The term "antigen-binding fragment" herein means an antibody fragment such as the Fab fragment or the F(ab')$_2$ fragment contained in an antibody molecule, which has a binding capacity to an antigen. Although the antibody may be either a polyclonal antibody or monoclonal antibody, a monoclonal antibody is preferred for immunoassays and the like, because a high reproducibility is attained therewith. Methods for preparing a polyclonal or monoclonal antibody using a polypeptide as an immunogen are well-known, and the preparation may be easily carried out by a conventional method. For example, antibodies against the polypeptide may be induced by immunizing an animal with an immunogen, the polypeptide conjugated to a carrier protein such as keyhole limpet hemocyanin (KLH) or casein, together with an adjuvant. Then antibody-producing cells such as spleen cells or lymphocytes are collected from the immunized animal and fused with myeloma cells to prepare hybridomas. Among the hybridomas, one producing an antibody which binds to the polypeptide shown in SEQ ID NO:3, 5, 7, 9, 11, 13, 15, . . . , 93 or 95 or a homologous factor thereof is selected and proliferated, and then the monoclonal antibody whose corresponding antigen is the above-mentioned protein may be collected from the culture supernatant. The above-described method is a conventional well-known method.

In Method 3 of the present invention, mRNA encoding CD179b, which may be contained in a sample obtained from a living body, is measured. As concretely described in the Examples below, the expression level of mRNA encoding CD179b is significantly high in cancer, especially, breast cancer and leukemia cells. Therefore, cancers in a living body can be detected by measuring the mRNA in a sample.

In the detection method of the present invention, whether the subject living body suffers from cancer or not or the like is determined based on the expression level of the polypeptide measured as described above. Although the cancer detection may be attained simply by measuring the expression of the polypeptide in the subject living body, it is preferred to obtain the normal reference value by determining the expression level of the polypeptide (the amount of the antibody, polypeptide or mRNA) in one or more samples from healthy individuals to compare the measured value in the subject living body with the normal reference value, in view of increasing the detection accuracy. In order to further increase the detection accuracy, the cancer reference value may be obtained by determining the expression level of the polypeptide in samples obtained from many patients who have been revealed to suffer from cancer to compare the measured value of the subject living body with the both of the normal and cancer reference values. The above mentioned reference values may be determined by expressing the expression level of the polypeptide in each sample in values and calculating the average value thereof. The normal and cancer reference values may be determined beforehand by measuring the expression level of the polypeptide in many healthy and cancer subjects. Thus, when the measured value is compared with the reference values in the method of the present invention, the reference values may be those predetermined.

The detection method of the present invention may be carried out in combination with detection using other cancer antigens and/or cancer markers so that the detection accuracy of cancers can be more improved.

By the detection method of the present invention, cancers in a living body can be detected. The method of the present invention can detect even an invisible small tumor or a tumor which exists in a deep part of a body, and thus the method is useful for early detection of cancer. Further, by applying the detection method of the present invention to patients in the follow-up period after cancer therapy, the recurrent cancer, if any, can be detect in its early stage.

If the more cancer cells expressing the prescribed polypeptide to be measured in the present invention proliferate in a tumor-bearing living body, the more the polypeptides and mRNAs encoding them accumulate in the body, which causes the increased amount of the antibodies against the above-mentioned polypeptides in the serum. On the other hand, the more cancer cells decrease, the more the accumulated polypeptides and mRNAs encoding them decrease in the living body, which causes the decreased amount of the antibodies against the above-mentioned polypeptides in the serum. Thus, if the expression level of the prescribed polypeptide is high, it can be determined that tumor growth and/or metastasis of cancer occurred, i.e., the stage of progression of cancer is advanced.

Further, as shown in the Example below, when compared between the same kinds of tumors, a malignant one produces significantly higher amount of the antibodies than a benign one. Therefore, if the expression level of the prescribed polypeptides is high, it can be determined that the grade of cancer malignancy is higher. That is, the grade of cancer malignancy can also be detected by the method of the present invention.

Furthermore, the effect of the cancer therapy can be monitored based on the increase or decrease in the expression level of the prescribed polypeptides. Therefore, by observing the expression level of the above-mentioned polypeptides on an individual during or after cancer therapy, a clue to assess how much the administered anti-cancer agent was effective, or whether a portion of the tumor is left in the patient after extirpation of the tumor can be obtained, as well as a clue to find metastasis and/or recurrence as early as possible can be obtained during the follow-up. Appropriate treatment of cancer results in decrease in the expression level of the polypeptides compared to that in the tumor-bearing state before the therapy. In such a case, it can be judged that the effect of the therapy which was (is being) performed on the living body is/was good. In cases where the expression level of the polypeptides increases or is sustained, or once decreases and then increases, it can be judged that the effect of the therapy is not good enough. This may be a useful basis for selection of a therapeutic method, such as decision to change the therapeutic method or to change the dose of an anti-cancer agent.

Cancers to be detected by the method of the present invention are those expressing CD179b (excluding pre-B cell tumors), and examples thereof include, but are not limited to, mammary gland cancer, combined mammary gland cancer, mammary gland malignant mixed tumor, intraductal papillary adenocarcinoma, leukemias (preferably, chronic lymphocytic leukemia excluding those of the pre-B cell type) and lymphomas (preferably, gastrointestinal lymphoma, digestive organ lymphoma, small/medium cell lymphoma, medium cell lymphoma and multicentric lymphoma, excluding those of the pre-B cell type). The living bodies to which the method of the present invention applies are mammals, preferably humans, dogs and cats.

The sample to be subjected to the method of the present invention includes body fluids such as blood, serum, plasma, ascites and pleural effusion; tissues; and cells. In particular, serum, plasma, ascites and pleural effusion may be preferably used in Method 1 and Method 2 above. A tissue sample and cell sample are preferred in the case of Method 3 above in which mRNA is measured.

The polypeptide used as an antigen for immunoassay in Method 1 may be provided as a reagent for detecting cancer. The reagent may consist only of the above-mentioned polypeptide, or may contain various additives useful for stabilizing the polypeptide, and the like. The reagent may also be provided in the form of being immobilized on a solid phase such as a plate or membrane.

The antibody or an antigen-binding fragment thereof which immunologically reacts with the polypeptide of SEQ ID NO:3, 5, 7, 9, 11, 13, 15, . . . , 93 or 95 or a homologous factor thereof, which is used for measuring the polypeptide or the homologous factor thereof by immunoassay in Method 2, may also be provided as a reagent for detecting cancer. The reagent may also consist only of the above-mentioned antibody or antigen-binding fragment thereof, or may contain various additives useful for stabilizing the antibody or antigen-binding fragment thereof, and the like. The antibody or antigen-binding fragment thereof may also be in the form of being conjugated with a metal such as manganese or iron. Since such a metal-conjugated antibody or antigen-binding fragment thereof accumulates in a site in which a large amount of antigen protein exists when administered to a body, the existence of cancer cells which produce the antigen protein can be detected by measuring the metal by MRI or the like.

Furthermore, the above-described polynucleotide for cancer detection used for measuring mRNA in Method 3 may also be provided as a reagent for detecting cancer. The reagent for detecting cancer may also consist only of the polynucleotide, or may contain various additives useful for stabilizing the polynucleotide and the like. The polynucleotide for cancer detection contained in the reagent is preferably a primer or a probe.

EXAMPLES

The present invention will now be described more concretely by way of Examples, but the scope of the present invention is not limited to the particular examples below.

Example 1

Acquisition of Novel Cancer Antigen Protein by SEREX Method (1) Preparation of cDNA Library From a canine mammary gland cancer tissue removed by surgery, total RNA was extracted by the Acid guanidium-Phenol-Chloroform method, and poly(A)$^+$ RNA was purified using the Oligotex-dT30 mRNA purification Kit (manufactured by Takara Shuzo Co., Ltd.) according to the protocol described in the attached instructions.

Using the obtained mRNA (5 μg), a canine mammary gland cancer-derived cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $2.99 \times 10^5$ pfu/ml.

(2) Screening of cDNA Library with Serum

Using the canine mammary gland cancer-derived cDNA phage library prepared as described above, immunoscreening was carried out. More particularly, host E. coli (XL1-Blue MRF') was infected with the library such that 2340 clones were included in a Φ90×15 mm NZY agarose plate, followed by culture at 42° C. for 3 to 4 hours to allow formation of plaques. The plate was covered with a nitrocellulose membrane (Hybond C Extra; manufactured by GE Healthcare Bio-Science) impregnated with IPTG (isopropyl-β-D-thiogalactoside) at 37° C. for 4 hours, to allow induction and expression of proteins, thereby transferring the proteins to the membrane. Thereafter, the membrane was recovered and soaked in TBS (10 mM Tris-HCl, 150 mM NaCl pH 7.5) supplemented with 0.5% non-fat dry milk, followed by being shaken at 4° C. overnight to suppress nonspecific reactions. This filter was allowed to react with 500-fold diluted canine patient serum at room temperature for 2 to 3 hours.

As the above-described canine patient serum, a total of 3 serum samples were used which were collected from each of the dog from which the above mammary gland cancer was removed and another mammary gland cancer canine patient. These sera were stored at −80° C. and pretreated immediately before use. The pretreatment of the sera was carried out by the following method. That is, host E. coli (XL1-BLue MRF') was infected with λ ZAP Express phage into which no exogenous gene was inserted, and cultured on an NZY plate at 37° C. overnight. Subsequently, 0.2 M NaHCO$_3$ buffer (pH 8.3) containing 0.5 M NaCl was added to the plate, and the plate was left to stand at 4° C. for 15 hours, followed by recovering the supernatant as an E. coli/phage extract. Thereafter, the recovered E. coli/phage extract was passed through an NHS-column (manufactured by GE Healthcare Bio-Science) to immobilize the proteins derived from the E. coli/phage. The serum from the canine patient was passed through this protein-immobilized column and allowed to react with the proteins, thereby removing antibodies that adsorb to E. coli and the phage from the serum. The serum fraction passed through the column without being adsorbed was 500-fold diluted with TBS supplemented with 0.5% non-fat dry milk, and the resulting dilution was used as a material for the immunoscreening.

The membrane to which the thus treated serum and the above-described fusion proteins were blotted was washed with TBS-T (0.05% Tween 20/TBS) 4 times, and goat anti-dog IgG (Goat anti Dog IgG-h+l HRP conjugated; manufactured by BETHYL Laboratories, Inc.) which was 5000-fold diluted with TBS supplemented with 0.5% non-fat dry milk was allowed, as a secondary antibody, to react at room temperature for 1 hour. Detection was carried out by an enzymatic coloring reaction using the NBT/BCIP reaction solution (manufactured by Roche), and colonies whose positions were identical to those of positive sites of the coloring reaction were collected from the Φ90×15 mm NZY agarose plate, and dissolved into 500 μl of SM buffer (100 mM NaCl, 10 mM MgClSO$_4$, 50 mM Tris-HCl, 0.01% gelatin, pH 7.5). The second and third screenings were carried out by repeating the same method as described above until the colonies positive in the coloring reaction became single colonies, thereby isolating 45 positive clones after screening of 92820 phage clones reactive with IgG in the serum.

(3) Homology Search of Isolated Antigen Genes

To subject the 45 positive clones isolated by the above method to sequence analysis, an operation to convert the phage vector to a plasmid vector was carried out. More particularly, 200 μl of a solution prepared such that the host E. coli (XL1-Blue MRF') was contained to an absorbance OD$_{600}$ of 1.0, 250 μl of the purified phage solution and 1 μl of ExAssist helper phage (manufactured by STRATAGENE) were mixed together, and the resulting mixture was allowed to react at 37° C. for 15 minutes, followed by adding 3 ml of LB broth thereto and culturing the resultant at 37° C. for 2.5 to 3 hours. This was immediately followed by 20 minutes of incubation in a water bath at 70° C. and centrifugation at 1000×g for 15 minutes, after which the supernatant was collected as a phagemid solution. Subsequently, 200 μl of a solution prepared such that the phagemid host E. coli (SOLR) was contained to an absorbance OD$_{600}$ of 1.0 and 10 μl of the purified phagemid solution were mixed together, and the resulting mixture was allowed to react at 37° C. for 15 minutes, followed by plating a 50 μl aliquot of the resultant on LB agar medium supplemented with ampicillin (50 µg/ml final concentration) and culturing at 37° C. overnight. Single colonies of the transformed SOLR were picked up and cultured in LB medium supplemented with ampicillin (50 µg/ml final concentration) at 37° C., followed by purifying plasmid DNAs having inserts of interest using QIAGEN plasmid Miniprep Kit (manufactured by QIAGEN).

Each purified plasmid was subjected to analysis of the full-length sequence of the insert by the primer walking method using the T3 primer shown in SEQ ID NO:96 and the T7 primer shown in SEQ ID NO:97. By this sequence analysis, the gene sequences shown in the even number IDs of SEQ ID NOs:4 to 92 were obtained. Using the base sequences and the amino acid sequences (odd number IDs of SEQ ID NOs: 5 to 93) of these genes, homology search against known genes were carried out using a homology search program BLAST (<http://www.ncbi.nlm.nih.gov/BLAST/>), and, as a result, it was revealed that all the obtained 45 genes were those encoding CD179b. The homologies among the 45 genes were 94 to 99% in terms of the base sequences and 96 to 99% in terms of the amino acid sequences. The homologies between these genes and the gene encoding a human homologous factor were 62 to 82% in terms of the base sequences and 69 to 80% in terms of the amino acid sequences, in the region translated to a protein. The base sequence of the human homologous factor is shown in SEQ ID NO:1, and the amino acid sequences of the human homologous factor are shown in SEQ ID NOs:2 and 3. Further, the homologies between these genes and the gene encoding a bovine homologous factor were 68 to 82% in terms of the base sequences and 56 to 77% in terms of the amino acid sequences, in the region translated to a protein. The base sequence of the bovine homologous factor is shown in SEQ ID NO:94, and the amino acid sequence of the bovine homologous factor is shown in SEQ ID NO:95. The homology between the gene encoding the human homologous factor and the gene encoding the bovine homologous factor was 62% in terms of the base sequences and 72% in terms of the amino acid sequences, in the region translated to a protein.

(4) Analysis of Expression in Various Tissues

Expressions of the genes obtained by the above method in canine and human normal tissues and various cell lines were investigated by the RT-PCR (Reverse Transcription-PCR) method. The reverse transcription reaction was carried out as follows. That is, from 50 to 100 mg of each tissue or 5-10×10⁶ cells of each cell line, total RNA was extracted using the TRIZOL reagent (manufactured by INVITROGEN) according to the protocol described in the attached instructions. Using this total RNA, cDNA was synthesized by the Superscript First-Strand Synthesis System for RT-PCR (manufactured by INVITROGEN) according to the protocol described in the attached instructions. As the cDNAs of human normal tissues (brain, hippocampus, testis, colon and placenta), Gene Pool cDNA (manufactured by INVITROGEN), QUICK-Clone cDNA (manufactured by CLONETECH) and Large-Insert cDNA Library (manufactured by CLONETECH) were used. The PCR reaction was carried out as follows, using primers specific to the obtained canine genes (shown in SEQ ID NOs:98 and 99) and their human homologous gene (shown in SEQ ID NOs:100 and 101). That is, reagents and an attached buffer were mixed such that concentrations/amounts of 0.25 µl of a sample prepared by the reverse transcription reaction, 2 µM each of the above primers, 0.2 mM each of dNTPs, and 0.65 U ExTaq polymerase (manufactured by Takara Shuzo Co., Ltd.) were attained in a total volume of 25 µl, and the reaction was carried out with 30 cycles of 94° C. for 30 seconds, 60° C. for 30 seconds and 72° C. for 30 seconds using a Thermal Cycler (manufactured by BIO RAD). The above-described primers specific to genes having the base sequences shown in SEQ ID NOs: 98 and 99 were for amplification of the positions 32 to 341 in the base sequence shown in SEQ ID NO:4, and for amplification of the region common to all the canine CD179b genes shown in the even number IDs of SEQ ID NOs: 4 to 92. Further, the primers specific to genes having the base sequences shown in SEQ ID NOs:100 and 101 were for amplification of the positions 216 to 738 in the base sequence shown in SEQ ID NO:1. As a control for comparison, primers specific to GAPDH (shown in SEQ ID NOs:102 and 103) were used at the same time. As a result, as shown in FIG. 1, the obtained canine genes did not show expression in normal canine tissues at all, but showed strong expression in canine breast cancer tissues. In terms of expression of the human homologous gene, bone marrow was the only human normal tissue wherein its expression was confirmed, but, in human cancer cells, its expression was detected in leukemia cell lines and breast cancer cell lines, so that specific expression of CD179b in the leukemia cell lines and the breast cancer cell lines was confirmed.

In FIG. 1, reference numeral 1 in the ordinate represents the expression pattern of the gene identified as described above, and reference numeral 2 represents the expression pattern of the GAPDH gene as the control for comparison.

Example 2

Preparation of Canine and Human Novel Cancer Antigen Protein (1) Preparation of Recombinant Protein Based on the gene of SEQ ID NO:4 obtained in Example 1, a recombinant protein was prepared by the following method. That is, reagents and an attached buffer were mixed such that concentrations/amounts of 1 µl of the vector prepared from the phagemid solution obtained in Example 1 and subjected to the sequence analysis, 0.4 µM each of two kinds of primers having NdeI and KpnI restriction sites (described in SEQ ID NOs:104 and 105), 0.2 mM dNTP, and 1.25 U PrimeSTAR HS polymerase (manufactured by Takara Shuzo Co., Ltd.) were attained in a total volume of 50 µl, and PCR was carried out with 30 cycles of 98° C. for 10 seconds and 68° C. for 40 seconds using a Thermal Cycler (manufactured by BIO RAD). The above-described two kinds of primers were those for amplification of the region encoding the 5th to 120th amino acids in the amino acid sequence shown in SEQ ID NO:5. After the PCR, the amplified DNA was subjected to electrophoresis using 2% agarose gel, and a DNA fragment of about 350 bp was purified using QIAquick Gel Extraction Kit (manufactured by QIAGEN).

The purified DNA fragment was ligated into a cloning vector pCR-Blunt (manufactured by Invitrogen). E. coli was transformed with the resulting ligation product, and plasmids were recovered thereafter, followed by confirming, by sequencing, that the sequence of the amplified gene fragment matches the sequence of interest. The plasmid having the sequence that matched the sequence of interest was treated with restriction enzymes NdeI and KpnI and purified using QIAquick Gel Extraction Kit, followed by inserting the gene sequence of interest into an expression vector for E. coli, pET30b (manufactured by Novagen) that had been treated with restriction enzymes NdeI and KpnI. Usage of this vector enables production of a His-tag fusion recombinant protein. E. coli for expression, BL21 (DE3), was transformed with this plasmid, and expression of the protein of interest was induced in E. coli with 1 mM IPTG.

On the other hand, based on the gene of SEQ ID NO:1, a recombinant protein of the human homologous gene was prepared by the following method. Reagents and an attached buffer were mixed such that concentrations/amounts 1 µl of the cDNA prepared in Example 1 whose expression could be confirmed by the RT-PCR method in cDNAs from various tissues/cells, 0.4 µM each of two kinds of primers having EcoRI and SalI restriction sites (described in SEQ ID NOs: 106 and 107), 0.2 mM dNTP, and 1.25 U PrimeSTAR HS polymerase (manufactured by Takara Shuzo Co., Ltd.) were attained in a total volume of 50 µl, and PCR was carried out with 30 cycles of 98° C. for 10 seconds and 68° C. for 40 seconds using a Thermal Cycler (manufactured by BIO RAD). The above-described two kinds of primers were those for amplification of the total length the amino acid sequence shown in SEQ ID NO:3. After the PCR, the amplified DNA was subjected to electrophoresis using 2% agarose gel, and a DNA fragment of about 540 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the sequence of the amplified gene fragment matches the sequence of interest. The plasmid having the sequence that matched the sequence of interest was treated with restriction enzymes EcoRI and SalI and purified using QIAquick Gel Extraction Kit, followed by inserting the gene sequence of interest into an expression vector for *E. coli*, pET30a (manufactured by Novagen) that had been treated with restriction enzymes EcoRI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that express SEQ ID NO:1 and SEQ ID NO:4, respectively, were cultured in LB medium supplemented with 30 µg/mL kanamycin at 37° C. until the absorbance at 600 nm reached about 0.7, and then isopropyl-β-D-1-thiogalactopyranoside was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in phosphate-buffered saline and subjected to sonication on ice. The sonicated solution of *E. coli* was centrifuged at 7,000 rpm for 20 minutes to obtain the supernatant as the soluble fraction and the precipitate as the insoluble fraction.

The insoluble fraction was suspended in 4% Triton-X100 solution and centrifuged at 7,000 rpm for 20 minutes. This operation was repeated twice and an operation of removal of proteases was carried out.

The residue was suspended in 20 mM phosphate buffer (pH 8.0) containing 6M guanidine hydrochloride, and the resulting suspension was left to stand at 4° C. for 20 hours to denature proteins. Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 20 mM phosphate buffer (pH 8.0) containing 6M guanidine hydrochloride). The fraction that was not adsorbed to the column was washed away with 10 column volumes of 20 mM phosphate buffer (pH 8.0) containing 6M guanidine hydrochloride and 20 mM phosphate buffer (pH 8.0) containing 10 mM imidazole, and elution was immediately carried out with a four-step density gradient of 50 mM-500 mM imidazole, to obtain a purified fraction, which was used thereafter as a material for administration tests.

To 1 ml of a reaction buffer (20 mM Tris-HCl, 50 mM NaCl, 2 mM $CaCl_2$; pH 7.4), 200 µl of the purified preparation obtained by the above-described method was aliquoted, and 2 µl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 µm (manufactured by PALL) and used in the following experiments.

Example 3

Test of Administration of Recombinant Protein to Cancer-Bearing Dog (1) Antitumor Assay The anti-tumor effect of the recombinant protein which was purified as described above was assessed in a tumor-bearing dog (breast cancer) having an epidermal tumor.

An equal amount of Freund's incomplete adjuvant (manufactured by Wako Pure Chemicals) was mixed with 100 µg (0.5 ml) of the recombinant polypeptide purified as described above, to prepare a therapeutic agent for cancer. This was administered to a regional lymph node in the vicinity of the tumor a total of 3 times, by carrying out the subsequent administrations 3 days and 7 days after the first administration. As a result, the tumor with a size of about 55 $mm^3$ at the time of administration of the therapeutic agent for cancer was reduced in size to 30 $mm^3$ 10 days after the first administration; to 16 $mm^3$ 20 days after the first administration; and to 10 $mm^3$ 30 days after the first administration.

Further, to another canine patient suffering from mammary gland cancer, a mixture of 100 µg (0.5 ml) of the above-described polypeptide derived from dog and 0.5 ml of Freund's incomplete adjuvant was administered in the same manner as described above a total of 3 times. Further, concurrently with the respective administrations, 100 µg of canine interleukin 12 was administered subcutaneously. As a result, the tumor with a size of about 155 $mm^3$ at the time of administration of the therapeutic agent for cancer completely regressed 24 days after the first administration.

(2) Immune Inducibility Assay

Blood of the canine patient in which the anti-tumor effect was obtained in the administration test in the above-described (1) was collected before the administration of the therapeutic agent for cancer, and 10 days and 30 days after the first administration. Peripheral blood mononuclear cells were isolated according to a conventional method, and by the ELISPOT assay for IFNγ using them, the immune inducibility of each administered recombinant protein was assayed.

In a 96-well plate manufactured by Millipore (Multi-Screen-IP, MAIPS 4510), 100 µL/well of 70% ethanol was placed and the plate was left to stand for 5 minutes, followed by removal of the ethanol by aspiration. The plate was washed with sterile water and 300 μL/well of 200 mM Sodium Bicarbonate (pH8.2) was placed therein. After leaving it to stand for 5 minutes, Sodium Bicarbonate was removed by aspiration, and then the plate was washed. Subsequently, 0.5 μl/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 μL/well of a blocking solution (1% BSA-5% sucrose-200 mM Sodium Bicarbonate (pH8.2) was added to the wells, and the plate was incubated at 4° C. overnight to block the plate. After removal of the blocking solution by aspiration, 300 μL/well of 10% fetal calf serum-containing RPMI medium (manufactured by Invitrogen) was placed in the wells, and the plate was left to stand for 5 minutes, followed by removal of the medium by aspiration. Subsequently, $5 \times 10^5$ cells/well of the canine peripheral blood mononuclear cells suspended in 10% fetal calf serum-containing RPMI medium were placed in the plate, and 10 μL/well of the canine-derived polypeptide or human-derived polypeptide used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween 20-200 mM Sodium Bicarbonate (pH8.2)). In each well, 100 μL of rabbit anti-dog polyclonal antibody 1000-fold diluted with the above-described blocking solution was placed, and the plate was incubated at 4° C. overnight. After washing the wells 3 times with the above-described washing solution, 100 μL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and the number of the appeared spots was counted using KS ELISPOT (manufactured by Carl Zeiss, Inc.). As a result, in peripheral blood mononuclear cells sampled before the administration of the polypeptide, no spot was detected. On the other hand, in the canine patient after the administration of the polypeptide, 18 and 87 spots were detected in the peripheral blood mononuclear cells sampled 10 days and 30 days, respectively, after the administration.

From the above results, it was confirmed that immunocytes which specifically react with the administered recombinant protein and produce interferon γ were induced in the canine patient to which the recombinant protein was administered, and it was thought that the anti-tumor effect described in the above-described (1) was exerted by immunoreactions in which these immunocytes were mainly involved.

Example 4

Induction of CD8-Positive T Cells Reactive with Epitopes of CD179b-Derived Peptide (1) Prediction of Peptide Motifs Which Bind to HLA-A0201 and HLA-A24

Information on the amino acid sequence of the human CD 179b protein was obtained from GenBank. For prediction of HLA-A0201 and HLA-A24 binding motifs, the amino acid sequence of the human CD 179b protein was analyzed employing a computer-based prediction program using a known BIMAS software (available at <http://www-bimas.cit.nih.gov/molbio/hla_bind/>). As a result, 8 kinds of peptides shown in SEQ ID NOs:108 to 110 and SEQ ID NOs:113 to 117, which were expected to be capable of binding to the HLA-A0201 molecule; and 5 kinds of peptides shown in SEQ ID NOs:110 to 112, SEQ ID NO:115 and SEQ ID NO:116, which were expected to be capable of binding to the HLA-A24 molecule; were selected.

(2) Induction of Peptide Epitope-Reactive CD8-Positive T Cells

From an HLA-A0201-positive healthy individual, peripheral blood was isolated, and the peripheral blood was overlaid on Lymphocyte separation medium (OrganonpTeknika, Durham, N.C.), followed by centrifugation thereof at 1,500 rpm at room temperature for 20 minutes. A PBMC-containing fraction was recovered and washed 3 times (or more) with cold phosphate buffer to obtain peripheral blood mononuclear cells (PBMCs). The obtained PBMCs were suspended in 20 ml of AIM-V medium (manufactured by Life Technologies, Inc., Grand Island, N.Y.), and allowed to adhere to a culturing flask (manufactured by Falcon) at 37° C. under 5% $CO_2$ for 2 hours. The cells which were not adhered were used for the preparation of T cells, and the adhered cells were used for the preparation of dendritic cells.

The adhered cells were cultured in AIM-V medium in the presence of IL-4 (1000 U/ml) and GM-CSF (1000 U/ml). Six days later, the medium was replaced with AIM-V medium supplemented with IL-4 (1000 U/ml), GM-CSF (1000 U/ml), IL-6 (1000 U/ml, Genzyme, Cambridge, Mass.), IL-1β (10 ng/ml, Genzyme, Cambridge, Mass.) and TNF-α (10 ng/ml, Genzyme, Cambridge, Mass.), and the culturing was continued for another 2 days. The obtained population of cells which did not adhere was used as the dendritic cells.

The prepared dendritic cells were suspended in AIM-V medium at a cell density of $1 \times 10^6$ cells/ml, and the peptide shown in SEQ ID NOs:108 to 110 or SEQ ID NOs:113 to 117, which are sequences selected in the above (1) and expected to be capable of binding to the HLA-A201 molecule, was added to the resulting suspension at a concentration of 10 μg/ml, followed by culture using a 96-well plate under the conditions of 37° C., 5% $CO_2$ for 4 hours. Thereafter, the cells were irradiated with X-ray (3000 rad), washed with AIM-V medium, suspended in AIM-V medium containing 10% human AB serum (Nabi, Miami, Fla.), IL-6 (1000 U/ml) and IL-12 (10 ng/ml, Genzyme, Cambridge, Mass.), and placed in wells of a 24-well plate at a population of $1 \times 10^5$ cells/well. The prepared T cell population was added to the wells at a population of $1 \times 10^6$ cells/well, and the cells were cultured at 37° C. under 5% $CO_2$. Seven days later, each culture supernatant was discarded, and the cells were treated with each of the peptides obtained in the same manner as described above. After irradiation with X-ray, the dendritic cells were suspended in AIM-V medium containing 10% human AB serum (Nabi, Miami, Fla.), IL-7 (10 U/ml, Genzyme, Cambridge, Mass.) and IL-2 (10 U/ml, Genzyme, Cambridge, Mass.) (cell density: $1 \times 10^5$ cells/ml), and the cells were placed in wells of a 24-well plate at a cell population of $1 \times 10^5$ cells/well and further cultured. The same operations were repeated 4 to 6 times at intervals of 7 days, and the stimulated T cells were then recovered, after which induction of CD8-positive T cells were confirmed by flow cytometry.

Also for the peptides shown in SEQ ID NOs:110, 111, 112, 115 and 116, which were expected to be capable of binding to the HLA-A24 molecule, induction of peptide epitope-reactive CD8-positive T cells was attempted using dendritic cells and a T cell population induced from peripheral blood of an HLA-A24-positive healthy individual.

As a negative control, a peptide outside the scope of the present invention (SEQ ID NO:118) was used.

Example 5

Figure 2:
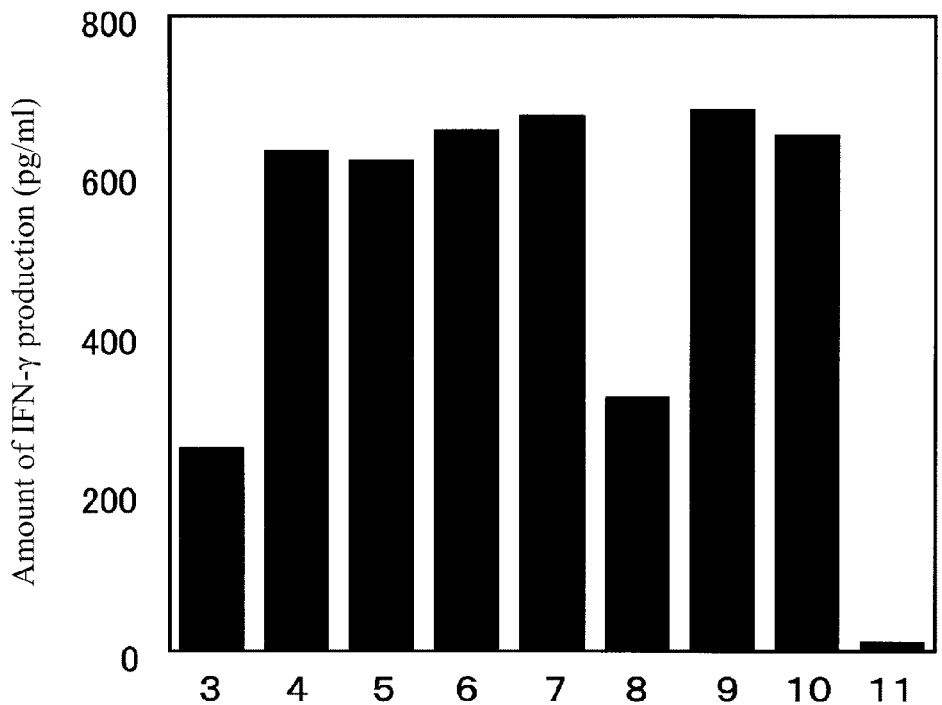
In FIG. 2, reference numerals 3, 4, 5, 6, 7, 8, 9 and 10 in the abscissa indicate the IFN-γ-producing abilities of HLA-A0201-positive CD8-positive T cells due to stimulation from T2 cells pulsed with the peptides of SEQ ID NOs:108, 109, 110, 113, 114, 115, 116 and 117, respectively. Reference numeral 11 indicates the result for the peptide of SEQ ID NO:118 used as the negative control (peptide having a sequence outside the scope of the present invention).

Determination of CD179b-Derived Cytotoxic T Cell Antigen Epitopes Which Stimulate HLA-A0201-Positive CD8-Positive T Cells (1) IFN-γ-Producing Ability In order to examine the specificity of each of the T cells, whose growth was confirmed among the T cells induced as described above, to peptide epitopes, $5 \times 10^3$ T cells were added to $5 \times 10^4$ T2 cells (Salter R D et al., Immunogenetics, 21:235-246 (1985), purchased from ATCC) which were pulsed with each peptide and expresses the HLA-A0201 molecule (cultured in AIM-V medium supplemented with each peptide at a concentration of 10 μg/ml, at 37° C. under 5% $CO_2$ for 4 hours), and the cells were cultured in AIM-V medium containing 10% human AB serum in a 96-well plate for 24 hours. The supernatant after the culturing was recovered and the production amount of IFN-γ was measured by ELISA. As a result, production of IFN-γ was confirmed in the culture supernatants in the wells of T2 cells pulsed with the peptides of SEQ ID NOs:108 to 110 and SEQ ID NOs:113 to 117, when compared with the culture supernatants in the wells of T2 cells which were not pulsed with a peptide (FIG. 2). From these results, it was revealed that the above-described peptides are T cell epitope peptides having a capacity to specifically stimulate, and allow proliferation of, the HLA-A0201-positive CD8-positive T cells, thereby inducing production of IFN-γ.

In FIG. 2, reference numerals 3, 4, 5, 6, 7, 8, 9 and 10 in the abscissa indicate the IFN-γ-producing abilities of the HLA-A0201-positive CD8-positive T cells due to stimulation from the T2 cells pulsed with the peptides of SEQ ID NOs:108, 109, 110, 113, 114, 115, 116 and 117, respectively. Reference numeral 11 indicates the result for the peptide of SEQ ID NO:118 used as the negative control.

(2) Cytotoxicity Assay

Figure 3:
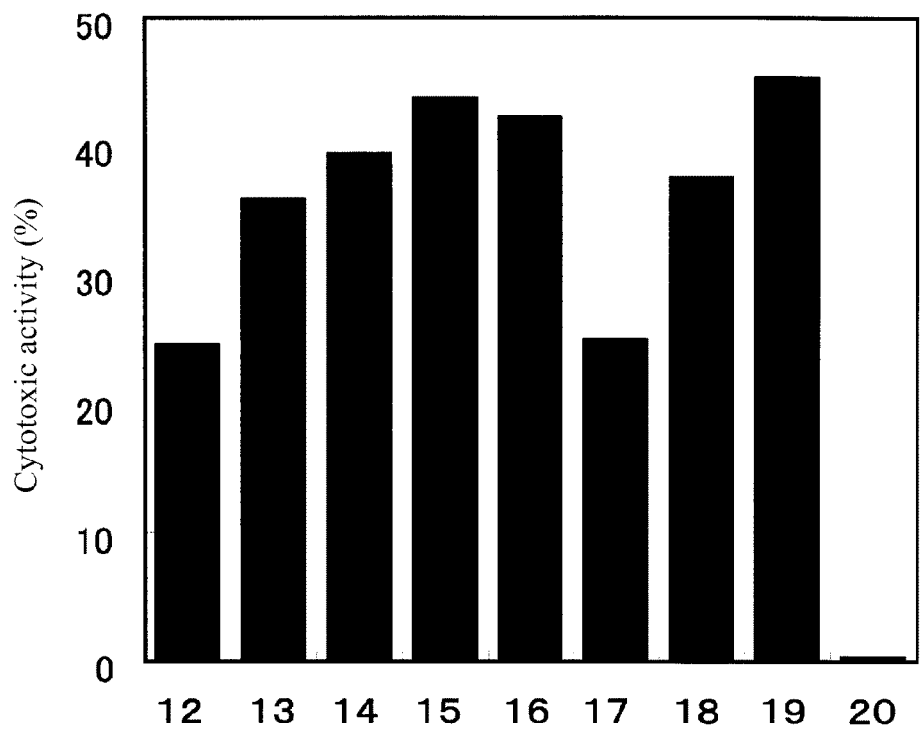
In FIG. 3, reference numerals 12, 13, 14, 15, 16, 17, 18 and 19 in the abscissa indicate the cytotoxic activities of HLA-A0201-positive CD8-positive T cells against Namalwa cells, which cells were stimulated using SEQ ID NOs:108, 109, 110, 113, 114, 115, 116 and 117, respectively. Reference numeral 20 indicates the cytotoxic activity of CD8-positive T cells induced using the peptide of the negative control (SEQ ID NO:118).

Subsequently, whether or not the peptides of SEQ ID NOs: 108 to 110 and SEQ ID NOs:113 to 117 used in the present invention are presented on the HLA-A0201 molecules on tumor cells which are HLA-A0201-positive and express CD179b, and whether or not the CD8-positive T cells stimulated by these peptides can damage the tumor cells which are HLA-A0201-positive and express CD179b were examined. In a 50-ml centrifugal tube, $10^6$ cells of a B cell leukemia cell line, Namalwa cells (purchased from ATCC), whose expression of CD179b had been confirmed, were collected, and 100 μCi of chromium 51 was added thereto, followed by incubation at 37° C. for 2 hours. Thereafter, the cells were washed 3 times with RPMI medium (manufactured by Gibco) containing 10% fetal calf serum (manufactured by Gibco), and placed in wells of a 96-well V-bottom plate in an amount of $10^3$ cells/well. Further, to each well, $5 \times 10^4$ T cells suspended in RPMI medium containing 10% fetal bovine serum, which cells were stimulated by each peptide, and HLA-A0201-positive, peptide epitope-reactive and CD8-positive, were added, followed by culture at 37° C. under 5% $CO_2$ for 4 hours. Thereafter, by measuring the amount of chromium 51 in the culture supernatant, which was released from the damaged tumor cells, the cytotoxic activity of the CD8-positive T cells stimulated by each peptide was calculated. As a result, it was revealed that the HLA-A0201-positive CD8-positive T cells stimulated by the peptide have a cytotoxic activity against Namalwa cells (FIG. 3). The CD8-positive T cells induced using the negative control peptide (SEQ ID NO:118) did not show a cytotoxic activity. Thus, it was proved that each of the peptides used in the present invention (SEQ ID NOs:108 to 110 and SEQ ID NOs:113 to 117) is presented on the HLA-A0201 molecules on tumor cells which are HLA-A0201-positive and express CD179b, and that the peptide has an ability to induce CD8-positive cytotoxic T cells which can damage such tumor cells.

The cytotoxic activity was determined by, as described above, mixing $10^5$ CD8-positive T cells stimulated and induced with each of the peptides used in the present invention and $10^3$ cells of the B cell leukemia cell line Namalwa which were made to incorporate chromium 51; culturing the resulting mixture for 4 hours; measuring the amount of chromium 51 released to the culture medium after the culturing; and calculating the cytotoxic activity of the CD8-positive T cells against the Namalwa cells according to the following equation*.

Cytotoxic activity(%)=the amount of chromium 51 released from Namalwa cells upon addition of CD8-positive T cells/the amount of chromium 51 released from the target cells upon addition of 1 N hydrochloric acid×100.   *Equation In FIG. 3, reference numerals 12, 13, 14, 15, 16, 17, 18 and 19 in the abscissa indicate the cytotoxic activities of the HLA-A0201-positive CD8-positive T cells against the Namalwa cells, which T cells were stimulated using SEQ ID NOs:108, 109, 110, 113, 114, 115, 116 and 117, respectively. Reference numeral 20 indicates the cytotoxic activity of CD8-positive T cells induced using the peptide of the negative control (SEQ ID NO:118).

Example 6

Figure 4:
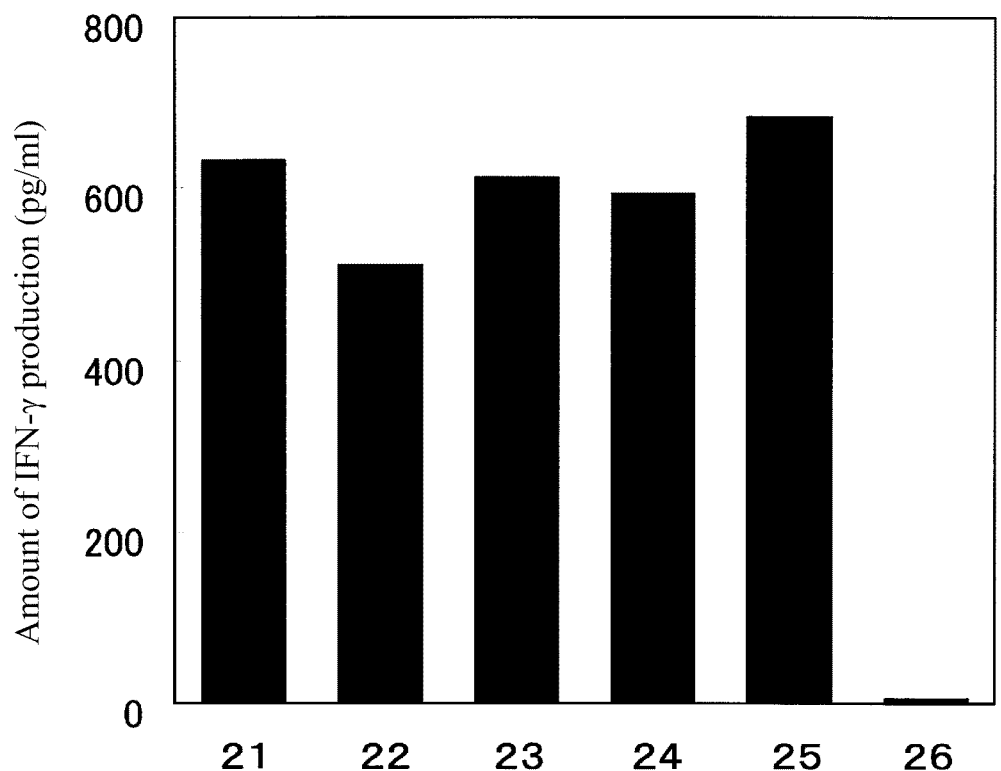
In FIG. 4, reference numerals 21, 22, 23, 24 and 25 in the abscissa indicate the IFN-γ-producing abilities of HLA-A24-positive CD8-positive T cells due to stimulation from JTK-LCL cells pulsed with the peptides of SEQ ID NOs:110, 111, 112, 115 and 116, respectively. Reference numeral 26 indicates the result for the peptide of SEQ ID NO:118 used as the negative control.

Determination of CD179b-Derived Cytotoxic T Cell Antigen Epitopes Which Stimulate HLA-A24-Positive CD8-Positive T Cells (1) IFN-γ-Producing Ability In order to examine the specificity of the peptide epitope-reactive CD8-positive T cells induced in Example 3(2) to peptide epitopes in the same manner as in Example 5(1), $5 \times 10^3$ cells of the above-described T cells were added to $5 \times 10^4$ JTK-LCL cells expressing HLA-A24 molecules (purchased from RIKEN), which JTK-LCL cells were pulsed using the peptide of SEQ ID NOs:110, 111, 112, 115 or 116 (cultured in AIM-V medium supplemented with each peptide at a concentration of 10 μg/ml, at 37° C. under 5% $CO_2$ for 4 hours), and the cells were cultured in AIM-V medium containing 10% human AB serum in a 96-well plate for 24 hours. The supernatant after the culturing was recovered and the production amount of IFN-γ was measured by ELISA. As a result, production of IFN-γ was confirmed in the culture supernatants in the wells of JTK-LCL cells pulsed with the peptides of SEQ ID NOs:110, 111, 112, 115 and 116, when compared with the culture supernatants in the wells of JTK-LCL cells which were not pulsed with a peptide (FIG. 4). From these results, it was revealed that the above-described peptides are T cell epitope peptides having a capacity to specifically stimulate, and allow proliferation of, the HLA-A24-positive CD8-positive T cells, thereby inducing production of IFN-γ.

In FIG. 4, reference numerals 21, 22, 23, 24 and 25 in the abscissa indicate the IFN-γ-producing abilities of the HLA-A24-positive CD8-positive T cells due to stimulation from the JTK-LCL cells pulsed with the peptides of SEQ ID NOs:

110, 111, 112, 115 and 116, respectively. Reference numeral 26 indicates the result for the peptide of SEQ ID NO:118 used as the negative control.

(2) Cytotoxicity Assay

Figure 5:
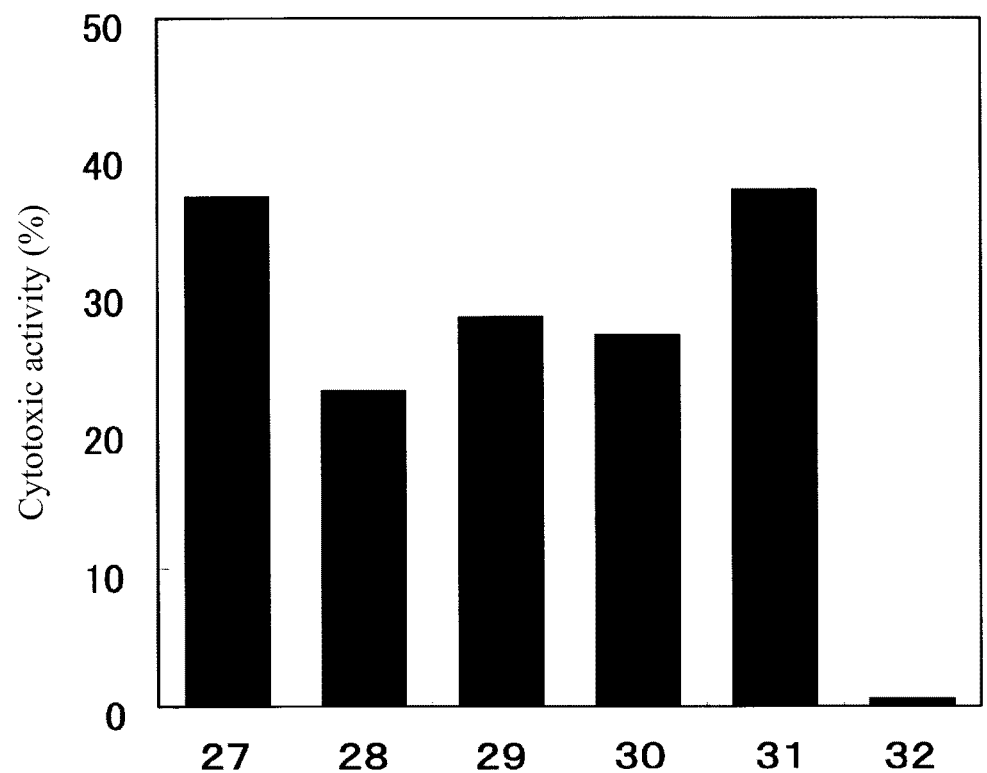
In FIG. 5, reference numerals 27, 28, 29, 30 and 31 indicate the cytotoxic activities of HLA-A24-positive CD8-positive T cells stimulated with the peptides of SEQ ID NO:110, 111, 112, 115 and 116, respectively, against JTK-LCL cells. Reference numeral 32 indicates the cytotoxic activity of CD8-positive T cells induced using the peptide of the negative control (SEQ ID NO:118).

Subsequently, whether or not the peptides of SEQ ID NOs: 110, 111, 112, 115 and 116 used in the present invention are presented on the HLA-A24 molecules on cells which are HLA-A24-positive and express CD179b, and whether or not the CD8-positive T cells stimulated by these peptides can damage the tumor cells which are HLA-A24-positive and express CD179b were examined in the same manner as in Example 5(2). In a 50-ml centrifugal tube, $10^6$ JTK-LCL cells, which are HLA-A24-positive and express CD179b, were collected, and 100 μCi of chromium 51 was added thereto, followed by incubation at 37° C. for 2 hours. Thereafter, the cells were washed 3 times with RPMI medium containing 10% fetal calf serum, and placed in wells of a 96-well V-bottom plate in an amount of $10^3$ cells/well. Further, to each well, $5\times10^4$ T cells suspended in RPMI medium containing 10% fetal calf serum, which cells were stimulated with each peptide, and HLA-A24-positive, peptide epitope-reactive and CD8-positive, were added, followed by culture at 37° C. under 5% $CO_2$ for 4 hours. Thereafter, by measuring the amount of chromium 51 in the culture supernatant, which was released from the damaged cells, the cytotoxic activity of the CD8-positive T cells stimulated by each peptide was calculated. As a result, it was revealed that the HLA-A24-positive CD8-positive T cells stimulated by the peptide have a cytotoxic activity against JTK-LCL cells (FIG. 5). Thus, it was proved that each of the peptides used in the present invention (SEQ ID NOs:110, 111, 112, 115 and 116) is presented on the HLA-A24 molecules on cells which are HLA-A24-positive and express CD179b, and that the peptide has an ability to induce CD8-positive cytotoxic T cells which can damage such cells. The CD8-positive T cells induced using the negative control peptide (SEQ ID NO:118) did not show a cytotoxic activity.

In FIG. 5, reference numerals 27, 28, 29, 30 and 31 indicate the cytotoxic activities of the HLA-A24-positive CD8-positive T cells stimulated with the peptides of SEQ ID NO:110, 111, 112, 115 and 116, respectively, against JTK-LCL cells. Reference numeral 32 indicates the cytotoxic activity of CD8-positive T cells induced using the peptide of the negative control (SEQ ID NO:118).

Example 7

Detection of Cancer Using Recombinant Protein (1) Detection of Canine Cancer

From 153 canine patients whose malignant tumor was confirmed and 264 healthy dogs, blood was collected, and sera were separated therefrom. Using the dog-derived cancer antigen protein prepared in Example 2 (the 5th to 120th amino acids in the amino acid sequence shown in SEQ ID NO:5) and anti-dog IgG antibody, the titer of IgG antibody in the sera which specifically reacts with the polypeptide was measured by ELISA.

Immobilization of the prepared polypeptide on a solid phase was carried out by placing 100 μL/well of the recombinant protein solution diluted to 100 μg/mL with phosphate-buffered saline in a 96-well Immobilizer Amino plate(manufactured by Nunc), followed by leaving the plate to stand at 4° C. overnight. Blocking was carried out by adding 100 μL/well of a solution, which was prepared by dissolving 4 g of Block Ace powder (manufactured by DS Pharma Biomedical Co., Ltd.) into 100 ml of purified water, into the wells, and shaking the plate at room temperature for 1 hour. The serum 1000-fold diluted with the blocking solution was added to the wells in an amount of 100 μL/well, and the plate was shaken at room temperature for 3 hours to allow the reaction to proceed. The wells were washed 3 times with phosphate-buffered saline containing 0.05% Tween 20 (manufactured by Wako Pure Chemical Industries, Ltd.) (hereinafter referred to as PBS-T), and 100 μL/well of HRP-modified dog IgG antibody (Goat anti Dog IgG(-H+L) HRP conjugated:: manufactured by BETHYL Laboratories) 3000-fold diluted with the blocking solution was added thereto, followed by shaking the plate at room temperature for 1 hour to allow the reaction to proceed. After washing the wells 3 times with PBS-T, 100 μl/well of an HRP substrate TMB (1-Step Turbo TMB (tetramethylbenzidine), PIERCE) was added, and the enzyme-substrate reaction was allowed to proceed at room temperature for 30 minutes. Thereafter, 100 μl/well of 0.5 M sulfuric acid solution (manufactured by Sigma-Aldrich Japan) was added to the wells to stop the reaction, and the absorbance at 450 nm was measured using a microplate reader. As a control, a case where the same operation was carried out in the same manner as described above except that the prepared recombinant protein was not immobilized, or except that the tumor-bearing dog serum was not reacted, was designed for comparison.

As the cancer species to be used for the above detection of cancer, 112 samples of breast cancer, 31 samples of lymphoma and 10 samples of leukemia which had been definitely diagnosed as malignant by pathological diagnosis were used.

These sera derived from the living bodies of the tumor-bearing dogs showed significantly high antibody titers against the recombinant protein. It was revealed that, by diagnosing a sample showing twice the average value of healthy canine samples as malignant, 61 samples (54%) of breast cancer, 21 samples (71%) of lymphoma and 7 samples (70%) of leukemia could be successfully diagnosed as malignant. When the test was similarly carried out using sera from 30 canine patients having a mammary gland tumor which had been definitely diagnosed as benign, the number of samples showing twice the average value of healthy canine samples was 0.

In the same manner, using the human-derived cancer antigen protein prepared in Example 2 (the amino acid sequence shown in SEQ ID NO:3) and anti-dog IgG antibody, the titer of IgG antibody which specifically reacts with the polypeptide in each of the above-described tumor-bearing dog serum samples was measured by ELISA. As a result, it was revealed that 56 samples (50%) of breast cancer, 18 samples (58%) of lymphoma and 5 samples (50%) of leukemia could be judged as malignant.

When the detection was carried out in the same manner as described above using pleural effusion and ascites collected from canine patients with terminal cancer, values similar to the results obtained by the detection method using serum could be detected, and diagnosis of the cancer was possible.

(2) Detection of Human Cancer

In the same manner, using the human-derived cancer antigen protein (the amino acid sequence shown in SEQ ID NO:3) used in the above detection and anti-human IgG antibody, the titer of IgG antibody in a healthy individual which specifically reacts with the polypeptide was measured. The secondary antibody to be used was an HRP-modified anti-human IgG antibody (manufactured by HRP-Goat Anti-Human IgG(H+L) Conjugate: manufactured by Zymed Laboratories) 10000-diluted with the blocking solution. As a positive control, egg white albumin which was prepared to 50 μg/ml with phosphate-buffered saline and immobilized on the solid phase was used. As a result, in the case of the egg white albumin, seven healthy individuals showed an absorbance of 0.45 at 450 nm on average, which was high. On the other hand, in the case of the above-described polypeptide, the absorbance was 0, which means that the reaction was not detected at all.

Further, in the same manner as described above, using 17 samples of sera derived from patients suffering from malignant breast cancer (purchased from Promeddx), the titer of IgG antibody in each serum which specifically reacts with the human-derived cancer antigen protein (amino acid sequence shown in SEQ ID NO:3) was similarly measured. As a result, in the case of the above-described polypeptide, the 17 breast cancer patients showed an absorbance of 0.28 at 450 nm on average, which was high. Thus, it was revealed that cancer can be detected by the present method also in human.

INDUSTRIAL APPLICABILITY

The present invention is useful for therapy of cancer since it provides an immunity-inducing agent containing a polypeptide which exerts an anti-tumor activity against a cancer(s) (tumor(s)) such as breast cancer, leukemia and/or lymphoma. Further, the present invention is useful for diagnosis of cancer since it provides a novel detection method for cancer.

The invention claimed is:

1. A method for reducing tumor activity in breast cancer, leukemia, and/or lymphoma, said method comprising administering a therapeutically effective amount of a polypeptide variant of SEQ ID NO: 3 having an amino acid sequence identity of not less than 99%
wherein said administration reduces tumor activity in breast cancer, leukemia, and/or lymphoma.

2. The method according to claim 1, further comprising administering a therapeutically effective amount of an immunoenhancer.

3. The method according to claim 2, wherein said immunoenhancer is polyionsinic-polycytidylic acid-polylysine carboxymethylcellullose (poly ICLC).

4. A method for reducing tumor activity in breast cancer, leukemia, and/or lymphoma, said method comprising administering a composition comprising:
(a) a therapeutically effective amount of a polypeptide comprising the amino acid sequence shown in SEQ ID NO:108, SEQ ID NO:109, SEQ ID NO:110, SEQ ID NO:111, SEQ ID NO:112, SEQ ID NO:113, SEQ ID NO:114, SEQ ID NO:115, or SEQ ID NO:116; wherein one amino acid residue is substituted, deleted, and/or inserted; and
(b) an immunoenhancer, wherein the immunoenhancer is polyionsinic-polycytidylic acid-polylysine carboxymethylcellullose (poly ICLC).

5. A method for reducing tumor activity in breast cancer, leukemia, and/or lymphoma, said method comprising administering a therapeutically effective amount of a polypeptide comprising the amino acid sequence shown in SEQ ID NO:117.

6. The method according to claim 5, further comprising administering a therapeutically effective amount of an immunoenhancer.

7. A method for reducing tumor activity in breast cancer, leukemia, and/or lymphoma, said method comprising administering a composition comprising:
(a) a therapeutically effective amount of a polypeptide variant of SEQ ID NO: 3 having an amino acid sequence identity of not less than 95%; and
(b) an immunoenhancer, wherein the immunoenhancer is polyionsinic-polycytidylic acid-polylysine carboxymethylcellullose (poly ICLC).

* * * * *

SEQUENCE LISTING

```
<160> NUMBER OF SEQ ID NOS: 118

<210> SEQ ID NO 1
<211> LENGTH: 901
<212> TYPE: DNA
<213> ORGANISM: Homo sapiens
<220> FEATURE:
<221> NAME/KEY: CDS
<222> LOCATION: (119)..(760)
<223> OTHER INFORMATION:
<220> FEATURE:
<221> NAME/KEY: sig_peptide
<222> LOCATION: (119)..(229)
<223> OTHER INFORMATION:

<400> SEQUENCE: 1
ggccacatgg actggggtgc aatgggacag ctgctgccag cgagagggac cagggcacca        60
ctctctaggg agcccacact gcaagtcagg ccacaaggac ctctgaccct gagggccg        118 atg agg cca ggg aca ggc cag ggg ggc ctt gag gcc cct ggt gag cca        166
Met Arg Pro Gly Thr Gly Gln Gly Gly Leu Glu Ala Pro Gly Glu Pro
1               5                   10                  15 ggc ccc aac ctc agg cag cgc tgg ccc ctg ctg ctg ctg ggt ctg gcc        214
Gly Pro Asn Leu Arg Gln Arg Trp Pro Leu Leu Leu Leu Gly Leu Ala
                20                  25                  30 gtg gta acc cat ggc ctg ctg cgc cca aca gct gca tcg cag agc agg        262
Val Val Thr His Gly Leu Leu Arg Pro Thr Ala Ala Ser Gln Ser Arg
            35                  40                  45 gcc ctg ggc cct gga gcc cct gga gga agc agc cgg tcc agc ctg agg        310
Ala Leu Gly Pro Gly Ala Pro Gly Gly Ser Ser Arg Ser Ser Leu Arg
        50                  55                  60 agc cgg tgg ggc agg ttc ctg ctc cag cgc ggc tcc tgg act ggc ccc        358
Ser Arg Trp Gly Arg Phe Leu Leu Gln Arg Gly Ser Trp Thr Gly Pro
65                  70                  75                  80 agg tgc tgg ccc cgg ggg ttt caa tcc aag cat aac tca gtg acg cat        406
Arg Cys Trp Pro Arg Gly Phe Gln Ser Lys His Asn Ser Val Thr His
                85                  90                  95 gtg ttt ggc agc ggg acc cag ctc acc gtt tta agt cag ccc aag gcc        454
Val Phe Gly Ser Gly Thr Gln Leu Thr Val Leu Ser Gln Pro Lys Ala
            100                 105                 110 acc ccc tcg gtc act ctg ttc ccg ccg tcc tct gag gag ctc caa gcc        502
Thr Pro Ser Val Thr Leu Phe Pro Pro Ser Ser Glu Glu Leu Gln Ala
        115                 120                 125 aac aag gct aca ctg gtg tgt ctc atg aat gac ttt tat ccg gga atc        550
Asn Lys Ala Thr Leu Val Cys Leu Met Asn Asp Phe Tyr Pro Gly Ile
    130                 135                 140 ttg acg gtg acc tgg aag gca gat ggt acc ccc atc acc cag ggc gtg        598
Leu Thr Val Thr Trp Lys Ala Asp Gly Thr Pro Ile Thr Gln Gly Val
145                 150                 155                 160
```

```
gag atg acc acg ccc tcc aaa cag agc aac aac aag tac gcg gcc agc      646
Glu Met Thr Thr Pro Ser Lys Gln Ser Asn Asn Lys Tyr Ala Ala Ser
        165                 170                 175 agc tac ctg agc ctg acg ccc gag cag tgg agg tcc cgc aga agc tac      694
Ser Tyr Leu Ser Leu Thr Pro Glu Gln Trp Arg Ser Arg Arg Ser Tyr
    180                 185                 190 agc tgc cag gtc atg cac gaa ggg agc acc gtg gag aag acg gtg gcc      742
Ser Cys Gln Val Met His Glu Gly Ser Thr Val Glu Lys Thr Val Ala
195                 200                 205 cct gca gaa tgt tca tag gttcccagcc ccgaccccac ccaaggggc              790
Pro Ala Glu Cys Ser
    210 ctggagctgc aggatcccag gggaagggtc tctctctgca tcccaagcca tccagccctt    850 ctccctgtac ccagtaaacc ctaaataaat accctctttg tcaaccagaa a             901

<210> SEQ ID NO 2
<211> LENGTH: 213
<212> TYPE: PRT
<213> ORGANISM: Homo sapiens

<400> SEQUENCE: 2

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly Leu Ala
            20                  25                  30

Val Val Thr His Gly Leu Leu Arg Pro Thr Ala Ala Ser Gln Ser Arg
        35                  40                  45

Ala Leu Gly Pro Gly Ala Pro Gly Gly Ser Ser Arg Ser Ser Leu Arg
    50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
        115                 120                 125

Asn Lys Ala Thr Leu Val Cys Leu Met Asn Asp Phe Tyr Pro Gly Ile
    130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
    210

<210> SEQ ID NO 3
<211> LENGTH: 176
<212> TYPE: PRT
<213> ORGANISM: Homo sapiens

<400> SEQUENCE: 3

Leu Leu Arg Pro Thr Ala Ala Ser Gln Ser Arg Ala Leu Gly Pro Gly
```

```
              1               5              10              15
            Ala Pro Gly Gly Ser Ser Arg Ser Ser Leu Arg Ser Arg Trp Gly Arg
                            20                  25                  30
            Phe Leu Leu Gln Arg Gly Ser Trp Thr Gly Pro Arg Cys Trp Pro Arg
                            35                  40                  45
            Gly Phe Gln Ser Lys His Asn Ser Val Thr His Val Phe Gly Ser Gly
                    50                  55                  60
            Thr Gln Leu Thr Val Leu Ser Gln Pro Lys Ala Thr Pro Ser Val Thr
             65                  70                  75                  80
            Leu Phe Pro Pro Ser Ser Glu Glu Leu Gln Ala Asn Lys Ala Thr Leu
                            85                  90                  95
            Val Cys Leu Met Asn Asp Phe Tyr Pro Gly Ile Leu Thr Val Thr Trp
                        100                 105                 110
            Lys Ala Asp Gly Thr Pro Ile Thr Gln Gly Val Glu Met Thr Thr Pro
                        115                 120                 125
            Ser Lys Gln Ser Asn Asn Lys Tyr Ala Ala Ser Ser Tyr Leu Ser Leu
                    130                 135                 140
            Thr Pro Glu Gln Trp Arg Ser Arg Arg Ser Tyr Ser Cys Gln Val Met
            145                 150                 155                 160
            His Glu Gly Ser Thr Val Glu Lys Thr Val Ala Pro Ala Glu Cys Ser
                            165                 170                 175

<210> SEQ ID NO 4
<211> LENGTH: 513
<212> TYPE: DNA
<213> ORGANISM: Canis familiaris
<220> FEATURE:
<221> NAME/KEY: CDS
<222> LOCATION: (2)..(364)
<223> OTHER INFORMATION:

<400> SEQUENCE: 4 c agg gct cct ctt ttc ggc gga ggc acc cac ctg acc gtc ctc ggt cag        49
  Arg Ala Pro Leu Phe Gly Gly Gly Thr His Leu Thr Val Leu Gly Gln
    1               5                  10                  15 ccc aag gcc tcc ccc tcg gtc aca ctc ttc ccg ccc tcc tct gag gag          97
Pro Lys Ala Ser Pro Ser Val Thr Leu Phe Pro Pro Ser Ser Glu Glu
                20                  25                  30 ctc ggc gcc aac aag gcc acc ctg gtg tgc ctc atc agc gac ttc tac         145
Leu Gly Ala Asn Lys Ala Thr Leu Val Cys Leu Ile Ser Asp Phe Tyr
            35                  40                  45 ccc agc ggc gtg acg gtg gcc tgg aag gca gac ggc agc ccc gtc acc         193
Pro Ser Gly Val Thr Val Ala Trp Lys Ala Asp Gly Ser Pro Val Thr
        50                  55                  60 cag ggc gtg gag acc acc aag ccc tcc aag cag agc aac aac aag tac         241
Gln Gly Val Glu Thr Thr Lys Pro Ser Lys Gln Ser Asn Asn Lys Tyr
 65                  70                  75                  80 gcg gcc agc agc tac ctg agc ctg acg cct gac aag tgg aaa tct cac         289
Ala Ala Ser Ser Tyr Leu Ser Leu Thr Pro Asp Lys Trp Lys Ser His
                85                  90                  95 agc agc ttc agc tgc ctg gtc acg cac gag ggg agc acc gtg gag aag         337
Ser Ser Phe Ser Cys Leu Val Thr His Glu Gly Ser Thr Val Glu Lys
            100                 105                 110 aag gtg gcc ccc gca gag tgc tct tag gttcccgacg gccccgccca              384
Lys Val Ala Pro Ala Glu Cys Ser
        115                 120 ccgaagggggg cccggagcct caggacctcc aggaggatct tgcctcccat ctgggtcatc       444
ccgcccttct ccccgcaccc aggcagcact caataaagtg ttctttgttc aatcagaaaa       504
``` aaaaaaaaa                                                                         513

<210> SEQ ID NO 5
<211> LENGTH: 120
<212> TYPE: PRT
<213> ORGANISM: Canis familiaris

<400> SEQUENCE: 5

Arg Ala Pro Leu Phe Gly Gly Gly Thr His Leu Thr Val Leu Gly Gln
1               5                   10                  15

Pro Lys Ala Ser Pro Ser Val Thr Leu Phe Pro Pro Ser Ser Glu Glu
            20                  25                  30

Leu Gly Ala Asn Lys Ala Thr Leu Val Cys Leu Ile Ser Asp Phe Tyr
        35                  40                  45

Pro Ser Gly Val Thr Val Ala Trp Lys Ala Asp Gly Ser Pro Val Thr
    50                  55                  60

Gln Gly Val Glu Thr Thr Lys Pro Ser Lys Gln Ser Asn Asn Lys Tyr
65                  70                  75                  80

Ala Ala Ser Ser Tyr Leu Ser Leu Thr Pro Asp Lys Trp Lys Ser His
                85                  90                  95

Ser Ser Phe Ser Cys Leu Val Thr His Glu Gly Ser Thr Val Glu Lys
            100                 105                 110

Lys Val Ala Pro Ala Glu Cys Ser
        115                 120

<210> SEQ ID NO 6
<211> LENGTH: 659
<212> TYPE: DNA
<213> ORGANISM: Canis familiaris
<220> FEATURE:
<221> NAME/KEY: CDS
<222> LOCATION: (2)..(484)
<223> OTHER INFORMATION:

<400> SEQUENCE: 6 c tcg ggg gtc ccg gat cga ttc tct acc tcc agg tca ggc tac aca gcc        49
  Ser Gly Val Pro Asp Arg Phe Ser Thr Ser Arg Ser Gly Tyr Thr Ala
  1               5                   10                  15 acc ctg acc atc tct ggg ctc cag gct gag gac gaa ggt gat tat tac         97
Thr Leu Thr Ile Ser Gly Leu Gln Ala Glu Asp Glu Gly Asp Tyr Tyr
            20                  25                  30 tgc tca aca tgg gac aac gat ctc aaa ggc agt gtt ttc ggc ggg ggc        145
Cys Ser Thr Trp Asp Asn Asp Leu Lys Gly Ser Val Phe Gly Gly Gly
        35                  40                  45 acc cat ctg acc gtc ctc ggt cag ccc aag gcc tcc ccc tcg gtc aca        193
Thr His Leu Thr Val Leu Gly Gln Pro Lys Ala Ser Pro Ser Val Thr
    50                  55                  60 ctc ttc ccg ccc tcc tct gag gaa ctc ggc gcc aac aag gcc acc ctg        241
Leu Phe Pro Pro Ser Ser Glu Glu Leu Gly Ala Asn Lys Ala Thr Leu
65                  70                  75                  80 gtg tgc ctc atc agc gac ttc tac ccc agt ggc gtg acg gtg gcc tgg        289
Val Cys Leu Ile Ser Asp Phe Tyr Pro Ser Gly Val Thr Val Ala Trp
                85                  90                  95 aag gca gac ggc agc ccc gtc acc cag ggc gtg gag acc acc aag ccc        337
Lys Ala Asp Gly Ser Pro Val Thr Gln Gly Val Glu Thr Thr Lys Pro
            100                 105                 110 tcc aag cag agc aac aac aag tac gcg gcc agc agc tac ctg agc ctg        385
Ser Lys Gln Ser Asn Asn Lys Tyr Ala Ala Ser Ser Tyr Leu Ser Leu
        115                 120                 125

| | |
|---|---|
| acg cct gac aag tgg aaa tct cac agc agc ttc agc tgc ctg gtc aca<br>Thr Pro Asp Lys Trp Lys Ser His Ser Ser Phe Ser Cys Leu Val Thr<br>    130                        135                            140 | 433 |
| cac gag ggg agc acc gtg gag aag aag gtg gcc ccc gca gag tgc tct<br>His Glu Gly Ser Thr Val Glu Lys Lys Val Ala Pro Ala Glu Cys Ser<br>145                        150                        155                    160 | 481 |
| tag gttcccgacg ccccgccca cctaaggggg cccggagcct caggacctcc | 534 |
| aggaggatct tgcctcctat ctgggtcatc ccgcccttct ccccacaccc aggcagcact | 594 |
| caataaagtg ttctttgttc aatctgaaaa aaaaaaaaaa aaaaaaaaaa aaaaaaaaaa | 654 |
| aaaaa | 659 |

<210> SEQ ID NO 7
<211> LENGTH: 160
<212> TYPE: PRT
<213> ORGANISM: Canis familiaris

<400> SEQUENCE: 7

Ser Gly Val Pro Asp Arg Phe Ser Thr Ser Arg Ser Gly Tyr Thr Ala
1               5                   10                  15

Thr Leu Thr Ile Ser Gly Leu Gln Ala Glu Asp Glu Gly Asp Tyr Tyr
            20                  25                  30

Cys Ser Thr Trp Asp Asn Asp Leu Lys Gly Ser Val Phe Gly Gly Gly
        35                  40                  45

Thr His Leu Thr Val Leu Gly Gln Pro Lys Ala Ser Pro Ser Val Thr
    50                  55                  60

Leu Phe Pro Pro Ser Ser Glu Glu Leu Gly Ala Asn Lys Ala Thr Leu
65                  70                  75                  80

Val Cys Leu Ile Ser Asp Phe Tyr Pro Ser Gly Val Thr Val Ala Trp
                85                  90                  95

Lys Ala Asp Gly Ser Pro Val Thr Gln Gly Val Glu Thr Thr Lys Pro
            100                 105                 110

Ser Lys Gln Ser Asn Asn Lys Tyr Ala Ala Ser Ser Tyr Leu Ser Leu
        115                 120                 125

Thr Pro Asp Lys Trp Lys Ser His Ser Ser Phe Ser Cys Leu Val Thr
    130                 135                 140

His Glu Gly Ser Thr Val Glu Lys Lys Val Ala Pro Ala Glu Cys Ser
145                 150                 155                 160

<210> SEQ ID NO 8
<211> LENGTH: 634
<212> TYPE: DNA
<213> ORGANISM: Canis familiaris
<220> FEATURE:
<221> NAME/KEY: CDS
<222> LOCATION: (2)..(496)
<223> OTHER INFORMATION:

<400> SEQUENCE: 8

| | |
|---|---|
| g gac act gaa cgg ccc tct ggg atc cct gac cgc ttc tct ggc tcc agt<br>  Asp Thr Glu Arg Pro Ser Gly Ile Pro Asp Arg Phe Ser Gly Ser Ser<br>  1                  5                    10                    15 | 49 |
| tca ggg aac aca cac acc ctg acc atc aga ggg gct cgg gcc gag gac<br>Ser Gly Asn Thr His Thr Leu Thr Ile Arg Gly Ala Arg Ala Glu Asp<br>          20                        25                        30 | 97 |
| gag gct gac tat tac tgc gag tca gca gtc agt act gat atc ggc gtg<br>Glu Ala Asp Tyr Tyr Cys Glu Ser Ala Val Ser Thr Asp Ile Gly Val<br>              35                      40                        45 | 145 |
| ttc ggc gga ggc acc cac ctg acc gtc ctc ggt cag ccc agg gcc tcc | 193 |

```
                                                      -continued

Phe Gly Gly Gly Thr His Leu Thr Val Leu Gly Gln Pro Arg Ala Ser
    50                  55                  60 ccc tcg gtc aca ctc ttc ccg ccc tcc tct gag gag ctc ggc gcc aac      241
Pro Ser Val Thr Leu Phe Pro Pro Ser Ser Glu Glu Leu Gly Ala Asn
65                  70                  75                  80 aag gcc acc ctg gtg tgc ctc atc agc gac ttc tac ccc agc ggt gtg      289
Lys Ala Thr Leu Val Cys Leu Ile Ser Asp Phe Tyr Pro Ser Gly Val
                85                  90                  95 acg gtg gcc tgg aag gca gac ggc agc ccc gtc acc cag ggc gtg gag      337
Thr Val Ala Trp Lys Ala Asp Gly Ser Pro Val Thr Gln Gly Val Glu
            100                 105                 110 acc acc aag ccc tcc aag cag agc aac aac aag tac gcg gcc agc agc      385
Thr Thr Lys Pro Ser Lys Gln Ser Asn Asn Lys Tyr Ala Ala Ser Ser
        115                 120                 125 tac ctg agc ctg acg cct gac aag tgg aaa tct cac agc agc ttc agc      433
Tyr Leu Ser Leu Thr Pro Asp Lys Trp Lys Ser His Ser Ser Phe Ser
    130                 135                 140 tgc ctg gtc acg cac gag ggg agc acc gtg gag aag aag gtg gcc ccc      481
Cys Leu Val Thr His Glu Gly Ser Thr Val Glu Lys Lys Val Ala Pro
145                 150                 155                 160 gca gag tgc tct tag gttcccgacg gccccgccca ccgaagggg  cccggagcct      536
Ala Glu Cys Ser caggacctcc aggaggatct tgcctcccat ctgggtcatc ccgctcttct ccccgcaccc    596
aggcagcact caataaagtg ttctttgttc aatcaaaa                            634

<210> SEQ ID NO 9
<211> LENGTH: 164
<212> TYPE: PRT
<213> ORGANISM: Canis familiaris

<400> SEQUENCE: 9

Asp Thr Glu Arg Pro Ser Gly Ile Pro Asp Arg Phe Ser Gly Ser Ser
1               5                   10                  15

Ser Gly Asn Thr His Thr Leu Thr Ile Arg Gly Ala Arg Ala Glu Asp
            20                  25                  30

Glu Ala Asp Tyr Tyr Cys Glu Ser Ala Val Ser Thr Asp Ile Gly Val
        35                  40                  45

Phe Gly Gly Gly Thr His Leu Thr Val Leu Gly Gln Pro Arg Ala Ser
    50                  55                  60

Pro Ser Val Thr Leu Phe Pro Pro Ser Ser Glu Glu Leu Gly Ala Asn
65                  70                  75                  80

Lys Ala Thr Leu Val Cys Leu Ile Ser Asp Phe Tyr Pro Ser Gly Val
                85                  90                  95

Thr Val Ala Trp Lys Ala Asp Gly Ser Pro Val Thr Gln Gly Val Glu
            100                 105                 110

Thr Thr Lys Pro Ser Lys Gln Ser Asn Asn Lys Tyr Ala Ala Ser Ser
        115                 120                 125

Tyr Leu Ser Leu Thr Pro Asp Lys Trp Lys Ser His Ser Ser Phe Ser
    130                 135                 140

Cys Leu Val Thr His Glu Gly Ser Thr Val Glu Lys Lys Val Ala Pro
145                 150                 155                 160

Ala Glu Cys Ser

<210> SEQ ID NO 10
<211> LENGTH: 635
<212> TYPE: DNA
<213> ORGANISM: Canis familiaris
```

<220> FEATURE:
<221> NAME/KEY: CDS
<222> LOCATION: (2)..(490)
<223> OTHER INFORMATION:

<400> SEQUENCE: 10

```
c cga cct gca ggg gta ccc gat cga ttc tct ggg tcc aag tca ggc ggg        49
  Arg Pro Ala Gly Val Pro Asp Arg Phe Ser Gly Ser Lys Ser Gly Gly
  1               5                   10                  15 tca gcc atc ctg acc atc tct ggg ctc cag cct gag gac gaa tgt gat          97
Ser Ala Ile Leu Thr Ile Ser Gly Leu Gln Pro Glu Asp Glu Cys Asp
                20                  25                  30 tat tac tgt tcg tct tgg gat aag ggt ctc agc agg tcc gtg ttc ggc         145
Tyr Tyr Cys Ser Ser Trp Asp Lys Gly Leu Ser Arg Ser Val Phe Gly
            35                  40                  45 gga ggc acc cac ctg acc gtc ctc ggt cag ccc aag gcc tcc ccc tcg         193
Gly Gly Thr His Leu Thr Val Leu Gly Gln Pro Lys Ala Ser Pro Ser
        50                  55                  60 gtc aca ctc ttc ccg ccc tcc tct gag gag ctc ggc gcc aac aag gcc         241
Val Thr Leu Phe Pro Pro Ser Ser Glu Glu Leu Gly Ala Asn Lys Ala
65                  70                  75                  80 acc ctg gtg tgc ctc atc agc gac ttc tac ccc agc ggc gtg acg gtg         289
Thr Leu Val Cys Leu Ile Ser Asp Phe Tyr Pro Ser Gly Val Thr Val
                85                  90                  95 gcc tgg aag gca gac ggc agc ccc gtc acc cag ggc gtg gag acc acc         337
Ala Trp Lys Ala Asp Gly Ser Pro Val Thr Gln Gly Val Glu Thr Thr
                100                 105                 110 aag ccc tcc aag cag agc aac aac aag tac gcg gcc agc agc tac ctg         385
Lys Pro Ser Lys Gln Ser Asn Asn Lys Tyr Ala Ala Ser Ser Tyr Leu
            115                 120                 125 agc ctg acg cct gac aag tgg aaa tct cac agc agc ttc agc tgc ctg         433
Ser Leu Thr Pro Asp Lys Trp Lys Ser His Ser Ser Phe Ser Cys Leu
        130                 135                 140 gtc acg cac gag ggg agc acc gtg gag aag aag gtg gcc ccc gca gag         481
Val Thr His Glu Gly Ser Thr Val Glu Lys Lys Val Ala Pro Ala Glu
145                 150                 155                 160 tgc tct tag gttcccgacg gccccgccca ccgaagggggg cccggagcct               530
Cys Ser caggacctcc aggaggatct tgcctcccat ctgggtcatc ccgcccttct ccccgcaccc       590
aggcagcact caataaagtg ttctttgttc aatcagaaaa aaaaa                      635
```

<210> SEQ ID NO 11
<211> LENGTH: 162
<212> TYPE: PRT
<213> ORGANISM: Canis familiaris

<400> SEQUENCE: 11

```
Arg Pro Ala Gly Val Pro Asp Arg Phe Ser Gly Ser Lys Ser Gly Gly
1               5                   10                  15

Ser Ala Ile Leu Thr Ile Ser Gly Leu Gln Pro Glu Asp Glu Cys Asp
                20                  25                  30

Tyr Tyr Cys Ser Ser Trp Asp Lys Gly Leu Ser Arg Ser Val Phe Gly
            35                  40                  45

Gly Gly Thr His Leu Thr Val Leu Gly Gln Pro Lys Ala Ser Pro Ser
        50                  55                  60

Val Thr Leu Phe Pro Pro Ser Ser Glu Glu Leu Gly Ala Asn Lys Ala
65                  70                  75                  80

Thr Leu Val Cys Leu Ile Ser Asp Phe Tyr Pro Ser Gly Val Thr Val
                85                  90                  95
```

```
Ala Trp Lys Ala Asp Gly Ser Pro Val Thr Gln Gly Val Glu Thr Thr
            100                 105                 110

Lys Pro Ser Lys Gln Ser Asn Asn Lys Tyr Ala Ala Ser Ser Tyr Leu
        115                 120                 125

Ser Leu Thr Pro Asp Lys Trp Lys Ser His Ser Ser Phe Ser Cys Leu
    130                 135                 140

Val Thr His Glu Gly Ser Thr Val Glu Lys Lys Val Ala Pro Ala Glu
145                 150                 155                 160

Cys Ser

<210> SEQ ID NO 12
<211> LENGTH: 583
<212> TYPE: DNA
<213> ORGANISM: Canis familiaris
<220> FEATURE:
<221> NAME/KEY: CDS
<222> LOCATION: (2)..(445)
<223> OTHER INFORMATION:

<400> SEQUENCE: 12 c aaa gcc gcc ctc acc atc aca gga gcc cag cct gag gac gag gct gac        49
  Lys Ala Ala Leu Thr Ile Thr Gly Ala Gln Pro Glu Asp Glu Ala Asp
  1               5                   10                  15 tac tac tgt gct ctg gga tta agt agt agt agt agc cat agt gtg ttc          97
Tyr Tyr Cys Ala Leu Gly Leu Ser Ser Ser Ser Ser His Ser Val Phe
            20                  25                  30 ggc gga ggc acc cat ctg acc gtc ctc ggt cag ccc aag gcc tcc ccc          145
Gly Gly Gly Thr His Leu Thr Val Leu Gly Gln Pro Lys Ala Ser Pro
        35                  40                  45 tcg gtc aca ctc ttc ccg ccc tcc tct gag gag ctc ggc gcc aac aag          193
Ser Val Thr Leu Phe Pro Pro Ser Ser Glu Glu Leu Gly Ala Asn Lys
    50                  55                  60 gcc acc ctg gtg tgc ctc atc agc gac ttc tac ccc agt ggc gtg acg          241
Ala Thr Leu Val Cys Leu Ile Ser Asp Phe Tyr Pro Ser Gly Val Thr
65                  70                  75                  80 gtg gcc tgg aag gca gac ggc agc ccc gtc acc cag ggc gtg gag acc          289
Val Ala Trp Lys Ala Asp Gly Ser Pro Val Thr Gln Gly Val Glu Thr
                85                  90                  95 acc aag ccc tcc aag cag agc aac aac aag tac gcg gcc agc agc tac          337
Thr Lys Pro Ser Lys Gln Ser Asn Asn Lys Tyr Ala Ala Ser Ser Tyr
            100                 105                 110 ctg agc ctg acg cct gac aag tgg aaa tct cac agc agc ttc agc tgc          385
Leu Ser Leu Thr Pro Asp Lys Trp Lys Ser His Ser Ser Phe Ser Cys
        115                 120                 125 ctg gtc aca cac gag ggg agc acc gtg gag aag aag gtg gcc ccc gca          433
Leu Val Thr His Glu Gly Ser Thr Val Glu Lys Lys Val Ala Pro Ala
    130                 135                 140 gag tgc tct tag gttcccgacg ccccccgccca cctaaggggg cccggagcct             485
Glu Cys Ser
145 caggacctcc aggaggatct tgcctcctat ctgggtcatc ccgcccttct ccccacaccc        545 aggcagcact caataaagtg ttctttgttc aatcagaa                                583

<210> SEQ ID NO 13
<211> LENGTH: 147
<212> TYPE: PRT
<213> ORGANISM: Canis familiaris

<400> SEQUENCE: 13
```

```
Lys Ala Ala Leu Thr Ile Thr Gly Ala Gln Pro Glu Asp Glu Ala Asp
1               5                   10                  15

Tyr Tyr Cys Ala Leu Gly Leu Ser Ser Ser Ser His Ser Val Phe
            20                  25                  30

Gly Gly Gly Thr His Leu Thr Val Leu Gly Gln Pro Lys Ala Ser Pro
                35                  40                  45

Ser Val Thr Leu Phe Pro Pro Ser Ser Glu Glu Leu Gly Ala Asn Lys
    50                  55                  60

Ala Thr Leu Val Cys Leu Ile Ser Asp Phe Tyr Pro Ser Gly Val Thr
65                  70                  75                  80

Val Ala Trp Lys Ala Asp Gly Ser Pro Val Thr Gln Gly Val Glu Thr
                85                  90                  95

Thr Lys Pro Ser Lys Gln Ser Asn Asn Lys Tyr Ala Ala Ser Ser Tyr
            100                 105                 110

Leu Ser Leu Thr Pro Asp Lys Trp Lys Ser His Ser Ser Phe Ser Cys
        115                 120                 125

Leu Val Thr His Glu Gly Ser Thr Val Glu Lys Lys Val Ala Pro Ala
    130                 135                 140

Glu Cys Ser
145
```

<210> SEQ ID NO 14
<211> LENGTH: 796
<212> TYPE: DNA
<213> ORGANISM: Canis familiaris
<220> FEATURE:
<221> NAME/KEY: CDS
<222> LOCATION: (2)..(643)
<223> OTHER INFORMATION:

<400> SEQUENCE: 14

```
g ctg act cag ccg gcc tca gtg tct ggg tcc ctg ggc cag agg atc acc        49
  Leu Thr Gln Pro Ala Ser Val Ser Gly Ser Leu Gly Gln Arg Ile Thr
  1               5                   10                  15 atc tcc tgc act gga agc agc tcc aac att gga ggt aat aat gtg ggt        97
Ile Ser Cys Thr Gly Ser Ser Ser Asn Ile Gly Gly Asn Asn Val Gly
            20                  25                  30 tgg tac cag cag ctc cca gga aga ggc ccc aga act gtc atc ttt act       145
Trp Tyr Gln Gln Leu Pro Gly Arg Gly Pro Arg Thr Val Ile Phe Thr
        35                  40                  45 aca cat agt cga ccc tcg ggg gtg tcc gat cga ttc tct gcc tcc aag       193
Thr His Ser Arg Pro Ser Gly Val Ser Asp Arg Phe Ser Ala Ser Lys
    50                  55                  60 tct ggc agc aca gcc acc ctg acc atc tct ggg ctc cag gct gag gat       241
Ser Gly Ser Thr Ala Thr Leu Thr Ile Ser Gly Leu Gln Ala Glu Asp
65                  70                  75                  80 gag gct gat tat tac tgc tca acg tgg gat gat agt ctc agt gct gct       289
Glu Ala Asp Tyr Tyr Cys Ser Thr Trp Asp Asp Ser Leu Ser Ala Ala
                85                  90                  95 gtg ttc ggc gga ggc acc cac ctg acc gtc ctc ggt cag ccc aag gcc       337
Val Phe Gly Gly Gly Thr His Leu Thr Val Leu Gly Gln Pro Lys Ala
            100                 105                 110 tcc ccc tcg gtc aca ctc ttc ccg ccc tcc tct gag gag ctc ggc gcc       385
Ser Pro Ser Val Thr Leu Phe Pro Pro Ser Ser Glu Glu Leu Gly Ala
        115                 120                 125 aac aag gcc acc ctg gtg tgc ctc atc agc gac ttc tac ccc agc ggc       433
Asn Lys Ala Thr Leu Val Cys Leu Ile Ser Asp Phe Tyr Pro Ser Gly
    130                 135                 140 gtg acg gtg gcc tgg aag gca gac ggc agc ccc gtc acc cag ggc gtg       481
Val Thr Val Ala Trp Lys Ala Asp Gly Ser Pro Val Thr Gln Gly Val
```

```
Val Thr Val Ala Trp Lys Ala Asp Gly Ser Pro Val Thr Gln Gly Val
145                 150                 155                 160 gag acc acc aag ccc tcc aag cag agc aac aac aag tac gcg gcc agc      529
Glu Thr Thr Lys Pro Ser Lys Gln Ser Asn Asn Lys Tyr Ala Ala Ser
                165                 170                 175 agc tac ctg agc ctg acg cct gac aag tgg aaa tct cac agc agc ttc      577
Ser Tyr Leu Ser Leu Thr Pro Asp Lys Trp Lys Ser His Ser Ser Phe
        180                 185                 190 agc tgc ctg gtc acg cac gag ggg agc acc gtg gag aag aag gtg gcc      625
Ser Cys Leu Val Thr His Glu Gly Ser Thr Val Glu Lys Lys Val Ala
195                 200                 205 ccc gca gag tgc tct tag gttcccgacg ccccgcccca ccgaaggggg             673
Pro Ala Glu Cys Ser
    210 cccggagcct caggacctcc aggaggatct tgcctcccat ctgggtcatc ccgcccttct    733 ccccgcaccc aggcagcact caataaagtg ttctttgttc aatcaaaaaa aaaaaaaaaa    793 aaa                                                                  796

<210> SEQ ID NO 15
<211> LENGTH: 213
<212> TYPE: PRT
<213> ORGANISM: Canis familiaris

<400> SEQUENCE: 15

Leu Thr Gln Pro Ala Ser Val Ser Gly Ser Leu Gly Gln Arg Ile Thr
1               5                   10                  15

Ile Ser Cys Thr Gly Ser Ser Asn Ile Gly Gly Asn Asn Val Gly
            20                  25                  30

Trp Tyr Gln Gln Leu Pro Gly Arg Gly Pro Arg Thr Val Ile Phe Thr
        35                  40                  45

Thr His Ser Arg Pro Ser Gly Val Ser Asp Arg Phe Ser Ala Ser Lys
    50                  55                  60

Ser Gly Ser Thr Ala Thr Leu Thr Ile Ser Gly Leu Gln Ala Glu Asp
65                  70                  75                  80

Glu Ala Asp Tyr Tyr Cys Ser Thr Trp Asp Asp Ser Leu Ser Ala Ala
                85                  90                  95

Val Phe Gly Gly Gly Thr His Leu Thr Val Leu Gly Gln Pro Lys Ala
            100                 105                 110

Ser Pro Ser Val Thr Leu Phe Pro Pro Ser Ser Glu Glu Leu Gly Ala
        115                 120                 125

Asn Lys Ala Thr Leu Val Cys Leu Ile Ser Asp Phe Tyr Pro Ser Gly
    130                 135                 140

Val Thr Val Ala Trp Lys Ala Asp Gly Ser Pro Val Thr Gln Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Asp Lys Trp Lys Ser His Ser Ser Phe
            180                 185                 190

Ser Cys Leu Val Thr His Glu Gly Ser Thr Val Glu Lys Lys Val Ala
        195                 200                 205

Pro Ala Glu Cys Ser
    210

<210> SEQ ID NO 16
<211> LENGTH: 1306
<212> TYPE: DNA
```

<213> ORGANISM: Canis familiaris
<220> FEATURE:
<221> NAME/KEY: CDS
<222> LOCATION: (2)..(646)
<223> OTHER INFORMATION:

<400> SEQUENCE: 16

```
c tcc tat gtg ctg aca cag ctg cca tcc atg act gtg acc ctg aag cag      49
  Ser Tyr Val Leu Thr Gln Leu Pro Ser Met Thr Val Thr Leu Lys Gln
  1               5                   10                  15 acg gcc cgc atc acc tgt gag gga gac agc att gga agc aaa aga gtt       97
Thr Ala Arg Ile Thr Cys Glu Gly Asp Ser Ile Gly Ser Lys Arg Val
                20                  25                  30 tac tgg tac caa cag aac ctg ggc cag gtc cct cta ctg att atc tat      145
Tyr Trp Tyr Gln Gln Asn Leu Gly Gln Val Pro Leu Leu Ile Ile Tyr
            35                  40                  45 gat gat gcc acc agg ccg tca agg atc cct gac cga ttc tcc ggc gcc      193
Asp Asp Ala Thr Arg Pro Ser Arg Ile Pro Asp Arg Phe Ser Gly Ala
        50                  55                  60 aac tcg ggg gac aca gcc acc ctg acc atc agc ggg gcc ctg gcc gag      241
Asn Ser Gly Asp Thr Ala Thr Leu Thr Ile Ser Gly Ala Leu Ala Glu
65                  70                  75                  80 gac gag gct gac tat tac tgt cag gtg tgg gac agt gat agt aag act      289
Asp Glu Ala Asp Tyr Tyr Cys Gln Val Trp Asp Ser Asp Ser Lys Thr
                85                  90                  95 ggt gta ttc ggc gga ggc acc cac ctg acc gtc ctc ggt cag ccc aag      337
Gly Val Phe Gly Gly Gly Thr His Leu Thr Val Leu Gly Gln Pro Lys
            100                 105                 110 gcc tcc ccc tcg gtc aca ctc ttc ccg ccc tcc tct gag gag ctc ggc      385
Ala Ser Pro Ser Val Thr Leu Phe Pro Pro Ser Ser Glu Glu Leu Gly
        115                 120                 125 gcc aac aag gcc acc ctg gtg tgc ctc atc agc gac ttc tac ccc agc      433
Ala Asn Lys Ala Thr Leu Val Cys Leu Ile Ser Asp Phe Tyr Pro Ser
    130                 135                 140 ggt gtg acg gtg gcc tgg aag gca gac ggc agc ccc gtc acc cag ggc      481
Gly Val Thr Val Ala Trp Lys Ala Asp Gly Ser Pro Val Thr Gln Gly
145                 150                 155                 160 gtg gag acc acc aag ccc tcc aag cag agc aac aac aag tac gcg gcc      529
Val Glu Thr Thr Lys Pro Ser Lys Gln Ser Asn Asn Lys Tyr Ala Ala
                165                 170                 175 agc agc tac ctg agc ctg acg cct gac aag tgg aaa tct cac agc agc      577
Ser Ser Tyr Leu Ser Leu Thr Pro Asp Lys Trp Lys Ser His Ser Ser
            180                 185                 190 ttc agc tgc ctg gtc acg cac gag ggg agc acc gtg gag aag aag gtg      625
Phe Ser Cys Leu Val Thr His Glu Gly Ser Thr Val Glu Lys Lys Val
        195                 200                 205 gcc ccc gca gag tgc tct tag gttcccgacg ccccgcccca ccgaagggg          676
Ala Pro Ala Glu Cys Ser
    210 cccggagcct caggacctcc aggaggatct tgcctcccat ctgggtcatc ccgctcttct    736 ccccgcaccc aggcagcact caataaagtg ttctttgttc aatcagaaaa aaaaaaaaaa    796 aaaaaactcg agccggctgg agtctgggat gcagaacatg agcatccata cgaagacgac    856 cagcggctac tccggtggcc tgaacttggc ctacgggggc ctcacgagcc ccggcctcaa    916 ctacggccag agctccttcc agtccggctt tggccctggc ggttccttca gccgcagcag    976 ctcctccaag gccgtggttg tgaagaagat cgagactcgc gatgggaagc tggtgtctga   1036 gtcgtctgac gtcctgccca agtgaacgga cagcgcgggc cccccagcc tccttgctct   1096 tgtggcccca tgaagccttc ggggaagga gctgtgcagg ggagcctcgc gtacgagaga    1156
```

```
cccgcctaag gctcagcccc ggtccccagc ctaccctag ggggagtcta ctgccctggg    1216 tacccttct tgtccgtgcc cccgaccgaa agccaattca agtgtctttt cccaaataaa    1276
gccgctgcca gtcccaaaaa aaaaaaaaaa                                    1306
```

<210> SEQ ID NO 17
<211> LENGTH: 214
<212> TYPE: PRT
<213> ORGANISM: Canis familiaris

<400> SEQUENCE: 17

```
Ser Tyr Val Leu Thr Gln Leu Pro Ser Met Thr Val Thr Leu Lys Gln
1               5                   10                  15

Thr Ala Arg Ile Thr Cys Glu Gly Asp Ser Ile Gly Ser Lys Arg Val
            20                  25                  30

Tyr Trp Tyr Gln Gln Asn Leu Gly Gln Val Pro Leu Leu Ile Ile Tyr
        35                  40                  45

Asp Asp Ala Thr Arg Pro Ser Arg Ile Pro Asp Arg Phe Ser Gly Ala
    50                  55                  60

Asn Ser Gly Asp Thr Ala Thr Leu Thr Ile Ser Gly Ala Leu Ala Glu
65                  70                  75                  80

Asp Glu Ala Asp Tyr Tyr Cys Gln Val Trp Asp Ser Asp Ser Lys Thr
                85                  90                  95

Gly Val Phe Gly Gly Gly Thr His Leu Thr Val Leu Gly Gln Pro Lys
            100                 105                 110

Ala Ser Pro Ser Val Thr Leu Phe Pro Pro Ser Ser Glu Glu Leu Gly
        115                 120                 125

Ala Asn Lys Ala Thr Leu Val Cys Leu Ile Ser Asp Phe Tyr Pro Ser
    130                 135                 140

Gly Val Thr Val Ala Trp Lys Ala Asp Gly Ser Pro Val Thr Gln Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Asp Lys Trp Lys Ser His Ser Ser
            180                 185                 190

Phe Ser Cys Leu Val Thr His Glu Gly Ser Thr Val Glu Lys Lys Val
        195                 200                 205

Ala Pro Ala Glu Cys Ser
    210
```

<210> SEQ ID NO 18
<211> LENGTH: 859
<212> TYPE: DNA
<213> ORGANISM: Canis familiaris
<220> FEATURE:
<221> NAME/KEY: CDS
<222> LOCATION: (2)..(718)
<223> OTHER INFORMATION:

<400> SEQUENCE: 18

```
g acc tcc aac atg gcc tgg tcc cct ctc ctc ctc aca ctc ctt gct tcc    49
  Thr Ser Asn Met Ala Trp Ser Pro Leu Leu Leu Thr Leu Leu Ala Ser
  1               5                   10                  15 tgc aca gga tcc tgg gcc cag tct gtg cta act cag ccg acc tcg gtg      97
Cys Thr Gly Ser Trp Ala Gln Ser Val Leu Thr Gln Pro Thr Ser Val
            20                  25                  30 tcg ggg tcc ctt ggc cag agg gtc acc atc tcc tgc tct ggc agc tcg     145
Ser Gly Ser Leu Gly Gln Arg Val Thr Ile Ser Cys Ser Gly Ser Ser
```

```
                    35                  40                  45
acc aac atc ggt tct gtt ggt gcg act tgg tac caa cac ctc cca gga        193
Thr Asn Ile Gly Ser Val Gly Ala Thr Trp Tyr Gln His Leu Pro Gly
         50                  55                  60 aag gcc cct aga ctc ctc ctc tac aca cat ggg gaa cgg ccg tca ggg        241
Lys Ala Pro Arg Leu Leu Leu Tyr Thr His Gly Glu Arg Pro Ser Gly
 65                  70                  75                  80 atc cct gac cgg ttt tcc ggc tcc gag tct gcc aac tcg gac acc ctg        289
Ile Pro Asp Arg Phe Ser Gly Ser Glu Ser Ala Asn Ser Asp Thr Leu
                 85                  90                  95 acc atc act gga ctt cag gct gag gac gag gct gat tac tac tgc cag        337
Thr Ile Thr Gly Leu Gln Ala Glu Asp Glu Ala Asp Tyr Tyr Cys Gln
            100                 105                 110 tcc ttt gat agc acg ctt gag act gct gtg ttc ggc ggc ggc act cac        385
Ser Phe Asp Ser Thr Leu Glu Thr Ala Val Phe Gly Gly Gly Thr His
        115                 120                 125 ctg acc gtc ctt ggt cag ccc aag gcc tcc ccc tcg gtc aca ctc ttc        433
Leu Thr Val Leu Gly Gln Pro Lys Ala Ser Pro Ser Val Thr Leu Phe
    130                 135                 140 ccg ccc tcc tct gag gag ctc ggc gcc aac aag gcc acc ctg gtg tgc        481
Pro Pro Ser Ser Glu Glu Leu Gly Ala Asn Lys Ala Thr Leu Val Cys
145                 150                 155                 160 ctc atc agc gac ttc tac ccc agc ggc gtg acg gtg gcc tgg aag gca        529
Leu Ile Ser Asp Phe Tyr Pro Ser Gly Val Thr Val Ala Trp Lys Ala
                165                 170                 175 gac ggc agc ccc gtc acc cag ggc gtg gag acc acc aag ccc tcc aag        577
Asp Gly Ser Pro Val Thr Gln Gly Val Glu Thr Thr Lys Pro Ser Lys
            180                 185                 190 cag agc aac aac aag tac gcg gcc agc agc tac ctg agc ctg acg cct        625
Gln Ser Asn Asn Lys Tyr Ala Ala Ser Ser Tyr Leu Ser Leu Thr Pro
        195                 200                 205 gac aag tgg aaa tct cac agc agc ttc agc tgc ctg gtc acg cac gag        673
Asp Lys Trp Lys Ser His Ser Ser Phe Ser Cys Leu Val Thr His Glu
    210                 215                 220 ggg agc acc gtg gag aag aag gtg gcc ccc gca gag tgc tct tag            718
Gly Ser Thr Val Glu Lys Lys Val Ala Pro Ala Glu Cys Ser
225                 230                 235 gttcccgacg gccccgccca ccgaagggggg cccggagcct caggacctcc aggaggatct    778
tgcctcccat ctgggtcatc ccgctcttct ccccgcaccc aggcagcact caataaagtg    838
ttctttgttc aatcagaaaa a                                              859

<210> SEQ ID NO 19
<211> LENGTH: 238
<212> TYPE: PRT
<213> ORGANISM: Canis familiaris

<400> SEQUENCE: 19

Thr Ser Asn Met Ala Trp Ser Pro Leu Leu Thr Leu Leu Ala Ser
1               5                   10                  15

Cys Thr Gly Ser Trp Ala Gln Ser Val Leu Thr Gln Pro Thr Ser Val
            20                  25                  30

Ser Gly Ser Leu Gly Gln Arg Val Thr Ile Ser Cys Ser Gly Ser Ser
        35                  40                  45

Thr Asn Ile Gly Ser Val Gly Ala Thr Trp Tyr Gln His Leu Pro Gly
    50                  55                  60

Lys Ala Pro Arg Leu Leu Leu Tyr Thr His Gly Glu Arg Pro Ser Gly
 65                 70                  75                  80
```

```
Ile Pro Asp Arg Phe Ser Gly Ser Glu Ser Ala Asn Ser Asp Thr Leu
                 85                  90                  95

Thr Ile Thr Gly Leu Gln Ala Glu Asp Glu Ala Asp Tyr Tyr Cys Gln
            100                 105                 110

Ser Phe Asp Ser Thr Leu Glu Thr Ala Val Phe Gly Gly Gly Thr His
            115                 120                 125

Leu Thr Val Leu Gly Gln Pro Lys Ala Ser Pro Ser Val Thr Leu Phe
130                 135                 140

Pro Pro Ser Ser Glu Glu Leu Gly Ala Asn Lys Ala Thr Leu Val Cys
145                 150                 155                 160

Leu Ile Ser Asp Phe Tyr Pro Ser Gly Val Thr Val Ala Trp Lys Ala
                165                 170                 175

Asp Gly Ser Pro Val Thr Gln Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Asp Lys Trp Lys Ser His Ser Ser Phe Ser Cys Leu Val Thr His Glu
210                 215                 220

Gly Ser Thr Val Glu Lys Lys Val Ala Pro Ala Glu Cys Ser
225                 230                 235

<210> SEQ ID NO 20
<211> LENGTH: 875
<212> TYPE: DNA
<213> ORGANISM: Canis familiaris
<220> FEATURE:
<221> NAME/KEY: CDS
<222> LOCATION: (2)..(715)
<223> OTHER INFORMATION:

<400> SEQUENCE: 20 c tcc aac atg gcc tgg tcc cct ctc ctc ctc aca ctc ctt gtt tac tgc      49
  Ser Asn Met Ala Trp Ser Pro Leu Leu Leu Thr Leu Leu Val Tyr Cys
   1               5                  10                  15 aca ggg tcc tgg gcc cag tct gta ctg act cat ccg acc tca gtg tcg        97
Thr Gly Ser Trp Ala Gln Ser Val Leu Thr His Pro Thr Ser Val Ser
             20                  25                  30 ggg tcc ctt ggc cag agg gtc acc att tcc tgc tcc gga agc acg aac       145
Gly Ser Leu Gly Gln Arg Val Thr Ile Ser Cys Ser Gly Ser Thr Asn
         35                  40                  45 aac atc ggt act gtt ggt gcg ggc tgg tac caa cag ttc cca gga aag       193
Asn Ile Gly Thr Val Gly Ala Gly Trp Tyr Gln Gln Phe Pro Gly Lys
 50                  55                  60 gcc cct aaa ctc ctc att tac agt gat ggg aat cga ccg tca ggg gtc       241
Ala Pro Lys Leu Leu Ile Tyr Ser Asp Gly Asn Arg Pro Ser Gly Val
65                  70                  75                  80 cct gac cgg ttt tcc ggc tcc aag tca ggc aac tca gcc acc ctg acc       289
Pro Asp Arg Phe Ser Gly Ser Lys Ser Gly Asn Ser Ala Thr Leu Thr
                 85                  90                  95 atc att gga ctt cag gct gag gac gag gct gat tac tac tgt cag tct       337
Ile Ile Gly Leu Gln Ala Glu Asp Glu Ala Asp Tyr Tyr Cys Gln Ser
            100                 105                 110 gtt gat ccc acg ctt ggt ggt cat gtg ttc ggc gga ggc acc cat ctg       385
Val Asp Pro Thr Leu Gly Gly His Val Phe Gly Gly Gly Thr His Leu
            115                 120                 125 acc gtc ctc ggt cag ccc aag gcc tcc cct tcg gtc aca ctc ttc ccg       433
Thr Val Leu Gly Gln Pro Lys Ala Ser Pro Ser Val Thr Leu Phe Pro
130                 135                 140 ccc tcc tct gag gag ctt ggc gcc aac aag gcc acc ctg gtg tgc ctc       481
Pro Ser Ser Glu Glu Leu Gly Ala Asn Lys Ala Thr Leu Val Cys Leu
```

```
Pro Ser Ser Glu Glu Leu Gly Ala Asn Lys Ala Thr Leu Val Cys Leu
145                 150                 155                 160 atc agc gac ttc tac ccc agc ggc gtg aca gtg gcc tgg aag gca gac       529
Ile Ser Asp Phe Tyr Pro Ser Gly Val Thr Val Ala Trp Lys Ala Asp
                165                 170                 175 ggc agc ccc atc acc cag ggt gtg gag acc acc aag ccc tcc aag cag       577
Gly Ser Pro Ile Thr Gln Gly Val Glu Thr Thr Lys Pro Ser Lys Gln
            180                 185                 190 agc aac aac aag tac gcg gcc agc agc tac ctg agc ctg acg cct gac       625
Ser Asn Asn Lys Tyr Ala Ala Ser Ser Tyr Leu Ser Leu Thr Pro Asp
        195                 200                 205 aag tgg aaa tct cac agc agc ttc agc tgc ctg gtc acg cac gag ggg       673
Lys Trp Lys Ser His Ser Ser Phe Ser Cys Leu Val Thr His Glu Gly
    210                 215                 220 agc acc gtg gag aag aag gtg gcc ccc gca gag tgc tct tag               715
Ser Thr Val Glu Lys Lys Val Ala Pro Ala Glu Cys Ser
225                 230                 235 gttcctgatg tccccgccc accaaagggg gctcagagcc tcaggacctc caggaggatc      775
ttgcctccca tctgggtcat cccagccttt cccttaaac ccaggcaaca ttcaataaag      835
tgttctttct tcaatcagaa aaaaaaaaaa aaaaaaaaa                            875

<210> SEQ ID NO 21
<211> LENGTH: 237
<212> TYPE: PRT
<213> ORGANISM: Canis familiaris

<400> SEQUENCE: 21

Ser Asn Met Ala Trp Ser Pro Leu Leu Leu Thr Leu Leu Val Tyr Cys
1               5                   10                  15

Thr Gly Ser Trp Ala Gln Ser Val Leu Thr His Pro Thr Ser Val Ser
            20                  25                  30

Gly Ser Leu Gly Gln Arg Val Thr Ile Ser Cys Ser Gly Ser Thr Asn
        35                  40                  45

Asn Ile Gly Thr Val Gly Ala Gly Trp Tyr Gln Gln Phe Pro Gly Lys
    50                  55                  60

Ala Pro Lys Leu Leu Ile Tyr Ser Asp Gly Asn Arg Pro Ser Gly Val
65                  70                  75                  80

Pro Asp Arg Phe Ser Gly Ser Lys Ser Gly Asn Ser Ala Thr Leu Thr
                85                  90                  95

Ile Ile Gly Leu Gln Ala Glu Asp Glu Ala Asp Tyr Tyr Cys Gln Ser
            100                 105                 110

Val Asp Pro Thr Leu Gly Gly His Val Phe Gly Gly Thr His Leu
        115                 120                 125

Thr Val Leu Gly Gln Pro Lys Ala Ser Pro Ser Val Thr Leu Phe Pro
    130                 135                 140

Pro Ser Ser Glu Glu Leu Gly Ala Asn Lys Ala Thr Leu Val Cys Leu
145                 150                 155                 160

Ile Ser Asp Phe Tyr Pro Ser Gly Val Thr Val Ala Trp Lys Ala Asp
                165                 170                 175

Gly Ser Pro Ile Thr Gln Gly Val Glu Thr Thr Lys Pro Ser Lys Gln
            180                 185                 190

Ser Asn Asn Lys Tyr Ala Ala Ser Ser Tyr Leu Ser Leu Thr Pro Asp
        195                 200                 205

Lys Trp Lys Ser His Ser Ser Phe Ser Cys Leu Val Thr His Glu Gly
    210                 215                 220
```

```
Ser Thr Val Glu Lys Lys Val Ala Pro Ala Glu Cys Ser
225                 230                 235

<210> SEQ ID NO 22
<211> LENGTH: 862
<212> TYPE: DNA
<213> ORGANISM: Canis familiaris
<220> FEATURE:
<221> NAME/KEY: CDS
<222> LOCATION: (2)..(721)
<223> OTHER INFORMATION:

<400> SEQUENCE: 22 g atg atc ttc acc atg gcc tgg tcc cct ctc ctc ctc ggc ctc ctt gct        49
  Met Ile Phe Thr Met Ala Trp Ser Pro Leu Leu Leu Gly Leu Leu Ala
  1               5                   10                  15 cac tgc aca ggg tcc tgg gcc cag tct atg ctg act cag ccg gcc tca          97
His Cys Thr Gly Ser Trp Ala Gln Ser Met Leu Thr Gln Pro Ala Ser
                20                  25                  30 gtg tct ggg tcc ctg ggc cag aag gtc acc atc tcc tgc act gga agc         145
Val Ser Gly Ser Leu Gly Gln Lys Val Thr Ile Ser Cys Thr Gly Ser
            35                  40                  45 agc tcc aac atc ggt gct tat tat gtg agc tgg tac caa cag tcc cca         193
Ser Ser Asn Ile Gly Ala Tyr Tyr Val Ser Trp Tyr Gln Gln Ser Pro
50                  55                  60 gga aaa ggc cct aga acc gtc atc tat ggt gat aat tac cga cct tca         241
Gly Lys Gly Pro Arg Thr Val Ile Tyr Gly Asp Asn Tyr Arg Pro Ser
65                  70                  75                  80 ggg gtc ccc gat cga ttc tct ggc tcc aag tca ggc agt tca gcc acc         289
Gly Val Pro Asp Arg Phe Ser Gly Ser Lys Ser Gly Ser Ser Ala Thr
                85                  90                  95 ctg acc atc tct ggg ctc cag gct gag gac gag gct gaa tat tac tgc         337
Leu Thr Ile Ser Gly Leu Gln Ala Glu Asp Glu Ala Glu Tyr Tyr Cys
            100                 105                 110 tta tca tgg gat aat agt ctc aga ggt ggt gtg ttc ggc gga ggc acc         385
Leu Ser Trp Asp Asn Ser Leu Arg Gly Gly Val Phe Gly Gly Gly Thr
        115                 120                 125 cac ctg acc gtc ctc ggt cag ccc aag gcc tcc ccc tcg gtc aca ctc         433
His Leu Thr Val Leu Gly Gln Pro Lys Ala Ser Pro Ser Val Thr Leu
    130                 135                 140 ttc ccg ccc tcc tct gag gag ctc ggc gcc aac aag gcc acc ctg gtg         481
Phe Pro Pro Ser Ser Glu Glu Leu Gly Ala Asn Lys Ala Thr Leu Val
145                 150                 155                 160 tgc ctc atc agc gac ttc tac ccc agc ggt gtg acg gtg gcc tgg aag         529
Cys Leu Ile Ser Asp Phe Tyr Pro Ser Gly Val Thr Val Ala Trp Lys
                165                 170                 175 gca gac ggc agc ccc gtc acc cag ggc gtg gag acc acc aag ccc tcc         577
Ala Asp Gly Ser Pro Val Thr Gln Gly Val Glu Thr Thr Lys Pro Ser
            180                 185                 190 aag cag agc aac aac aag tac gcg gcc agc agc tac ctg agc ctg acg         625
Lys Gln Ser Asn Asn Lys Tyr Ala Ala Ser Ser Tyr Leu Ser Leu Thr
        195                 200                 205 cct gac aag tgg aaa tct cac agc agc ttc agc tgc ctg gtc acg cac         673
Pro Asp Lys Trp Lys Ser His Ser Ser Phe Ser Cys Leu Val Thr His
    210                 215                 220 gag ggg agc acc gtg gag aag aag gtg gcc ccc gca gag tgc tct tag         721
Glu Gly Ser Thr Val Glu Lys Lys Val Ala Pro Ala Glu Cys Ser
225                 230                 235 gttcccgacg ccccgccca ccgaaggggg cccggagcct caggacctcc aggaggatct        781
tgcctcccat ctgggtcatc ccgctcttct ccccgcaccc aggcagcact caataaagtg       841
```

-continued ttctttgttc aatcagaaaa a    862

<210> SEQ ID NO 23
<211> LENGTH: 239
<212> TYPE: PRT
<213> ORGANISM: Canis familiaris

<400> SEQUENCE: 23

Met Ile Phe Thr Met Ala Trp Ser Pro Leu Leu Gly Leu Leu Ala
1               5                   10                  15

His Cys Thr Gly Ser Trp Ala Gln Ser Met Leu Thr Gln Pro Ala Ser
            20                  25                  30

Val Ser Gly Ser Leu Gly Gln Lys Val Thr Ile Ser Cys Thr Gly Ser
        35                  40                  45

Ser Ser Asn Ile Gly Ala Tyr Tyr Val Ser Trp Tyr Gln Gln Ser Pro
    50                  55                  60

Gly Lys Gly Pro Arg Thr Val Ile Tyr Gly Asp Asn Tyr Arg Pro Ser
65                  70                  75                  80

Gly Val Pro Asp Arg Phe Ser Gly Ser Lys Ser Gly Ser Ser Ala Thr
                85                  90                  95

Leu Thr Ile Ser Gly Leu Gln Ala Glu Asp Glu Ala Glu Tyr Tyr Cys
            100                 105                 110

Leu Ser Trp Asp Asn Ser Leu Arg Gly Gly Val Phe Gly Gly Gly Thr
        115                 120                 125

His Leu Thr Val Leu Gly Gln Pro Lys Ala Ser Pro Ser Val Thr Leu
    130                 135                 140

Phe Pro Pro Ser Ser Glu Leu Gly Ala Asn Lys Ala Thr Leu Val
145                 150                 155                 160

Cys Leu Ile Ser Asp Phe Tyr Pro Ser Gly Val Thr Val Ala Trp Lys
                165                 170                 175

Ala Asp Gly Ser Pro Val Thr Gln Gly Val Glu Thr Thr Lys Pro Ser
            180                 185                 190

Lys Gln Ser Asn Asn Lys Tyr Ala Ala Ser Ser Tyr Leu Ser Leu Thr
        195                 200                 205

Pro Asp Lys Trp Lys Ser His Ser Ser Phe Ser Cys Leu Val Thr His
    210                 215                 220

Glu Gly Ser Thr Val Glu Lys Lys Val Ala Pro Ala Glu Cys Ser
225                 230                 235

<210> SEQ ID NO 24
<211> LENGTH: 884
<212> TYPE: DNA
<213> ORGANISM: Canis familiaris
<220> FEATURE:
<221> NAME/KEY: CDS
<222> LOCATION: (2)..(736)
<223> OTHER INFORMATION:

<400> SEQUENCE: 24 g aag aca gga tcc gtg atg acc tcc acc atg gga tgg ttc cct ctg ctc    49
  Lys Thr Gly Ser Val Met Thr Ser Thr Met Gly Trp Phe Pro Leu Leu
  1               5                   10                  15 ctc acc ctc ctg gct cac tgc aca ggt tcc tgg gcc cag tct gtg ctg    97
Leu Thr Leu Leu Ala His Cys Thr Gly Ser Trp Ala Gln Ser Val Leu
            20                  25                  30 act cag ccg gcc tca gtg tct ggg tcc ctg ggc cag agg gtc acc atc    145
Thr Gln Pro Ala Ser Val Ser Gly Ser Leu Gly Gln Arg Val Thr Ile
        35                  40                  45

-continued

| | | | | | | | | | | | | | | | | |
|---|---|---|---|---|---|---|---|---|---|---|---|---|---|---|---|---|
| tcc | tgc | act | gga | acc | agc | tcc | aat | atc | ggt | aca | gat | tat | gtg | ggc | tgg | 193 |
| Ser | Cys | Thr | Gly | Thr | Ser | Ser | Asn | Ile | Gly | Thr | Asp | Tyr | Val | Gly | Trp | |
| | 50 | | | | 55 | | | | 60 | | | | | | | |
| tac | caa | cag | ctc | cca | gga | aga | ggc | ccc | aga | acc | ctc | atc | tct | gat | act | 241 |
| Tyr | Gln | Gln | Leu | Pro | Gly | Arg | Gly | Pro | Arg | Thr | Leu | Ile | Ser | Asp | Thr | |
| 65 | | | | | 70 | | | | | 75 | | | | | 80 | |
| agt | cgc | cga | ccc | tcg | ggg | gtc | cct | gat | cga | ttc | tct | ggc | tcc | agg | tca | 289 |
| Ser | Arg | Arg | Pro | Ser | Gly | Val | Pro | Asp | Arg | Phe | Ser | Gly | Ser | Arg | Ser | |
| | | | | 85 | | | | | 90 | | | | | 95 | | |
| ggc | acc | aca | gca | atc | ctg | act | atc | tct | ggg | ctc | cag | gct | gag | gac | gag | 337 |
| Gly | Thr | Thr | Ala | Ile | Leu | Thr | Ile | Ser | Gly | Leu | Gln | Ala | Glu | Asp | Glu | |
| | | | 100 | | | | | 105 | | | | | 110 | | | |
| gct | gat | tat | tac | tgc | tca | gca | tat | gac | agc | agt | ctc | ggt | gga | act | atc | 385 |
| Ala | Asp | Tyr | Tyr | Cys | Ser | Ala | Tyr | Asp | Ser | Ser | Leu | Gly | Gly | Thr | Ile | |
| | | | 115 | | | | | 120 | | | | | 125 | | | |
| ttc | ggc | gga | ggc | act | ttc | ctg | acc | gtc | ctc | ggt | cag | ccc | aag | gcc | tcc | 433 |
| Phe | Gly | Gly | Gly | Thr | Phe | Leu | Thr | Val | Leu | Gly | Gln | Pro | Lys | Ala | Ser | |
| | 130 | | | | | 135 | | | | | 140 | | | | | |
| ccc | tcg | gtc | aca | ctc | ttc | ccg | ccc | tcc | tct | gag | gag | ctc | ggc | gcc | aac | 481 |
| Pro | Ser | Val | Thr | Leu | Phe | Pro | Pro | Ser | Ser | Glu | Glu | Leu | Gly | Ala | Asn | |
| 145 | | | | | 150 | | | | | 155 | | | | | 160 | |
| aag | gcc | acc | ctg | gtg | tgc | ctc | atc | agc | gac | ttc | tac | ccc | agc | ggc | gtg | 529 |
| Lys | Ala | Thr | Leu | Val | Cys | Leu | Ile | Ser | Asp | Phe | Tyr | Pro | Ser | Gly | Val | |
| | | | | 165 | | | | | 170 | | | | | 175 | | |
| acg | gtg | gcc | tgg | aag | gca | gac | ggc | agc | ccc | gtc | acc | cag | ggc | gtg | gag | 577 |
| Thr | Val | Ala | Trp | Lys | Ala | Asp | Gly | Ser | Pro | Val | Thr | Gln | Gly | Val | Glu | |
| | | | 180 | | | | | 185 | | | | | 190 | | | |
| acc | acc | aag | ccc | tcc | aag | cag | agc | aac | aac | aag | tac | gcg | gcc | agc | agc | 625 |
| Thr | Thr | Lys | Pro | Ser | Lys | Gln | Ser | Asn | Asn | Lys | Tyr | Ala | Ala | Ser | Ser | |
| | | 195 | | | | | 200 | | | | | 205 | | | | |
| tac | ctg | agc | ctg | acg | cct | gac | aag | tgg | aaa | tct | cac | agc | agc | ttc | agc | 673 |
| Tyr | Leu | Ser | Leu | Thr | Pro | Asp | Lys | Trp | Lys | Ser | His | Ser | Ser | Phe | Ser | |
| | 210 | | | | | 215 | | | | | 220 | | | | | |
| tgc | ctg | gtc | acg | cac | gag | ggg | agc | acc | gtg | gag | aag | aag | gtg | gcc | ccc | 721 |
| Cys | Leu | Val | Thr | His | Glu | Gly | Ser | Thr | Val | Glu | Lys | Lys | Val | Ala | Pro | |
| 225 | | | | | 230 | | | | | 235 | | | | | 240 | |
| gca | gag | tgc | tct | tag | gttcccgacg | gccccgccca | ccgaagggg | cccggagcct | | | | | | | | 776 |
| Ala | Glu | Cys | Ser | | | | | | | | | | | | | | caggacctcc aggaggatct tgcctcccat ctgggtcatc ccgccttct ccccgcaccc    836 aggcagcact caataaagtg ttctttgttc aatcaaaaaa aaaaaaaa                884

<210> SEQ ID NO 25
<211> LENGTH: 244
<212> TYPE: PRT
<213> ORGANISM: Canis familiaris

<400> SEQUENCE: 25

Lys Thr Gly Ser Val Met Thr Ser Thr Met Gly Trp Phe Pro Leu Leu
1               5                   10                  15

Leu Thr Leu Leu Ala His Cys Thr Gly Ser Trp Ala Gln Ser Val Leu
            20                  25                  30

Thr Gln Pro Ala Ser Val Ser Gly Ser Leu Gly Gln Arg Val Thr Ile
        35                  40                  45

Ser Cys Thr Gly Thr Ser Ser Asn Ile Gly Thr Asp Tyr Val Gly Trp
    50                  55                  60

Tyr Gln Gln Leu Pro Gly Arg Gly Pro Arg Thr Leu Ile Ser Asp Thr
65                  70                  75                  80

Ser Arg Arg Pro Ser Gly Val Pro Asp Arg Phe Ser Gly Ser Arg Ser

```
                    85                  90                  95
Gly Thr Thr Ala Ile Leu Thr Ile Ser Gly Leu Gln Ala Glu Asp Glu
                100                 105                 110

Ala Asp Tyr Tyr Cys Ser Ala Tyr Asp Ser Ser Leu Gly Gly Thr Ile
            115                 120                 125

Phe Gly Gly Gly Thr Phe Leu Thr Val Leu Gly Gln Pro Lys Ala Ser
130                 135                 140

Pro Ser Val Thr Leu Phe Pro Pro Ser Glu Glu Leu Gly Ala Asn
145                 150                 155                 160

Lys Ala Thr Leu Val Cys Leu Ile Ser Asp Phe Tyr Pro Ser Gly Val
                165                 170                 175

Thr Val Ala Trp Lys Ala Asp Gly Ser Pro Val Thr Gln Gly Val Glu
            180                 185                 190

Thr Thr Lys Pro Ser Lys Gln Ser Asn Asn Lys Tyr Ala Ala Ser Ser
        195                 200                 205

Tyr Leu Ser Leu Thr Pro Asp Lys Trp Lys Ser His Ser Ser Phe Ser
    210                 215                 220

Cys Leu Val Thr His Glu Gly Ser Thr Val Glu Lys Lys Val Ala Pro
225                 230                 235                 240

Ala Glu Cys Ser

<210> SEQ ID NO 26
<211> LENGTH: 729
<212> TYPE: DNA
<213> ORGANISM: Canis familiaris
<220> FEATURE:
<221> NAME/KEY: CDS
<222> LOCATION: (2)..(574)
<223> OTHER INFORMATION:

<400> SEQUENCE: 26 c tcc aac att gga ggt aat cat gta ggt tgg tac caa caa ttt cca gga        49
  Ser Asn Ile Gly Gly Asn His Val Gly Trp Tyr Gln Gln Phe Pro Gly
  1               5                  10                  15 aga ggc ccc aga act gtc atc tat agc aca aat gtt cga ccc tcg ggg         97
Arg Gly Pro Arg Thr Val Ile Tyr Ser Thr Asn Val Arg Pro Ser Gly
            20                  25                  30 gtg ccc gat cga ttc tct ggc tcc aag tct gac aac aca ggc acc ctg        145
Val Pro Asp Arg Phe Ser Gly Ser Lys Ser Asp Asn Thr Gly Thr Leu
        35                  40                  45 acc atc tct gga ctc cag gct gag gat gag gct gat tat tat tgc gca        193
Thr Ile Ser Gly Leu Gln Ala Glu Asp Glu Ala Asp Tyr Tyr Cys Ala
    50                  55                  60 acg tgg gat gat agt ctc agt gtt tct ctg ttc ggc gga ggc acc cac        241
Thr Trp Asp Asp Ser Leu Ser Val Ser Leu Phe Gly Gly Gly Thr His
65                  70                  75                  80 ctg acc gtc ctc ggt cag ccc aag gcc tcc ccc tcg gtc aca ctc ttc        289
Leu Thr Val Leu Gly Gln Pro Lys Ala Ser Pro Ser Val Thr Leu Phe
                85                  90                  95 ccg ccc tcc tct gag gag ctc ggc gcc aac aag gcc acc ctg gtg tgc        337
Pro Pro Ser Ser Glu Glu Leu Gly Ala Asn Lys Ala Thr Leu Val Cys
            100                 105                 110 ctc atc agc gac ttc tac ccc agc ggc gtg acg gtg gcc tgg aag gca        385
Leu Ile Ser Asp Phe Tyr Pro Ser Gly Val Thr Val Ala Trp Lys Ala
        115                 120                 125 gac ggc agc ccc gtc acc cag ggc gtg gag acc acc aag ccc tcc aag        433
Asp Gly Ser Pro Val Thr Gln Gly Val Glu Thr Thr Lys Pro Ser Lys
    130                 135                 140
```

```
cag acc aac aac aag tac gcg gcc agc agc tac ctg agc ctg acg cct   481
Gln Thr Asn Asn Lys Tyr Ala Ala Ser Ser Tyr Leu Ser Leu Thr Pro
145                 150                 155                 160 gac aag tgg aaa tct cac agc agc ttc agc tgc ctg gtc acg cac gag   529
Asp Lys Trp Lys Ser His Ser Ser Phe Ser Cys Leu Val Thr His Glu
            165                 170                 175 ggg agc acc gtg gag aag aag gtg gcc ccc gca gag tgc tct tag       574
Gly Ser Thr Val Glu Lys Lys Val Ala Pro Ala Glu Cys Ser
        180                 185                 190 gttcccgacg gccccgccca ccgaaggggg cccggagcct caggacctcc aggaggatct   634
tgcctcccat ctgggtcatc ccgcccttct ccccgcaccc aggcagcact caataaagtg   694
ttctttgttc aatcagaaaa aaaaaaaaaa aaaaa                              729

<210> SEQ ID NO 27
<211> LENGTH: 190
<212> TYPE: PRT
<213> ORGANISM: Canis familiaris

<400> SEQUENCE: 27

Ser Asn Ile Gly Gly Asn His Val Gly Trp Tyr Gln Gln Phe Pro Gly
1               5                   10                  15

Arg Gly Pro Arg Thr Val Ile Tyr Ser Thr Asn Val Arg Pro Ser Gly
            20                  25                  30

Val Pro Asp Arg Phe Ser Gly Ser Lys Ser Asp Asn Thr Gly Thr Leu
        35                  40                  45

Thr Ile Ser Gly Leu Gln Ala Glu Asp Glu Ala Asp Tyr Tyr Cys Ala
    50                  55                  60

Thr Trp Asp Asp Ser Leu Ser Val Ser Leu Phe Gly Gly Gly Thr His
65                  70                  75                  80

Leu Thr Val Leu Gly Gln Pro Lys Ala Ser Pro Ser Val Thr Leu Phe
                85                  90                  95

Pro Pro Ser Ser Glu Glu Leu Gly Ala Asn Lys Ala Thr Leu Val Cys
            100                 105                 110

Leu Ile Ser Asp Phe Tyr Pro Ser Gly Val Thr Val Ala Trp Lys Ala
        115                 120                 125

Asp Gly Ser Pro Val Thr Gln Gly Val Glu Thr Thr Lys Pro Ser Lys
    130                 135                 140

Gln Thr Asn Asn Lys Tyr Ala Ala Ser Ser Tyr Leu Ser Leu Thr Pro
145                 150                 155                 160

Asp Lys Trp Lys Ser His Ser Ser Phe Ser Cys Leu Val Thr His Glu
                165                 170                 175

Gly Ser Thr Val Glu Lys Lys Val Ala Pro Ala Glu Cys Ser
            180                 185                 190

<210> SEQ ID NO 28
<211> LENGTH: 1176
<212> TYPE: DNA
<213> ORGANISM: Canis familiaris
<220> FEATURE:
<221> NAME/KEY: CDS
<222> LOCATION: (2)..(730)
<223> OTHER INFORMATION:

<400> SEQUENCE: 28 a gga tcc gtg atg acc tcc acc atg ggc tgg tcc cct ctc atc ctc acc   49
  Gly Ser Val Met Thr Ser Thr Met Gly Trp Ser Pro Leu Ile Leu Thr
  1               5                   10                  15 ctc ttc gct cac tgc gca ggg tcc tgg gcc cag tct gtc ctg act cag     97
```

```
                Leu Phe Ala His Cys Ala Gly Ser Trp Ala Gln Ser Val Leu Thr Gln
                            20                  25                  30 ccg gcc tca gtg tct ggg tcc ctg ggc cag agg gtc acc atc tcc tgc        145
Pro Ala Ser Val Ser Gly Ser Leu Gly Gln Arg Val Thr Ile Ser Cys
            35                  40                  45 act gga agc agc tcc aat gtt ggt ttt ggc gat tat gtg ggc tgg tac        193
Thr Gly Ser Ser Ser Asn Val Gly Phe Gly Asp Tyr Val Gly Trp Tyr
 50                  55                  60 cag cag ctc cca gga aga ggc ccc aga acc ctc ttc tac cgt gct act        241
Gln Gln Leu Pro Gly Arg Gly Pro Arg Thr Leu Phe Tyr Arg Ala Thr
 65                  70                  75                  80 ggc cga ccc tcg ggg gtc cct gat cga ttc tct gcc tcc agg tca ggc        289
Gly Arg Pro Ser Gly Val Pro Asp Arg Phe Ser Ala Ser Arg Ser Gly
                85                  90                  95 acc aca gcg acc ctg acc atc tct gga ctc cag cct gag gat gaa gcc        337
Thr Thr Ala Thr Leu Thr Ile Ser Gly Leu Gln Pro Glu Asp Glu Ala
            100                 105                 110 gat tat tac tgc tca tcc tat gac tct act ctc ttt tct gtg ttc ggc        385
Asp Tyr Tyr Cys Ser Ser Tyr Asp Ser Thr Leu Phe Ser Val Phe Gly
            115                 120                 125 gga ggc acc tac ctg acc gtc ctc ggt cag ccc aag gcc tcc ccc tcg        433
Gly Gly Thr Tyr Leu Thr Val Leu Gly Gln Pro Lys Ala Ser Pro Ser
130                 135                 140 gtc aca ctc ttc ccg ccc tcc tct gag gag ctc ggc gcc aac aag gcc        481
Val Thr Leu Phe Pro Pro Ser Ser Glu Glu Leu Gly Ala Asn Lys Ala
145                 150                 155                 160 acc ctg gtg tgc ctc atc agc gac ttc tac ccc agc ggc gtg acg gtg        529
Thr Leu Val Cys Leu Ile Ser Asp Phe Tyr Pro Ser Gly Val Thr Val
                165                 170                 175 gcc tgg aag gca gac ggc agc ccc gtc acc cag ggc gtg gag acc acc        577
Ala Trp Lys Ala Asp Gly Ser Pro Val Thr Gln Gly Val Glu Thr Thr
            180                 185                 190 aag ccc tcc aag cag agc aac aac aag tac gcg gcc agc agc tac ctg        625
Lys Pro Ser Lys Gln Ser Asn Asn Lys Tyr Ala Ala Ser Ser Tyr Leu
        195                 200                 205 agc ctg acg cct gac aag tgg aaa tct cac agc agc ttc agc tgc ctg        673
Ser Leu Thr Pro Asp Lys Trp Lys Ser His Ser Ser Phe Ser Cys Leu
    210                 215                 220 gtc acg cac gag ggg agc acc gtg gag aag aag gtg gcc ccc gca gag        721
Val Thr His Glu Gly Ser Thr Val Glu Lys Lys Val Ala Pro Ala Glu
225                 230                 235                 240 tgc tct tag gttcccgacg gccccgccca ccgaaggggg cccggagcct               770
Cys Ser caggacctcc aggaggatct tgcctccat ctgggtcatc ccgcccttct ccccgcaccc       830
aggcagcact caataaagtg ttccaatttc aagcgactta aatgcatatg gtttttttt      890 tttgatgtga tacagctgtg tttacttcaa cctccaggga atcctaaggg cccagagact     950
ccccttgtgc tgtaagattg tgtccctgaa acaagtcacc tccagccttc cagaggggtg     1010
ggctgcctgg aggcagtggc acgggcctgg gctctctaga atgtgtactg agcaggggca     1070
ggaggcccaa agggccaccc atgcctccag gagcctccgc aggagggagc agagtctgta     1130
gaggctcacg gagaggctgg aagatcactg gaacagcagc aagcca                    1176
```

<210> SEQ ID NO 29
<211> LENGTH: 242
<212> TYPE: PRT
<213> ORGANISM: Canis familiaris

<400> SEQUENCE: 29

```
Gly Ser Val Met Thr Ser Thr Met Gly Trp Ser Pro Leu Ile Leu Thr
1               5                   10                  15

Leu Phe Ala His Cys Ala Gly Ser Trp Ala Gln Ser Val Leu Thr Gln
                20                  25                  30

Pro Ala Ser Val Ser Gly Ser Leu Gly Gln Arg Val Thr Ile Ser Cys
            35                  40                  45

Thr Gly Ser Ser Ser Asn Val Gly Phe Gly Asp Tyr Val Gly Trp Tyr
        50                  55                  60

Gln Gln Leu Pro Gly Arg Gly Pro Arg Thr Leu Phe Tyr Arg Ala Thr
65                  70                  75                  80

Gly Arg Pro Ser Gly Val Pro Asp Arg Phe Ser Ala Ser Arg Ser Gly
                85                  90                  95

Thr Thr Ala Thr Leu Thr Ile Ser Gly Leu Gln Pro Glu Asp Glu Ala
            100                 105                 110

Asp Tyr Tyr Cys Ser Ser Tyr Asp Ser Thr Leu Phe Ser Val Phe Gly
        115                 120                 125

Gly Gly Thr Tyr Leu Thr Val Leu Gly Gln Pro Lys Ala Ser Pro Ser
    130                 135                 140

Val Thr Leu Phe Pro Pro Ser Ser Glu Glu Leu Gly Ala Asn Lys Ala
145                 150                 155                 160

Thr Leu Val Cys Leu Ile Ser Asp Phe Tyr Pro Ser Gly Val Thr Val
                165                 170                 175

Ala Trp Lys Ala Asp Gly Ser Pro Val Thr Gln Gly Val Glu Thr Thr
            180                 185                 190

Lys Pro Ser Lys Gln Ser Asn Asn Lys Tyr Ala Ala Ser Ser Tyr Leu
        195                 200                 205

Ser Leu Thr Pro Asp Lys Trp Lys Ser His Ser Ser Phe Ser Cys Leu
    210                 215                 220

Val Thr His Glu Gly Ser Thr Val Glu Lys Lys Val Ala Pro Ala Glu
225                 230                 235                 240

Cys Ser

<210> SEQ ID NO 30
<211> LENGTH: 762
<212> TYPE: DNA
<213> ORGANISM: Canis familiaris
<220> FEATURE:
<221> NAME/KEY: CDS
<222> LOCATION: (1)..(609)
<223> OTHER INFORMATION:

<400> SEQUENCE: 30 ggc cag agg gtc acc atc tcc tgc act gga agc ccc aat gtt ggt tat        48
Gly Gln Arg Val Thr Ile Ser Cys Thr Gly Ser Pro Asn Val Gly Tyr
1               5                   10                  15 ggc aat tac gtg ggc tgg tac cag cag ctc cca gga aca ggc ccc aga       96
Gly Asn Tyr Val Gly Trp Tyr Gln Gln Leu Pro Gly Thr Gly Pro Arg
                20                  25                  30 acc ctc att tat ggt aag aat cac cga ccc gcg ggg gtc cct gat cga      144
Thr Leu Ile Tyr Gly Lys Asn His Arg Pro Ala Gly Val Pro Asp Arg
            35                  40                  45 ttc tct ggc tcc act tca ggc agt tca gcc aca ctg acc atc tct ggg      192
Phe Ser Gly Ser Thr Ser Gly Ser Ser Ala Thr Leu Thr Ile Ser Gly
        50                  55                  60 ctc cag gct gag gat gaa gca gat tat tac tgc tca tcc tat gac atc      240
Leu Gln Ala Glu Asp Glu Ala Asp Tyr Tyr Cys Ser Ser Tyr Asp Ile
65                  70                  75                  80
```

```
agt ctc ggt ggt gtt gtg ttc ggc gga ggc acc cat ctg acc gtc ctc      288
Ser Leu Gly Gly Val Val Phe Gly Gly Gly Thr His Leu Thr Val Leu
            85                  90                  95 ggt cag ccc aag gcc tcc ccc tcg gtc aca ctc ttc ccg ccc tcc tct      336
Gly Gln Pro Lys Ala Ser Pro Ser Val Thr Leu Phe Pro Pro Ser Ser
        100                 105                 110 gag gag ctc ggc gcc aac aag gcc acc ctg gtg tgc ctc atc agc gac      384
Glu Glu Leu Gly Ala Asn Lys Ala Thr Leu Val Cys Leu Ile Ser Asp
    115                 120                 125 ttc tac ccc agt ggc gtg acg gtg gcc tgg aag gca gac ggc agc ccc      432
Phe Tyr Pro Ser Gly Val Thr Val Ala Trp Lys Ala Asp Gly Ser Pro
130                 135                 140 gtc acc cag ggc gtg gag acc acc aag ccc tcc aag cag agc aac aac      480
Val Thr Gln Gly Val Glu Thr Thr Lys Pro Ser Lys Gln Ser Asn Asn
145                 150                 155                 160 aag tac gcg gcc agc agc tac ctg agc ctg acg cct gac aag tgg aaa      528
Lys Tyr Ala Ala Ser Ser Tyr Leu Ser Leu Thr Pro Asp Lys Trp Lys
                165                 170                 175 tct cac agc agc ttc agc tgc ctg gtc aca cac gag ggg agc acc gtg      576
Ser His Ser Ser Phe Ser Cys Leu Val Thr His Glu Gly Ser Thr Val
            180                 185                 190 gag aag aag gtg gcc ccc gca gag tgc tct tag gttcccgacg ccccgccca    629
Glu Lys Lys Val Ala Pro Ala Glu Cys Ser
        195                 200 cctaagggg cccggagcct caggacctcc aggaggatct tgcctcctat ctgggtcatc    689
ccgcccttct ccccacaccc aggcagcact caataaagtg ttctttgttc aatcagaaaa    749
aaaaaaaaaa aaa                                                        762

<210> SEQ ID NO 31
<211> LENGTH: 202
<212> TYPE: PRT
<213> ORGANISM: Canis familiaris

<400> SEQUENCE: 31

Gly Gln Arg Val Thr Ile Ser Cys Thr Gly Ser Pro Asn Val Gly Tyr
1               5                   10                  15

Gly Asn Tyr Val Gly Trp Tyr Gln Gln Leu Pro Gly Thr Gly Pro Arg
            20                  25                  30

Thr Leu Ile Tyr Gly Lys Asn His Arg Pro Ala Gly Val Pro Asp Arg
        35                  40                  45

Phe Ser Gly Ser Thr Ser Gly Ser Ser Ala Thr Leu Thr Ile Ser Gly
    50                  55                  60

Leu Gln Ala Glu Asp Glu Ala Asp Tyr Tyr Cys Ser Ser Tyr Asp Ile
65                  70                  75                  80

Ser Leu Gly Gly Val Val Phe Gly Gly Gly Thr His Leu Thr Val Leu
                85                  90                  95

Gly Gln Pro Lys Ala Ser Pro Ser Val Thr Leu Phe Pro Pro Ser Ser
            100                 105                 110

Glu Glu Leu Gly Ala Asn Lys Ala Thr Leu Val Cys Leu Ile Ser Asp
        115                 120                 125

Phe Tyr Pro Ser Gly Val Thr Val Ala Trp Lys Ala Asp Gly Ser Pro
    130                 135                 140

Val Thr Gln Gly Val Glu Thr Thr Lys Pro Ser Lys Gln Ser Asn Asn
145                 150                 155                 160

Lys Tyr Ala Ala Ser Ser Tyr Leu Ser Leu Thr Pro Asp Lys Trp Lys
                165                 170                 175
```

```
Ser His Ser Ser Phe Ser Cys Leu Val Thr His Glu Gly Ser Thr Val
        180                 185                 190

Glu Lys Lys Val Ala Pro Ala Glu Cys Ser
        195                 200

<210> SEQ ID NO 32
<211> LENGTH: 826
<212> TYPE: DNA
<213> ORGANISM: Canis familiaris
<220> FEATURE:
<221> NAME/KEY: CDS
<222> LOCATION: (1)..(678)
<223> OTHER INFORMATION:

<400> SEQUENCE: 32 ctt gtc agc ctc ctg gct ctc tgc aca ggt tct gtg gcc tcc tat gtg      48
Leu Val Ser Leu Leu Ala Leu Cys Thr Gly Ser Val Ala Ser Tyr Val
1               5                   10                  15 ctg aca cag ccg ccg tcc atg agt gtg acc ctg agg cag acg gcc cgc      96
Leu Thr Gln Pro Pro Ser Met Ser Val Thr Leu Arg Gln Thr Ala Arg
                20                  25                  30 atc acc tgt gag gga gac agc att gga gat aaa aga gtt tac tgg tac     144
Ile Thr Cys Glu Gly Asp Ser Ile Gly Asp Lys Arg Val Tyr Trp Tyr
            35                  40                  45 cag cag aaa ctg ggc cgg ggc ccg atg ttg att att tat gat ggt acc     192
Gln Gln Lys Leu Gly Arg Gly Pro Met Leu Ile Ile Tyr Asp Gly Thr
        50                  55                  60 tac agg ccg tca ggg atc cct gac cga ttc ttc ggc gcc aat tcg ggg     240
Tyr Arg Pro Ser Gly Ile Pro Asp Arg Phe Phe Gly Ala Asn Ser Gly
65                  70                  75                  80 agc aca gcc acc ctg acc atc agc ggg gcc ctg gcc gag gac gag gct     288
Ser Thr Ala Thr Leu Thr Ile Ser Gly Ala Leu Ala Glu Asp Glu Ala
                85                  90                  95 gac tat tac tgc cag gtg tgg gac aat ggt gaa att att ttc ggc gga     336
Asp Tyr Tyr Cys Gln Val Trp Asp Asn Gly Glu Ile Ile Phe Gly Gly
            100                 105                 110 ggc acc cgt ctg acc gtc ctc ggt cag ccc aag gcc tcc cct tcg gtc     384
Gly Thr Arg Leu Thr Val Leu Gly Gln Pro Lys Ala Ser Pro Ser Val
        115                 120                 125 aca ctc ttc ccg ccc tcc tct gag gag ctt ggc gcc aac aag gcc acc     432
Thr Leu Phe Pro Pro Ser Ser Glu Glu Leu Gly Ala Asn Lys Ala Thr
    130                 135                 140 ctg gtg tgc ctc atc agc gac ttc tac ccc agc ggc gtg aca gtg gcc     480
Leu Val Cys Leu Ile Ser Asp Phe Tyr Pro Ser Gly Val Thr Val Ala
145                 150                 155                 160 tgg aag gca gac ggc agc ccc atc acc cag ggt gtg gag acc acc aag     528
Trp Lys Ala Asp Gly Ser Pro Ile Thr Gln Gly Val Glu Thr Thr Lys
                165                 170                 175 ccc tcc aag cag agc aac aac aag tac gcg gcc agc agc tac ctg agc     576
Pro Ser Lys Gln Ser Asn Asn Lys Tyr Ala Ala Ser Ser Tyr Leu Ser
            180                 185                 190 ctg acg cct gac aag tgg aaa tct cac agc agc ttc agc tgc ctg gtc     624
Leu Thr Pro Asp Lys Trp Lys Ser His Ser Ser Phe Ser Cys Leu Val
        195                 200                 205 acg cac gag ggg agc acc gtg gag aag aag gtg gcc ccc gca gag tgc     672
Thr His Glu Gly Ser Thr Val Glu Lys Lys Val Ala Pro Ala Glu Cys
    210                 215                 220 tct tag gttcctgatg tccccgccc accaaggggg gctcagagcc tcaggacctc      728
Ser
225
```

```
caggaggatc ttgcctccca tctgggtcat cccagccttt ccccttaaac ccaggcaaca    788
ttcaataaag tgttctttct tcaatcagaa ggggcccg                             826
```

<210> SEQ ID NO 33
<211> LENGTH: 225
<212> TYPE: PRT
<213> ORGANISM: Canis familiaris

<400> SEQUENCE: 33

```
Leu Val Ser Leu Leu Ala Leu Cys Thr Gly Ser Val Ala Ser Tyr Val
 1               5                  10                  15

Leu Thr Gln Pro Pro Ser Met Ser Val Thr Leu Arg Gln Thr Ala Arg
             20                  25                  30

Ile Thr Cys Glu Gly Asp Ser Ile Gly Asp Lys Arg Val Tyr Trp Tyr
         35                  40                  45

Gln Gln Lys Leu Gly Arg Gly Pro Met Leu Ile Ile Tyr Asp Gly Thr
     50                  55                  60

Tyr Arg Pro Ser Gly Ile Pro Asp Arg Phe Phe Gly Ala Asn Ser Gly
 65                  70                  75                  80

Ser Thr Ala Thr Leu Thr Ile Ser Gly Ala Leu Ala Glu Asp Glu Ala
                 85                  90                  95

Asp Tyr Tyr Cys Gln Val Trp Asp Asn Gly Glu Ile Ile Phe Gly Gly
            100                 105                 110

Gly Thr Arg Leu Thr Val Leu Gly Gln Pro Lys Ala Ser Pro Ser Val
        115                 120                 125

Thr Leu Phe Pro Pro Ser Ser Glu Glu Leu Gly Ala Asn Lys Ala Thr
    130                 135                 140

Leu Val Cys Leu Ile Ser Asp Phe Tyr Pro Ser Gly Val Thr Val Ala
145                 150                 155                 160

Trp Lys Ala Asp Gly Ser Pro Ile Thr Gln Gly Val Glu Thr Thr Lys
                165                 170                 175

Pro Ser Lys Gln Ser Asn Asn Lys Tyr Ala Ala Ser Ser Tyr Leu Ser
            180                 185                 190

Leu Thr Pro Asp Lys Trp Lys Ser His Ser Ser Phe Ser Cys Leu Val
        195                 200                 205

Thr His Glu Gly Ser Thr Val Glu Lys Lys Val Ala Pro Ala Glu Cys
    210                 215                 220

Ser
225
```

<210> SEQ ID NO 34
<211> LENGTH: 796
<212> TYPE: DNA
<213> ORGANISM: Canis familiaris
<220> FEATURE:
<221> NAME/KEY: CDS
<222> LOCATION: (2)..(643)
<223> OTHER INFORMATION:

<400> SEQUENCE: 34

```
g ctg act cag ccg gcc tca gtg tct ggg tcc ctg ggc cag agg gtc acc    49
  Leu Thr Gln Pro Ala Ser Val Ser Gly Ser Leu Gly Gln Arg Val Thr
   1               5                  10                  15 atc tcc tgc act gga agc agt tcc aac att gga agt aat gat gtg ggt    97
Ile Ser Cys Thr Gly Ser Ser Ser Asn Ile Gly Ser Asn Asp Val Gly
             20                  25                  30 tgg tac cag cag ctc cca gga aga ggc ccc aaa act gtc gtc tct aat   145
Trp Tyr Gln Gln Leu Pro Gly Arg Gly Pro Lys Thr Val Val Ser Asn
```

|  |  |  |  |  |  |  |  |  |  |  |  |  |  |  |  |
|---|---|---|---|---|---|---|---|---|---|---|---|---|---|---|---|
| aca | aat | att | cgg | ccc | tcg | ggg | gtg | ccc | gat | cga | ttc | tct | gcc | tcc | aag | 193
| Thr | Asn | Ile | Arg | Pro | Ser | Gly | Val | Pro | Asp | Arg | Phe | Ser | Ala | Ser | Lys |
|     | 50  |     |     |     | 55  |     |     |     |     | 60  |     |     |     |     |     |

```
aca aat att cgg ccc tcg ggg gtg ccc gat cga ttc tct gcc tcc aag     193
Thr Asn Ile Arg Pro Ser Gly Val Pro Asp Arg Phe Ser Ala Ser Lys
     50              55                  60 tct ggc agc aca gcc acc ctg acc atc tct ggc ctc cag gct gag gat     241
Ser Gly Ser Thr Ala Thr Leu Thr Ile Ser Gly Leu Gln Ala Glu Asp
 65              70              75                  80 gag gct gat tat tac tgc tca acg tgg gat aat agt ctc agt act tac     289
Glu Ala Asp Tyr Tyr Cys Ser Thr Trp Asp Asn Ser Leu Ser Thr Tyr
                 85              90                  95 atg ttc ggc tct gga acc caa ctg acc gtc ctt ggt cag ccc aag gcc     337
Met Phe Gly Ser Gly Thr Gln Leu Thr Val Leu Gly Gln Pro Lys Ala
             100                 105                 110 tcc ccc tcg gtc aca ctc ttc ccg ccc tcc tct gag gag ctc ggc gcc     385
Ser Pro Ser Val Thr Leu Phe Pro Pro Ser Ser Glu Glu Leu Gly Ala
         115                 120                 125 aac aag gcc acc ctg gtg tgc ctc atc agc gac ttc tac ccc agc ggc     433
Asn Lys Ala Thr Leu Val Cys Leu Ile Ser Asp Phe Tyr Pro Ser Gly
     130                 135                 140 gtg acg gtg gcc tgg aag gca gac ggc agc ccc atc acc cag ggc gtg     481
Val Thr Val Ala Trp Lys Ala Asp Gly Ser Pro Ile Thr Gln Gly Val
145                 150                 155                 160 gag acc acc aag ccc tcc aag cag agc aac aac aag tac gcg gcc agc     529
Glu Thr Thr Lys Pro Ser Lys Gln Ser Asn Asn Lys Tyr Ala Ala Ser
                 165                 170                 175 agc tac ctg agc ctg acg cct gac aag tgg aaa tct cac agc agc ttc     577
Ser Tyr Leu Ser Leu Thr Pro Asp Lys Trp Lys Ser His Ser Ser Phe
             180                 185                 190 agc tgc ctg gtc acg cac gag ggg agc act gtg gag aag aag gtg gcc     625
Ser Cys Leu Val Thr His Glu Gly Ser Thr Val Glu Lys Lys Val Ala
         195                 200                 205 ccc gca gag tgc tct tag gttcccgatg ccccccgccc accgaagggg            673
Pro Ala Glu Cys Ser
     210 gctcggagcc tcaggacctc caggaggatc ttgcctccca tctgggtctt cccagccctt   733 ttccccacac tcaggcaaca ctcaataaag tgtcctttat tcaatcagaa aaaaaaaaa    793 aaa                                                                 796

<210> SEQ ID NO 35
<211> LENGTH: 213
<212> TYPE: PRT
<213> ORGANISM: Canis familiaris

<400> SEQUENCE: 35

Leu Thr Gln Pro Ala Ser Val Ser Gly Ser Leu Gly Gln Arg Val Thr
 1               5                  10                  15

Ile Ser Cys Thr Gly Ser Ser Ser Asn Ile Gly Ser Asn Asp Val Gly
             20                  25                  30

Trp Tyr Gln Gln Leu Pro Gly Arg Gly Pro Lys Thr Val Val Ser Asn
         35                  40                  45

Thr Asn Ile Arg Pro Ser Gly Val Pro Asp Arg Phe Ser Ala Ser Lys
     50                  55                  60

Ser Gly Ser Thr Ala Thr Leu Thr Ile Ser Gly Leu Gln Ala Glu Asp
 65                  70                  75                  80

Glu Ala Asp Tyr Tyr Cys Ser Thr Trp Asp Asn Ser Leu Ser Thr Tyr
                 85                  90                  95

Met Phe Gly Ser Gly Thr Gln Leu Thr Val Leu Gly Gln Pro Lys Ala
```

```
            100                 105                 110
Ser Pro Ser Val Thr Leu Phe Pro Pro Ser Ser Glu Glu Leu Gly Ala
        115                 120                 125

Asn Lys Ala Thr Leu Val Cys Leu Ile Ser Asp Phe Tyr Pro Ser Gly
        130                 135                 140

Val Thr Val Ala Trp Lys Ala Asp Gly Ser Pro Ile Thr Gln Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Asp Lys Trp Lys Ser His Ser Ser Phe
                180                 185                 190

Ser Cys Leu Val Thr His Glu Gly Ser Thr Val Glu Lys Lys Val Ala
        195                 200                 205

Pro Ala Glu Cys Ser
        210

<210> SEQ ID NO 36
<211> LENGTH: 930
<212> TYPE: DNA
<213> ORGANISM: Canis familiaris
<220> FEATURE:
<221> NAME/KEY: CDS
<222> LOCATION: (1)..(774)
<223> OTHER INFORMATION:

<400> SEQUENCE: 36 atg aag agg gtg aga aat att gaa aag att ata ata aat cag gtg gat      48
Met Lys Arg Val Arg Asn Ile Glu Lys Ile Ile Ile Asn Gln Val Asp
1               5                   10                  15 gtg atg acc tcc acc atg ggc tgg ttc cct ctc atc ctc acc ctc ctc      96
Val Met Thr Ser Thr Met Gly Trp Phe Pro Leu Ile Leu Thr Leu Leu
            20                  25                  30 gct cac tgc gca ggg tcc tgg gcc cag tct gtg ctg act cag ccg gcc     144
Ala His Cys Ala Gly Ser Trp Ala Gln Ser Val Leu Thr Gln Pro Ala
        35                  40                  45 tca gtg tct ggg tcc ctg ggc cag agg gtc acc atc tcc tgc act gga     192
Ser Val Ser Gly Ser Leu Gly Gln Arg Val Thr Ile Ser Cys Thr Gly
    50                  55                  60 agc agc tcc aat gtt ggt tat ggc aat tat gtg ggc tgg tac cag cag     240
Ser Ser Ser Asn Val Gly Tyr Gly Asn Tyr Val Gly Trp Tyr Gln Gln
65                  70                  75                  80 ctc cca gga aca agc ccc aga aac ctc atc tat gat act agt agc cga     288
Leu Pro Gly Thr Ser Pro Arg Asn Leu Ile Tyr Asp Thr Ser Ser Arg
                85                  90                  95 ccc tcg ggg gtc cct gat cga ttc tct ggc tcc agg tca ggc agc aca     336
Pro Ser Gly Val Pro Asp Arg Phe Ser Gly Ser Arg Ser Gly Ser Thr
            100                 105                 110 gca acc ctg acc atc tct ggg ctc cag gct gag gat gaa gcc gat tat     384
Ala Thr Leu Thr Ile Ser Gly Leu Gln Ala Glu Asp Glu Ala Asp Tyr
        115                 120                 125 tac tgc tca tcc tat gac aga agt ctc agt ggt gct gtg ttc ggc gga     432
Tyr Cys Ser Ser Tyr Asp Arg Ser Leu Ser Gly Ala Val Phe Gly Gly
    130                 135                 140 ggc acc cac ctg acc gtc ctc ggt cag ccc aag gcc tcc ccc tcg gtc     480
Gly Thr His Leu Thr Val Leu Gly Gln Pro Lys Ala Ser Pro Ser Val
145                 150                 155                 160 aca ctc ttc ccg ccc tcc tct gag gag ctc ggc gcc aac aag gcc acc     528
Thr Leu Phe Pro Pro Ser Ser Glu Glu Leu Gly Ala Asn Lys Ala Thr
                165                 170                 175
```

```
ctg gtg tgc ctc atc agc gac ttc tac ccc agc ggc gtg acg gtg gcc        576
Leu Val Cys Leu Ile Ser Asp Phe Tyr Pro Ser Gly Val Thr Val Ala
        180                 185                 190 tgg aag gca gac ggc agc ccc gtc acc cag ggc gtg gag acc acc aag        624
Trp Lys Ala Asp Gly Ser Pro Val Thr Gln Gly Val Glu Thr Thr Lys
    195                 200                 205 ccc tcc aag cag agc aac aac aag tac gcg gcc agc agc tac ctg agc        672
Pro Ser Lys Gln Ser Asn Asn Lys Tyr Ala Ala Ser Ser Tyr Leu Ser
210                 215                 220 ctg acg cct gac aag tgg aaa tct cac agc agc ttc agc tgc ctg gtc        720
Leu Thr Pro Asp Lys Trp Lys Ser His Ser Ser Phe Ser Cys Leu Val
225                 230                 235                 240 acg cac gag ggg agc acc gtg gag aag aag gtg gcc ccc gca gag tgc        768
Thr His Glu Gly Ser Thr Val Glu Lys Lys Val Ala Pro Ala Glu Cys
                245                 250                 255 tct tag gttcccgacg ccccgccca ccgaagggg cccggagcct caggacctcc           824
Ser aggaggatct tgcctcccat ctgggtcatc ccgcccttct cccgcaccc aggcagcact        884 caataaagtg ttctttgttc aatcagaaaa aaaaaaaaa aaaaaa                      930

<210> SEQ ID NO 37
<211> LENGTH: 257
<212> TYPE: PRT
<213> ORGANISM: Canis familiaris

<400> SEQUENCE: 37

Met Lys Arg Val Arg Asn Ile Glu Lys Ile Ile Asn Gln Val Asp
1               5                   10                  15

Val Met Thr Ser Thr Met Gly Trp Phe Pro Leu Ile Leu Thr Leu Leu
                20                  25                  30

Ala His Cys Ala Gly Ser Trp Ala Gln Ser Val Leu Thr Gln Pro Ala
            35                  40                  45

Ser Val Ser Gly Ser Leu Gly Gln Arg Val Thr Ile Ser Cys Thr Gly
        50                  55                  60

Ser Ser Ser Asn Val Gly Tyr Gly Asn Tyr Val Gly Trp Tyr Gln Gln
65                  70                  75                  80

Leu Pro Gly Thr Ser Pro Arg Asn Leu Ile Tyr Asp Thr Ser Ser Arg
                85                  90                  95

Pro Ser Gly Val Pro Asp Arg Phe Ser Gly Ser Arg Ser Gly Ser Thr
            100                 105                 110

Ala Thr Leu Thr Ile Ser Gly Leu Gln Ala Glu Asp Glu Ala Asp Tyr
        115                 120                 125

Tyr Cys Ser Ser Tyr Asp Arg Ser Leu Ser Gly Ala Val Phe Gly Gly
    130                 135                 140

Gly Thr His Leu Thr Val Leu Gly Gln Pro Lys Ala Ser Pro Ser Val
145                 150                 155                 160

Thr Leu Phe Pro Pro Ser Ser Glu Glu Leu Gly Ala Asn Lys Ala Thr
                165                 170                 175

Leu Val Cys Leu Ile Ser Asp Phe Tyr Pro Ser Gly Val Thr Val Ala
            180                 185                 190

Trp Lys Ala Asp Gly Ser Pro Val Thr Gln Gly Val Glu Thr Thr Lys
        195                 200                 205

Pro Ser Lys Gln Ser Asn Asn Lys Tyr Ala Ala Ser Ser Tyr Leu Ser
    210                 215                 220

Leu Thr Pro Asp Lys Trp Lys Ser His Ser Ser Phe Ser Cys Leu Val
225                 230                 235                 240
```

```
Thr His Glu Gly Ser Thr Val Glu Lys Lys Val Ala Pro Glu Cys
        245                 250                 255
Ser

<210> SEQ ID NO 38
<211> LENGTH: 843
<212> TYPE: DNA
<213> ORGANISM: Canis familiaris
<220> FEATURE:
<221> NAME/KEY: CDS
<222> LOCATION: (9)..(692)
<223> OTHER INFORMATION:

<400> SEQUENCE: 38 gcaaacat atg tac aaa att cta gag tct acg tac att gtg aaa aga tca        50
         Met Tyr Lys Ile Leu Glu Ser Thr Tyr Ile Val Lys Arg Ser
         1               5                   10 atc act gtc cct cag cca cca ttt gtg agt gtg acc ctg agg gac acg        98
Ile Thr Val Pro Gln Pro Pro Phe Val Ser Val Thr Leu Arg Asp Thr
15              20                  25                  30 gcc cac atc acc tgt ggg gga gac aac att gga agt aaa tat gtt caa        146
Ala His Ile Thr Cys Gly Gly Asp Asn Ile Gly Ser Lys Tyr Val Gln
                35                  40                  45 tgg atc caa cag aat cca ggt cag gcc ccc gtg gtg att atc tat aga        194
Trp Ile Gln Gln Asn Pro Gly Gln Ala Pro Val Val Ile Ile Tyr Arg
            50                  55                  60 gat acc aag agg ccg aca tgg atc cct gag cga ttc tct ggc gcc aac        242
Asp Thr Lys Arg Pro Thr Trp Ile Pro Glu Arg Phe Ser Gly Ala Asn
        65                  70                  75 tca ggg aac acg gct acc ctg acc atc agt ggg gtc ctg gcc gag gac        290
Ser Gly Asn Thr Ala Thr Leu Thr Ile Ser Gly Val Leu Ala Glu Asp
    80                  85                  90 gag gct gac tat tac tgc cag gtg aca gac agt ggt cct cag act aat        338
Glu Ala Asp Tyr Tyr Cys Gln Val Thr Asp Ser Gly Pro Gln Thr Asn
95                  100                 105                 110 gtt ttc ggc gga ggc acc cat ctg acc gtc ctc agt cag ccc aag gcc        386
Val Phe Gly Gly Gly Thr His Leu Thr Val Leu Ser Gln Pro Lys Ala
                115                 120                 125 tcc ccc tcg gtc aca ctc ttc ccg ccc tcc tct gag gag ctc ggc gcc        434
Ser Pro Ser Val Thr Leu Phe Pro Pro Ser Ser Glu Glu Leu Gly Ala
            130                 135                 140 aac aag gcc acc ctg gtg tgc ctc atc agc gac ttc tac ccc agt ggc        482
Asn Lys Ala Thr Leu Val Cys Leu Ile Ser Asp Phe Tyr Pro Ser Gly
        145                 150                 155 gtg acg gtg gcc tgg aag gca gac ggc agc ccc gtc acc cag ggc gtg        530
Val Thr Val Ala Trp Lys Ala Asp Gly Ser Pro Val Thr Gln Gly Val
    160                 165                 170 gag acc acc aag ccc tcc aag cag agc aac aac aag tac gcg gcc agc        578
Glu Thr Thr Lys Pro Ser Lys Gln Ser Asn Asn Lys Tyr Ala Ala Ser
175                 180                 185                 190 agc tac ctg agc ctg acg cct gac aag tgg aaa tct cac agc agc ttc        626
Ser Tyr Leu Ser Leu Thr Pro Asp Lys Trp Lys Ser His Ser Ser Phe
                195                 200                 205 agc tgc ctg gtc aca cac gag ggg agc acc gtg gag aag aag gtg gcc        674
Ser Cys Leu Val Thr His Glu Gly Ser Thr Val Glu Lys Lys Val Ala
            210                 215                 220 ccc gca gag tgc tct tag gttcccgacg ccccgccca cctaaggggg              722
Pro Ala Glu Cys Ser
            225 cccggagcct caggacctcc aggaggatct tgcctcctat ctgggtcatc ccgcccttct      782
```

```
cccacaccc aggcagcact caataaattg ttctttgttc aatcagaaaa aaggggggcc    842
c                                                                   843
```

<210> SEQ ID NO 39
<211> LENGTH: 227
<212> TYPE: PRT
<213> ORGANISM: Canis familiaris

<400> SEQUENCE: 39

```
Met Tyr Lys Ile Leu Glu Ser Thr Tyr Ile Val Lys Arg Ser Ile Thr
1               5                   10                  15

Val Pro Gln Pro Pro Phe Val Ser Val Thr Leu Arg Asp Thr Ala His
                20                  25                  30

Ile Thr Cys Gly Gly Asp Asn Ile Gly Ser Lys Tyr Val Gln Trp Ile
            35                  40                  45

Gln Gln Asn Pro Gly Gln Ala Pro Val Val Ile Ile Tyr Arg Asp Thr
        50                  55                  60

Lys Arg Pro Thr Trp Ile Pro Glu Arg Phe Ser Gly Ala Asn Ser Gly
65                  70                  75                  80

Asn Thr Ala Thr Leu Thr Ile Ser Gly Val Leu Ala Glu Asp Glu Ala
                85                  90                  95

Asp Tyr Tyr Cys Gln Val Thr Asp Ser Gly Pro Gln Thr Asn Val Phe
            100                 105                 110

Gly Gly Gly Thr His Leu Thr Val Leu Ser Gln Pro Lys Ala Ser Pro
        115                 120                 125

Ser Val Thr Leu Phe Pro Pro Ser Ser Glu Glu Leu Gly Ala Asn Lys
    130                 135                 140

Ala Thr Leu Val Cys Leu Ile Ser Asp Phe Tyr Pro Ser Gly Val Thr
145                 150                 155                 160

Val Ala Trp Lys Ala Asp Gly Ser Pro Val Thr Gln Gly Val Glu Thr
                165                 170                 175

Thr Lys Pro Ser Lys Gln Ser Asn Asn Lys Tyr Ala Ala Ser Ser Tyr
            180                 185                 190

Leu Ser Leu Thr Pro Asp Lys Trp Lys Ser His Ser Ser Phe Ser Cys
        195                 200                 205

Leu Val Thr His Glu Gly Ser Thr Val Glu Lys Val Ala Pro Ala
    210                 215                 220

Glu Cys Ser
225
```

<210> SEQ ID NO 40
<211> LENGTH: 858
<212> TYPE: DNA
<213> ORGANISM: Canis familiaris
<220> FEATURE:
<221> NAME/KEY: CDS
<222> LOCATION: (2)..(712)
<223> OTHER INFORMATION:

<400> SEQUENCE: 40

```
c tcc aac atg gcc tgg tcc cct ctc ctc ctc aca ctc ctt gct tac tgc    49
  Ser Asn Met Ala Trp Ser Pro Leu Leu Leu Thr Leu Leu Ala Tyr Cys
  1               5                   10                  15 aca ggg tcc tgg gcc cag tct gtg ctg act cag ccg acc tca gtg tcg    97
Thr Gly Ser Trp Ala Gln Ser Val Leu Thr Gln Pro Thr Ser Val Ser
            20                  25                  30 ggg tcc ctt ggc cag agg gtc acc atc tcc tgc tct gga agc acg aac    145
```

```
Gly Ser Leu Gly Gln Arg Val Thr Ile Ser Cys Ser Gly Ser Thr Asn
             35                  40                  45 aac atc ggt att gtt ggt gcg agc tgg tac caa cag ctc cca gga aag      193
Asn Ile Gly Ile Val Gly Ala Ser Trp Tyr Gln Gln Leu Pro Gly Lys
 50                  55                  60 gcc cct aaa ctc ctc gtg tac agt gtt ggg gat cga ccg tca ggg gtc      241
Ala Pro Lys Leu Leu Val Tyr Ser Val Gly Asp Arg Pro Ser Gly Val
 65                  70                  75                  80 cct gac cgg ttt tcc ggc tcc aac tct ggc aac tca gcc acc ctg acc      289
Pro Asp Arg Phe Ser Gly Ser Asn Ser Gly Asn Ser Ala Thr Leu Thr
                 85                  90                  95 atc act ggg ctt cag gct gag gac gag gct gat tat tac tgc cag tcc      337
Ile Thr Gly Leu Gln Ala Glu Asp Glu Ala Asp Tyr Tyr Cys Gln Ser
            100                 105                 110 ttt gat acc acg ctt ggt gct gtg ttc ggc gga ggc acc cac ctg acc      385
Phe Asp Thr Thr Leu Gly Ala Val Phe Gly Gly Gly Thr His Leu Thr
            115                 120                 125 gtc ctc ggt cag ccc aag gcc tcc ccc tcg gtc aca ctc ttc ccg ccc      433
Val Leu Gly Gln Pro Lys Ala Ser Pro Ser Val Thr Leu Phe Pro Pro
130                 135                 140 tcc tct gag gag ctc ggc gcc aac aag gcc acc ctg gtg tgc ctc atc      481
Ser Ser Glu Glu Leu Gly Ala Asn Lys Ala Thr Leu Val Cys Leu Ile
145                 150                 155                 160 agc gac ttc tac ccc agc ggc gtg acg gtg gcc tgg aag gca gac ggc      529
Ser Asp Phe Tyr Pro Ser Gly Val Thr Val Ala Trp Lys Ala Asp Gly
                165                 170                 175 agc ccc gtc acc cag ggc gtg gag acc acc aag ccc tcc aag cag agc      577
Ser Pro Val Thr Gln Gly Val Glu Thr Thr Lys Pro Ser Lys Gln Ser
            180                 185                 190 aac aac aag tac gcg gcc agc agc tac ctg agc ctg acg cct gac aag      625
Asn Asn Lys Tyr Ala Ala Ser Ser Tyr Leu Ser Leu Thr Pro Asp Lys
            195                 200                 205 tgg aaa tct cac agc agc ttc agc tgc ctg gtc acg cac gag ggg agc      673
Trp Lys Ser His Ser Ser Phe Ser Cys Leu Val Thr His Glu Gly Ser
210                 215                 220 acc gtg gag aag aag gtg gcc ccc gca gag tgc tct tag gttcccgacg       722
Thr Val Glu Lys Lys Val Ala Pro Ala Glu Cys Ser
225                 230                 235 gccccgccca ccgaaggggg cccggagcct caggacctcc aggaggatct tgcctcccat    782
ctgggtcatc ccgcccttct ccccgcaccc aggcagcact caataaagtg ttctttgttc    842
aatcagaaaa aaaaaa                                                    858

<210> SEQ ID NO 41
<211> LENGTH: 236
<212> TYPE: PRT
<213> ORGANISM: Canis familiaris

<400> SEQUENCE: 41

Ser Asn Met Ala Trp Ser Pro Leu Leu Thr Leu Leu Ala Tyr Cys
 1               5                  10                  15

Thr Gly Ser Trp Ala Gln Ser Val Leu Thr Gln Pro Thr Ser Val Ser
             20                  25                  30

Gly Ser Leu Gly Gln Arg Val Thr Ile Ser Cys Ser Gly Ser Thr Asn
             35                  40                  45

Asn Ile Gly Ile Val Gly Ala Ser Trp Tyr Gln Gln Leu Pro Gly Lys
 50                  55                  60

Ala Pro Lys Leu Leu Val Tyr Ser Val Gly Asp Arg Pro Ser Gly Val
 65                  70                  75                  80
```

```
Pro Asp Arg Phe Ser Gly Ser Asn Ser Gly Asn Ser Ala Thr Leu Thr
                85                  90                  95

Ile Thr Gly Leu Gln Ala Glu Asp Glu Ala Asp Tyr Tyr Cys Gln Ser
            100                 105                 110

Phe Asp Thr Thr Leu Gly Ala Val Phe Gly Gly Gly Thr His Leu Thr
        115                 120                 125

Val Leu Gly Gln Pro Lys Ala Ser Pro Ser Val Thr Leu Phe Pro Pro
130                 135                 140

Ser Ser Glu Glu Leu Gly Ala Asn Lys Ala Thr Leu Val Cys Leu Ile
145                 150                 155                 160

Ser Asp Phe Tyr Pro Ser Gly Val Thr Val Ala Trp Lys Ala Asp Gly
                165                 170                 175

Ser Pro Val Thr Gln Gly Val Glu Thr Thr Lys Pro Ser Lys Gln Ser
            180                 185                 190

Asn Asn Lys Tyr Ala Ala Ser Ser Tyr Leu Ser Leu Thr Pro Asp Lys
        195                 200                 205

Trp Lys Ser His Ser Ser Phe Ser Cys Leu Val Thr His Glu Gly Ser
    210                 215                 220

Thr Val Glu Lys Lys Val Ala Pro Ala Glu Cys Ser
225                 230                 235

<210> SEQ ID NO 42
<211> LENGTH: 514
<212> TYPE: DNA
<213> ORGANISM: Canis familiaris
<220> FEATURE:
<221> NAME/KEY: CDS
<222> LOCATION: (1)..(381)
<223> OTHER INFORMATION:

<400> SEQUENCE: 42 atg ttc gag gct gtg tca cag tgt gct gtg ttc ggc gga ggc acc cac      48
Met Phe Glu Ala Val Ser Gln Cys Ala Val Phe Gly Gly Gly Thr His
1               5                   10                  15 ctg acc gtc ctc ggt cag ccc aag gcc tcc ccc tcg gtc aca ctc ttc      96
Leu Thr Val Leu Gly Gln Pro Lys Ala Ser Pro Ser Val Thr Leu Phe
            20                  25                  30 ccg ccc tcc tct gag gag ctc ggc gcc aac aag gcc acc ctg gtg tgc     144
Pro Pro Ser Ser Glu Glu Leu Gly Ala Asn Lys Ala Thr Leu Val Cys
        35                  40                  45 ctc atc agc gac ttc tac ccc agc ggc gtg acg gtg gcc tgg aag gca     192
Leu Ile Ser Asp Phe Tyr Pro Ser Gly Val Thr Val Ala Trp Lys Ala
    50                  55                  60 gac ggc agc ccc gtc acc cag ggc gtg gag acc acc aag ccc tcc aag     240
Asp Gly Ser Pro Val Thr Gln Gly Val Glu Thr Thr Lys Pro Ser Lys
65                  70                  75                  80 cag agc aac aac aag tac gcg gcc agc agc tac ctg agc ctg acg cct     288
Gln Ser Asn Asn Lys Tyr Ala Ala Ser Ser Tyr Leu Ser Leu Thr Pro
                85                  90                  95 gac aag tgg aaa tct cac agc agc ttc agc tgc ctg gtc acg cac gag     336
Asp Lys Trp Lys Ser His Ser Ser Phe Ser Cys Leu Val Thr His Glu
            100                 105                 110 ggg agc acc gtg gag aag aag gtg gcc ccc gca gag tgc tct tag         381
Gly Ser Thr Val Glu Lys Lys Val Ala Pro Ala Glu Cys Ser
        115                 120                 125 gttcccgacg gccccgccca ccgaagggggg cccggagcct caggacctcc aggaggatct   441
tgcctcccat ctgggtcatc ccgcccttct ccccgcaccc aggcagcact caataaagtg    501
```
ttctttgttc aat 514

<210> SEQ ID NO 43
<211> LENGTH: 126
<212> TYPE: PRT
<213> ORGANISM: Canis familiaris

<400> SEQUENCE: 43

```
Met Phe Glu Ala Val Ser Gln Cys Ala Val Phe Gly Gly Gly Thr His
1               5                   10                  15

Leu Thr Val Leu Gly Gln Pro Lys Ala Ser Pro Ser Val Thr Leu Phe
            20                  25                  30

Pro Pro Ser Ser Glu Glu Leu Gly Ala Asn Lys Ala Thr Leu Val Cys
        35                  40                  45

Leu Ile Ser Asp Phe Tyr Pro Ser Gly Val Thr Val Ala Trp Lys Ala
    50                  55                  60

Asp Gly Ser Pro Val Thr Gln Gly Val Glu Thr Thr Lys Pro Ser Lys
65                  70                  75                  80

Gln Ser Asn Asn Lys Tyr Ala Ala Ser Ser Tyr Leu Ser Leu Thr Pro
                85                  90                  95

Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
        115                 120                 125
```

<210> SEQ ID NO 44
<211> LENGTH: 514
<212> TYPE: DNA
<213> ORGANISM: Canis familiaris
<220> FEATURE:
<221> NAME/KEY: CDS
<222> LOCATION: (1)..(381)
<223> OTHER INFORMATION:

<400> SEQUENCE: 44

```
atg ttc gag gct gtg tca cag tgt gct gtg ttc ggc gga ggc acc cac    48
Met Phe Glu Ala Val Ser Gln Cys Ala Val Phe Gly Gly Gly Thr His
1               5                   10                  15 ctg acc gtc ctc ggt cag ccc aag gcc tcc ccc tcg gtc aca ctc ttc    96
Leu Thr Val Leu Gly Gln Pro Lys Ala Ser Pro Ser Val Thr Leu Phe
            20                  25                  30 ccg ccc tcc tct gag gag ctc ggc gcc aac aag gcc acc ctg gtg tgc    144
Pro Pro Ser Ser Glu Glu Leu Gly Ala Asn Lys Ala Thr Leu Val Cys
        35                  40                  45 ctc atc agc gac ttc tac ccc agc ggc gtg acg gtg gcc tgg aag gca    192
Leu Ile Ser Asp Phe Tyr Pro Ser Gly Val Thr Val Ala Trp Lys Ala
    50                  55                  60 gac ggc agc ccc gtc acc cag ggc gtg gag acc acc aag ccc tcc aag    240
Asp Gly Ser Pro Val Thr Gln Gly Val Glu Thr Thr Lys Pro Ser Lys
65                  70                  75                  80 cag agc aac aac aag tac gcg gcc agc agc tac ctg agc ctg acg cct    288
Gln Ser Asn Asn Lys Tyr Ala Ala Ser Ser Tyr Leu Ser Leu Thr Pro
                85                  90                  95 gac aag tgg aaa tct cac agc agc ttc agc tgc ctg gtc acg cac gag    336
Asp Lys Trp Lys Ser His Ser Ser Phe Ser Cys Leu Val Thr His Glu
            100                 105                 110 ggg agc acc gtg gag aag aag gtg gcc ccc gca gag tgc tct tag        381
Gly Ser Thr Val Glu Lys Lys Val Ala Pro Ala Glu Cys Ser
        115                 120                 125 gttcccgacg gccccgccca ccgaagggg cccggagcct caggacctcc aggaggatct    441
```

```
tgcctcccat ctgggtcatc ccgctcttct ccccgcaccc aggcagcact caataaagtg      501
ttctttgttc aat                                                        514

<210> SEQ ID NO 45
<211> LENGTH: 126
<212> TYPE: PRT
<213> ORGANISM: Canis familiaris

<400> SEQUENCE: 45

Met Phe Glu Ala Val Ser Gln Cys Ala Val Phe Gly Gly Thr His
1               5                   10                  15

Leu Thr Val Leu Gly Gln Pro Lys Ala Ser Pro Ser Val Thr Leu Phe
            20                  25                  30

Pro Pro Ser Ser Glu Glu Leu Gly Ala Asn Lys Ala Thr Leu Val Cys
        35                  40                  45

Leu Ile Ser Asp Phe Tyr Pro Ser Gly Val Thr Val Ala Trp Lys Ala
    50                  55                  60

Asp Gly Ser Pro Val Thr Gln Gly Val Glu Thr Thr Lys Pro Ser Lys
65                  70                  75                  80

Gln Ser Asn Asn Lys Tyr Ala Ala Ser Ser Tyr Leu Ser Leu Thr Pro
                85                  90                  95

Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
        115                 120                 125

<210> SEQ ID NO 46
<211> LENGTH: 561
<212> TYPE: DNA
<213> ORGANISM: Canis familiaris
<220> FEATURE:
<221> NAME/KEY: CDS
<222> LOCATION: (1)..(426)
<223> OTHER INFORMATION:

<400> SEQUENCE: 46 atg ggc ctg ggg cag ggg agg ggc tgc agg ggt gac aga ggg ttt gtg      48
Met Gly Leu Gly Gln Gly Arg Gly Cys Arg Gly Asp Arg Gly Phe Val
1               5                   10                  15 ttc aag gct gta tca ctg tgt tac gtg ttc ggc tca gga acc caa ctg      96
Phe Lys Ala Val Ser Leu Cys Tyr Val Phe Gly Ser Gly Thr Gln Leu
            20                  25                  30 acc gtc ctt ggt cag ccc aag gcc tcc ccc tcg gtc aca ctc ttc ccg      144
Thr Val Leu Gly Gln Pro Lys Ala Ser Pro Ser Val Thr Leu Phe Pro
        35                  40                  45 ccc tcc tct gag gag ctc ggc gcc aac aag gcc acc ctg gtg tgc ctc      192
Pro Ser Ser Glu Glu Leu Gly Ala Asn Lys Ala Thr Leu Val Cys Leu
    50                  55                  60 atc agc gac ttc tac ccc agc ggc gtg acg gtg gcc tgg aag gca gac      240
Ile Ser Asp Phe Tyr Pro Ser Gly Val Thr Val Ala Trp Lys Ala Asp
65                  70                  75                  80 ggc agc ccc atc acc cag ggc gtg gag acc acc aag ccc tcc aag cag      288
Gly Ser Pro Ile Thr Gln Gly Val Glu Thr Thr Lys Pro Ser Lys Gln
                85                  90                  95 agc aac aac aag tac gcg gcc agc agc tac ctg agc ctg acg cct gac      336
Ser Asn Asn Lys Tyr Ala Ala Ser Ser Tyr Leu Ser Leu Thr Pro Asp
            100                 105                 110 aag tgg aaa tct cac agc agc ttc agc tgc ctg gtc acg cac gag ggg      384
Lys Trp Lys Ser His Ser Ser Phe Ser Cys Leu Val Thr His Glu Gly
```

```
                 115                 120                 125
agc act gtg gag aag aag gtg gcc ccc gca gag tgc tct tag              426
Ser Thr Val Glu Lys Lys Val Ala Pro Ala Glu Cys Ser
    130                 135                 140 gttcccgatg cccccgccc accgaagggg gctcggagcc tcaggacctc caggaggatc     486
ttgcctccca tctgggtctt cccagccctt ttccccacac tcaggcaaca ctcaataaag   546
tgtcctttat tcaat                                                     561

<210> SEQ ID NO 47
<211> LENGTH: 141
<212> TYPE: PRT
<213> ORGANISM: Canis familiaris

<400> SEQUENCE: 47

Met Gly Leu Gly Gln Gly Arg Gly Cys Arg Gly Asp Arg Gly Phe Val
1               5                   10                  15

Phe Lys Ala Val Ser Leu Cys Tyr Val Phe Gly Ser Gly Thr Gln Leu
                20                  25                  30

Thr Val Leu Gly Gln Pro Lys Ala Ser Pro Ser Val Thr Leu Phe Pro
            35                  40                  45

Pro Ser Ser Glu Glu Leu Gly Ala Asn Lys Ala Thr Leu Val Cys Leu
        50                  55                  60

Ile Ser Asp Phe Tyr Pro Ser Gly Val Thr Val Ala Trp Lys Ala Asp
65                  70                  75                  80

Gly Ser Pro Ile Thr Gln Gly Val Glu Thr Thr Lys Pro Ser Lys Gln
                85                  90                  95

Ser Asn Asn Lys Tyr Ala Ala Ser Ser Tyr Leu Ser Leu Thr Pro Asp
                100                 105                 110

Lys Trp Lys Ser His Ser Ser Phe Ser Cys Leu Val Thr His Glu Gly
            115                 120                 125

Ser Thr Val Glu Lys Lys Val Ala Pro Ala Glu Cys Ser
        130                 135                 140

<210> SEQ ID NO 48
<211> LENGTH: 514
<212> TYPE: DNA
<213> ORGANISM: Canis familiaris
<220> FEATURE:
<221> NAME/KEY: CDS
<222> LOCATION: (1)..(381)
<223> OTHER INFORMATION:

<400> SEQUENCE: 48 atg ttc gag gct gtg tca cag tgt gct gtg ttc ggc gga ggc acc cac    48
Met Phe Glu Ala Val Ser Gln Cys Ala Val Phe Gly Gly Gly Thr His
1               5                   10                  15 ctg acc gtc ctc ggt cag ccc aag gcc tcc ccc tcg gtc aca ctc ttc    96
Leu Thr Val Leu Gly Gln Pro Lys Ala Ser Pro Ser Val Thr Leu Phe
                20                  25                  30 ccg ccc tcc tct gag gag ctc ggc gcc aac aag gcc acc ctg gtg tgc    144
Pro Pro Ser Ser Glu Glu Leu Gly Ala Asn Lys Ala Thr Leu Val Cys
            35                  40                  45 ctc atc agc gac ttc tac ccc agc ggc gtg acg gtg gcc tgg aag gca    192
Leu Ile Ser Asp Phe Tyr Pro Ser Gly Val Thr Val Ala Trp Lys Ala
        50                  55                  60 gac ggc agc ccc gtc acc cag ggc gtg gag acc acc aag ccc tcc aag    240
Asp Gly Ser Pro Val Thr Gln Gly Val Glu Thr Thr Lys Pro Ser Lys
65                  70                  75                  80
```

```
cag agc aac aac aag tac gcg gcc agc agc tac ctg agc ctg acg cct      288
Gln Ser Asn Asn Lys Tyr Ala Ala Ser Ser Tyr Leu Ser Leu Thr Pro
                85                  90                  95 gac aag tgg aaa tct cac agc agc ttc agc tgc ctg gtc acg cac gag      336
Asp Lys Trp Lys Ser His Ser Ser Phe Ser Cys Leu Val Thr His Glu
            100                 105                 110 ggg agc acc gtg gag aag aag gtg gcc ccc gca gag tgc tct tag          381
Gly Ser Thr Val Glu Lys Lys Val Ala Pro Ala Glu Cys Ser
        115                 120                 125 gttcccgacg gccccgccca cctaaggggg cccggagcct caggacctcc aggaggatct    441
tgcctcccat ctgggtcatc ccgctcttct ccccgcaccc aggcagcact caataaagtg    501
ttctttgttc aat                                                       514
```

```
<210> SEQ ID NO 49
<211> LENGTH: 126
<212> TYPE: PRT
<213> ORGANISM: Canis familiaris

<400> SEQUENCE: 49

Met Phe Glu Ala Val Ser Gln Cys Ala Val Phe Gly Gly Gly Thr His
1               5                   10                  15

Leu Thr Val Leu Gly Gln Pro Lys Ala Ser Pro Ser Val Thr Leu Phe
            20                  25                  30

Pro Pro Ser Ser Glu Glu Leu Gly Ala Asn Lys Ala Thr Leu Val Cys
        35                  40                  45

Leu Ile Ser Asp Phe Tyr Pro Ser Gly Val Thr Val Ala Trp Lys Ala
    50                  55                  60

Asp Gly Ser Pro Val Thr Gln Gly Val Glu Thr Thr Lys Pro Ser Lys
65                  70                  75                  80

Gln Ser Asn Asn Lys Tyr Ala Ala Ser Ser Tyr Leu Ser Leu Thr Pro
                85                  90                  95

Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
        115                 120                 125
```

```
<210> SEQ ID NO 50
<211> LENGTH: 514
<212> TYPE: DNA
<213> ORGANISM: Canis familiaris
<220> FEATURE:
<221> NAME/KEY: CDS
<222> LOCATION: (1)..(381)
<223> OTHER INFORMATION:

<400> SEQUENCE: 50 atg ttc gag gct gtg tca cag tgt gct gtg ttc ggc gga ggc acc cac       48
Met Phe Glu Ala Val Ser Gln Cys Ala Val Phe Gly Gly Gly Thr His
1               5                   10                  15 ctg acc gtc ctc ggt cag ccc aag gcc tcc ccc tcg gtc aca ctc ttc       96
Leu Thr Val Leu Gly Gln Pro Lys Ala Ser Pro Ser Val Thr Leu Phe
            20                  25                  30 ccg ccc tcc tct gag gag ctc ggc gcc aac aag gcc acc ctg gtg tgc      144
Pro Pro Ser Ser Glu Glu Leu Gly Ala Asn Lys Ala Thr Leu Val Cys
        35                  40                  45 ctc atc agc gac ttc tac ccc agc ggc gtg acg gtg gcc tgg aag gca      192
Leu Ile Ser Asp Phe Tyr Pro Ser Gly Val Thr Val Ala Trp Lys Ala
    50                  55                  60 gac ggc agc ccc gtc acc cag ggc gtg gag acc acc aag ccc tcc aag      240
```

```
Asp Gly Ser Pro Val Thr Gln Gly Val Glu Thr Thr Lys Pro Ser Lys
 65                  70                  75                  80 cag agc aac aac aag tac gcg gcc agc agc tac ctg agc ctg acg cct       288
Gln Ser Asn Asn Lys Tyr Ala Ala Ser Ser Tyr Leu Ser Leu Thr Pro
                 85                  90                  95 gac aag tgg aaa tct cac agc agc ttc agc tgc ctg gtc acg cac gag       336
Asp Lys Trp Lys Ser His Ser Ser Phe Ser Cys Leu Val Thr His Glu
            100                 105                 110 ggg agc acc gtg gag aag aag gtg gcc ccc gca gag tgc tct tag           381
Gly Ser Thr Val Glu Lys Lys Val Ala Pro Ala Glu Cys Ser
        115                 120                 125 gttcccgacg ccccgcccca ccgaaggggg cccggagcct caggacctcc aggaggatct     441
tgcctcccat ctgggtcatc ccgctcttct ccccgcaccc aggcagcact caataaagtg    501
ttctttgttc aat                                                        514

<210> SEQ ID NO 51
<211> LENGTH: 126
<212> TYPE: PRT
<213> ORGANISM: Canis familiaris

<400> SEQUENCE: 51

Met Phe Glu Ala Val Ser Gln Cys Ala Val Phe Gly Gly Gly Thr His
 1               5                  10                  15

Leu Thr Val Leu Gly Gln Pro Lys Ala Ser Pro Ser Val Thr Leu Phe
            20                  25                  30

Pro Pro Ser Ser Glu Glu Leu Gly Ala Asn Lys Ala Thr Leu Val Cys
        35                  40                  45

Leu Ile Ser Asp Phe Tyr Pro Ser Gly Val Thr Val Ala Trp Lys Ala
 50                  55                  60

Asp Gly Ser Pro Val Thr Gln Gly Val Glu Thr Thr Lys Pro Ser Lys
 65                  70                  75                  80

Gln Ser Asn Asn Lys Tyr Ala Ala Ser Ser Tyr Leu Ser Leu Thr Pro
                 85                  90                  95

Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
        115                 120                 125

<210> SEQ ID NO 52
<211> LENGTH: 697
<212> TYPE: DNA
<213> ORGANISM: Canis familiaris
<220> FEATURE:
<221> NAME/KEY: CDS
<222> LOCATION: (1)..(564)
<223> OTHER INFORMATION:

<400> SEQUENCE: 52 atg ggc aca cat ggt gac tac caa tca cgg tta gaa ttt caa cca cct        48
Met Gly Thr His Gly Asp Tyr Gln Ser Arg Leu Glu Phe Gln Pro Pro
 1               5                  10                  15 gaa tgg tgg gct act ctc aga aat gat cgg gaa aag ctg gag gat ggg        96
Glu Trp Trp Ala Thr Leu Arg Asn Asp Arg Glu Lys Leu Glu Asp Gly
            20                  25                  30 act ctc aga atc cca cgg tgg cac atg aac aaa tac cta gtc acg aca       144
Thr Leu Arg Ile Pro Arg Trp His Met Asn Lys Tyr Leu Val Thr Thr
        35                  40                  45 gtc ccc gta gag cca gcc agt ctc aaa gag gtg gcc agg aag att ccg       192
Val Pro Val Glu Pro Ala Ser Leu Lys Glu Val Ala Arg Lys Ile Pro
```

```
                  50                  55                  60
atc cat gat gaa tgt ggt gtg ttc ggc gga ggc acc cac ctg acc gtc     240
Ile His Asp Glu Cys Gly Val Phe Gly Gly Gly Thr His Leu Thr Val
 65                  70                  75                  80 ctc ggt cag ccc aag gcc tcc ccc tcg gtc aca ctc ttc ccg ccc tcc     288
Leu Gly Gln Pro Lys Ala Ser Pro Ser Val Thr Leu Phe Pro Pro Ser
                     85                  90                  95 tct gag gag ctc ggc gcc aac aag gcc acc ctg gtg tgc ctc atc agc     336
Ser Glu Glu Leu Gly Ala Asn Lys Ala Thr Leu Val Cys Leu Ile Ser
            100                 105                 110 gac ttc tac ccc agc ggt gtg acg gtg gcc tgg aag gca gac ggc agc     384
Asp Phe Tyr Pro Ser Gly Val Thr Val Ala Trp Lys Ala Asp Gly Ser
        115                 120                 125 ccc gtc acc cag ggc gtg gag acc acc aag ccc tcc aag cag agc aac     432
Pro Val Thr Gln Gly Val Glu Thr Thr Lys Pro Ser Lys Gln Ser Asn
    130                 135                 140 aac aag tac gcg gcc agc agc tac ctg agc ctg acg cct gac aag tgg     480
Asn Lys Tyr Ala Ala Ser Ser Tyr Leu Ser Leu Thr Pro Asp Lys Trp
145                 150                 155                 160 aaa tct cac agc agc ttc agc tgc ctg gtc acg cac gag ggg agc acc     528
Lys Ser His Ser Ser Phe Ser Cys Leu Val Thr His Glu Gly Ser Thr
                    165                 170                 175 gtg gag aag aag gtg gcc ccc gca gag tgc tct tag gttcccgacg          574
Val Glu Lys Lys Val Ala Pro Ala Glu Cys Ser
                180                 185 gccccgccca ccgaagggg cccggagcct caggacctcc aggaggatct tgcctcccat    634
ctgggtcatc ccgcccttct ccccgcaccc aggcagcact caataaagtg ttctttgttc    694
aat                                                                  697

<210> SEQ ID NO 53
<211> LENGTH: 187
<212> TYPE: PRT
<213> ORGANISM: Canis familiaris

<400> SEQUENCE: 53

Met Gly Thr His Gly Asp Tyr Gln Ser Arg Leu Glu Phe Gln Pro Pro
 1               5                  10                  15

Glu Trp Trp Ala Thr Leu Arg Asn Asp Arg Glu Lys Leu Glu Asp Gly
            20                  25                  30

Thr Leu Arg Ile Pro Arg Trp His Met Asn Lys Tyr Leu Val Thr Thr
        35                  40                  45

Val Pro Val Glu Pro Ala Ser Leu Lys Glu Val Ala Arg Lys Ile Pro
    50                  55                  60

Ile His Asp Glu Cys Gly Val Phe Gly Gly Gly Thr His Leu Thr Val
 65                  70                  75                  80

Leu Gly Gln Pro Lys Ala Ser Pro Ser Val Thr Leu Phe Pro Pro Ser
                     85                  90                  95

Ser Glu Glu Leu Gly Ala Asn Lys Ala Thr Leu Val Cys Leu Ile Ser
            100                 105                 110

Asp Phe Tyr Pro Ser Gly Val Thr Val Ala Trp Lys Ala Asp Gly Ser
        115                 120                 125

Pro Val Thr Gln Gly Val Glu Thr Thr Lys Pro Ser Lys Gln Ser Asn
    130                 135                 140

Asn Lys Tyr Ala Ala Ser Ser Tyr Leu Ser Leu Thr Pro Asp Lys Trp
145                 150                 155                 160

Lys Ser His Ser Ser Phe Ser Cys Leu Val Thr His Glu Gly Ser Thr
```

```
                        165                 170                 175
Val Glu Lys Lys Val Ala Pro Ala Glu Cys Ser
                180                 185

<210> SEQ ID NO 54
<211> LENGTH: 634
<212> TYPE: DNA
<213> ORGANISM: Canis familiaris
<220> FEATURE:
<221> NAME/KEY: CDS
<222> LOCATION: (1)..(501)
<223> OTHER INFORMATION:

<400> SEQUENCE: 54 atg gaa atg aaa ttc ctg gac ccc agt ggc tat gcc ctc atc acc caa      48
Met Glu Met Lys Phe Leu Asp Pro Ser Gly Tyr Ala Leu Ile Thr Gln
1               5                   10                  15 ccc ccc ttc aac ccg acc agt acc cgt gac aag ggg gct gcc ctt tgg      96
Pro Pro Phe Asn Pro Thr Ser Thr Arg Asp Lys Gly Ala Ala Leu Trp
                20                  25                  30 gcc tcc cga gca gct gca ggg ttt gtg ctc gag gct gtg tca cag tgt     144
Ala Ser Arg Ala Ala Ala Gly Phe Val Leu Glu Ala Val Ser Gln Cys
            35                  40                  45 att gtg ttc ggc gga ggc acc cat ctg acc gtc ctc ggt cag ccc aag     192
Ile Val Phe Gly Gly Gly Thr His Leu Thr Val Leu Gly Gln Pro Lys
        50                  55                  60 gcc tcc cct tcg gtc aca ctc ttc ccg ccc tcc tct gag gag ctt ggc     240
Ala Ser Pro Ser Val Thr Leu Phe Pro Pro Ser Ser Glu Glu Leu Gly
65                  70                  75                  80 gcc aac aag gcc acc ctg gtg tgc ctc atc agc gac ttc tac ccc agc     288
Ala Asn Lys Ala Thr Leu Val Cys Leu Ile Ser Asp Phe Tyr Pro Ser
                85                  90                  95 ggc gtg aca gtg gcc tgg aag gca gac ggc agc ccc atc acc cag ggt     336
Gly Val Thr Val Ala Trp Lys Ala Asp Gly Ser Pro Ile Thr Gln Gly
                100                 105                 110 gtg gag acc acc aag ccc tcc aag cag agc aac aac aag tac gcg gcc     384
Val Glu Thr Thr Lys Pro Ser Lys Gln Ser Asn Asn Lys Tyr Ala Ala
            115                 120                 125 agc agc tac ctg agc ctg acg cct gac aag tgg aaa tct cac agc agc     432
Ser Ser Tyr Leu Ser Leu Thr Pro Asp Lys Trp Lys Ser His Ser Ser
        130                 135                 140 ttc agc tgc ctg gtc acg cac gag ggg agc acc gtg gag aag aag gtg     480
Phe Ser Cys Leu Val Thr His Glu Gly Ser Thr Val Glu Lys Lys Val
145                 150                 155                 160 gcc ccc gca gag tgc tct tag gttcctgatg tcccccgccc accaagggg         531
Ala Pro Ala Glu Cys Ser
                165 gctcagagcc tcaggacctc caggaggatc ttgcctccca tctgggtcat cccagccttt    591 cccttaaac ccaggcaaca ttcaataaag tgttctttct tca                        634

<210> SEQ ID NO 55
<211> LENGTH: 166
<212> TYPE: PRT
<213> ORGANISM: Canis familiaris

<400> SEQUENCE: 55

Met Glu Met Lys Phe Leu Asp Pro Ser Gly Tyr Ala Leu Ile Thr Gln
1               5                   10                  15

Pro Pro Phe Asn Pro Thr Ser Thr Arg Asp Lys Gly Ala Ala Leu Trp
                20                  25                  30
```

Ala Ser Arg Ala Ala Ala Gly Phe Val Leu Glu Ala Val Ser Gln Cys
     35                  40                  45

Ile Val Phe Gly Gly Thr His Leu Thr Val Leu Gly Gln Pro Lys
 50                  55                  60

Ala Ser Pro Ser Val Thr Leu Phe Pro Pro Ser Ser Glu Glu Leu Gly
 65                  70                  75                  80

Ala Asn Lys Ala Thr Leu Val Cys Leu Ile Ser Asp Phe Tyr Pro Ser
                 85                  90                  95

Gly Val Thr Val Ala Trp Lys Ala Asp Gly Ser Pro Ile Thr Gln Gly
             100                 105                 110

Val Glu Thr Thr Lys Pro Ser Lys Gln Ser Asn Asn Lys Tyr Ala Ala
             115                 120                 125

Ser Ser Tyr Leu Ser Leu Thr Pro Asp Lys Trp Lys Ser His Ser Ser
 130                 135                 140

Phe Ser Cys Leu Val Thr His Glu Gly Ser Thr Val Glu Lys Lys Val
145                 150                 155                 160

Ala Pro Ala Glu Cys Ser
                165

<210> SEQ ID NO 56
<211> LENGTH: 551
<212> TYPE: DNA
<213> ORGANISM: Canis familiaris
<220> FEATURE:
<221> NAME/KEY: CDS
<222> LOCATION: (39)..(419)
<223> OTHER INFORMATION:

<400> SEQUENCE: 56
ggtcatggat atgacacagc tgtaccccca caccaaga atg agg cag ttg ctg aca      56
                                         Met Arg Gln Leu Leu Thr
                                          1               5 caa caa aca tct gcc ttg acc cgc tgt cct tcc atc ccc aca ggt cag     104
Gln Gln Thr Ser Ala Leu Thr Arg Cys Pro Ser Ile Pro Thr Gly Gln
         10                  15                  20 ccc aag gcc tcc ccc tcg gtc aca ctc ttc ccg ccc tcc tct gag gag     152
Pro Lys Ala Ser Pro Ser Val Thr Leu Phe Pro Pro Ser Ser Glu Glu
     25                  30                  35 ctc ggc gcc aac aag gcc acc ctg gtg tgc ctc atc agc gac ttc tac     200
Leu Gly Ala Asn Lys Ala Thr Leu Val Cys Leu Ile Ser Asp Phe Tyr
 40                  45                  50 ccc agt ggc gtg acg gtg gcc tgg aag gca gac ggc agc ccc gtc acc     248
Pro Ser Gly Val Thr Val Ala Trp Lys Ala Asp Gly Ser Pro Val Thr
 55                  60                  65                  70 cag ggc gtg gag acc acc aag ccc tcc aag cag agc aac aac aag tac     296
Gln Gly Val Glu Thr Thr Lys Pro Ser Lys Gln Ser Asn Asn Lys Tyr
                 75                  80                  85 gcg gcc agc agc tac ctg agc ctg acg cct gac aag tgg aaa tct cac     344
Ala Ala Ser Ser Tyr Leu Ser Leu Thr Pro Asp Lys Trp Lys Ser His
             90                  95                 100 agc agc ttc agc tgc ctg gtc aca cac gag ggg agc acc gtg gag aag     392
Ser Ser Phe Ser Cys Leu Val Thr His Glu Gly Ser Thr Val Glu Lys
         105                 110                 115 aag gtg gcc ccc gca gag tgc tct tag gttcccgacg ccccgccca             439
Lys Val Ala Pro Ala Glu Cys Ser
         120                 125 cctaaggggg cccggagcct caggacctcc aggaggatct tgcctcctat ctgggtcatc    499
ccgcccttct ccccacaccc aggcagcact caataaagtg ttctttgttc aa            551

<210> SEQ ID NO 57
<211> LENGTH: 126
<212> TYPE: PRT
<213> ORGANISM: Canis familiaris

<400> SEQUENCE: 57

Met Arg Gln Leu Leu Thr Gln Gln Thr Ser Ala Leu Thr Arg Cys Pro
1               5                   10                  15

Ser Ile Pro Thr Gly Gln Pro Lys Ala Ser Pro Ser Val Thr Leu Phe
            20                  25                  30

Pro Pro Ser Ser Glu Glu Leu Gly Ala Asn Lys Ala Thr Leu Val Cys
        35                  40                  45

Leu Ile Ser Asp Phe Tyr Pro Ser Gly Val Thr Val Ala Trp Lys Ala
    50                  55                  60

Asp Gly Ser Pro Val Thr Gln Gly Val Glu Thr Thr Lys Pro Ser Lys
65                  70                  75                  80

Gln Ser Asn Asn Lys Tyr Ala Ala Ser Ser Tyr Leu Ser Leu Thr Pro
                85                  90                  95

Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
        115                 120                 125

<210> SEQ ID NO 58
<211> LENGTH: 864
<212> TYPE: DNA
<213> ORGANISM: Canis familiaris
<220> FEATURE:
<221> NAME/KEY: CDS
<222> LOCATION: (1)..(702)
<223> OTHER INFORMATION:

<400> SEQUENCE: 58 atg gcc tgg acc ctt ctt ctc ctt gga ttc ctg gct cac tgc aca ggt    48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc    96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg   144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg   192
Lys Asp Val His Trp Tyr Gln Gln Lys Pro Gly Gln Ala Pro Leu Leu
    50                  55                  60 att atc tat aat gat aac agc cag ccc tca ggg atc cct gag cga ttc   240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc   288
Ser Gly Thr Asn Ser Gly Ser Thr Ala Thr Leu Thr Ile Ser Glu Ala
                85                  90                  95 caa acc aac gat gag gct gac tat tac tgc cag gtg tgg gaa agt agc   336
Gln Thr Asn Asp Glu Ala Asp Tyr Tyr Cys Gln Val Trp Glu Ser Ser
            100                 105                 110 gct gat tgt tgg gta ttc ggt gaa ggg acc cag ctg acc gtc ctc ggt   384
Ala Asp Cys Trp Val Phe Gly Glu Gly Thr Gln Leu Thr Val Leu Gly
        115                 120                 125 cag ccc aag tcc tcc ccc ttg gtc aca ctc ttc ccg ccc tcc tct gag   432
Gln Pro Lys Ser Ser Pro Leu Val Thr Leu Phe Pro Pro Ser Ser Glu
    130                 135                 140

```
gag ctc ggc gcc aac aag gct acc ctg gtg tgc ctc atc agc gac ttc      480
Glu Leu Gly Ala Asn Lys Ala Thr Leu Val Cys Leu Ile Ser Asp Phe
145                 150                 155                 160 tac ccc agt ggc ctg aaa gtg gct tgg aag gca gat ggc agc acc atc      528
Tyr Pro Ser Gly Leu Lys Val Ala Trp Lys Ala Asp Gly Ser Thr Ile
                165                 170                 175 atc cag ggc gtg gaa acc acc aag ccc tcc aag cag agc aac aac aag      576
Ile Gln Gly Val Glu Thr Thr Lys Pro Ser Lys Gln Ser Asn Asn Lys
            180                 185                 190 tac acg gcc agc agc tac ctg agc ctg acg cct gac aag tgg aaa tct      624
Tyr Thr Ala Ser Ser Tyr Leu Ser Leu Thr Pro Asp Lys Trp Lys Ser
        195                 200                 205 cac agc agc ttc agc tgc ctg gtc acg cac cag ggg agc acc gtg gag      672
His Ser Ser Phe Ser Cys Leu Val Thr His Gln Gly Ser Thr Val Glu
    210                 215                 220 aag aag gtg gcc cct gca gag tgc tct tag gtccctgaga attcctgaga        722
Lys Lys Val Ala Pro Ala Glu Cys Ser
225                 230 tggagccttc ctcacccaga caccccttcc ccagttcacc ttgtgcccct gaaaacccac    782
cctggaccag ctcagaccag gcaggtcact catcctccct gtttctactt gtgctcaata   842
aagactttat catttatcac tg                                             864

<210> SEQ ID NO 59
<211> LENGTH: 233
<212> TYPE: PRT
<213> ORGANISM: Canis familiaris

<400> SEQUENCE: 59

Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Trp Glu Ser Ser
            100                 105                 110

Ala Asp Cys Trp Val Phe Gly Glu Gly Thr Gln Leu Thr Val Leu Gly
        115                 120                 125

Gln Pro Lys Ser Ser Pro Leu Val Thr Leu Phe Pro Pro Ser Ser Glu
    130                 135                 140

Glu Leu Gly Ala Asn Lys Ala Thr Leu Val Cys Leu Ile Ser Asp Phe
145                 150                 155                 160

Tyr Pro Ser Gly Leu Lys Val Ala Trp Lys Ala Asp Gly Ser Thr Ile
                165                 170                 175

Ile Gln Gly Val Glu Thr Thr Lys Pro Ser Lys Gln Ser Asn Asn Lys
            180                 185                 190

Tyr Thr Ala Ser Ser Tyr Leu Ser Leu Thr Pro Asp Lys Trp Lys Ser
        195                 200                 205

His Ser Ser Phe Ser Cys Leu Val Thr His Gln Gly Ser Thr Val Glu
```

```
                      210                 215                 220
Lys Lys Val Ala Pro Ala Glu Cys Ser
225                 230

<210> SEQ ID NO 60
<211> LENGTH: 864
<212> TYPE: DNA
<213> ORGANISM: Canis familiaris
<220> FEATURE:
<221> NAME/KEY: CDS
<222> LOCATION: (1)..(702)
<223> OTHER INFORMATION:

<400> SEQUENCE: 60 atg gcc tgg acc ctt ctt ctc ctt gga ttc ctg gct cac tgc aca ggt       48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc       96
Ser Val Ala Ser Tyr Val Leu Thr Gln Ser Pro Ser Val Ser Val Thr
                20                  25                  30 ctg gga cag acg gcc agc atc acc tgt agg gga aac agc att gga agg      144
Leu Gly Gln Thr Ala Ser Ile Thr Cys Arg Gly Asn Ser Ile Gly Arg
            35                  40                  45 aaa gat gtt cat tgg tac cag cag aag ccg ggc caa gcc ccc ctg ctg      192
Lys Asp Val His Trp Tyr Gln Gln Lys Pro Gly Gln Ala Pro Leu Leu
        50                  55                  60 att atc tat aat gat aac agc cag ccc tca ggg atc cct gag cga ttc      240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc      288
Ser Gly Thr Asn Ser Gly Ser Thr Ala Thr Leu Thr Ile Ser Glu Ala
                85                  90                  95 caa acc aac gat gag gct gac tat tac tgc cag gtg tgg gaa agt agc      336
Gln Thr Asn Asp Glu Ala Asp Tyr Tyr Cys Gln Val Trp Glu Ser Ser
                100                 105                 110 gct gat gct cac aac aac tct gga aga aaa att gga gca cct ggc agt      384
Ala Asp Ala His Asn Asn Ser Gly Arg Lys Ile Gly Ala Pro Gly Ser
            115                 120                 125 cag ccc aag tcc tcc ccc ttg gtc aca ctc ttc ccg ccc tcc tct gag      432
Gln Pro Lys Ser Ser Pro Leu Val Thr Leu Phe Pro Pro Ser Ser Glu
        130                 135                 140 gag ctc ggc gcc aac aag gct acc ctg gtg tgc ctc atc agc gac ttc      480
Glu Leu Gly Ala Asn Lys Ala Thr Leu Val Cys Leu Ile Ser Asp Phe
145                 150                 155                 160 tac ccc agt ggc ctg aaa gtg gct tgg aag gca gat ggc agc acc atc      528
Tyr Pro Ser Gly Leu Lys Val Ala Trp Lys Ala Asp Gly Ser Thr Ile
                165                 170                 175 atc cag ggc gtg gaa acc acc aag ccc tcc aag cag agc aac aac aag      576
Ile Gln Gly Val Glu Thr Thr Lys Pro Ser Lys Gln Ser Asn Asn Lys
                180                 185                 190 tac acg gcc agc agc tac ctg agc ctg acg cct gac aag tgg aaa tct      624
Tyr Thr Ala Ser Ser Tyr Leu Ser Leu Thr Pro Asp Lys Trp Lys Ser
            195                 200                 205 cac agc agc ttc agc tgc ctg gtc acg cac cag ggg agc acc gtg gag      672
His Ser Ser Phe Ser Cys Leu Val Thr His Gln Gly Ser Thr Val Glu
        210                 215                 220 aag aag gtg gcc cct gca gag tgc tct tag gtccctgaga attcctgaga        722
Lys Lys Val Ala Pro Ala Glu Cys Ser
225                 230 tggagccttc ctcacccaga caccccttcc ccagttcacc ttgtgcccct gaaaacccac    782
```

```
cctggaccag ctcagaccag gcaggtcact catcctccct gtttctactt gtgctcaata    842
aagactttat catttatcac tg                                              864
```

<210> SEQ ID NO 61
<211> LENGTH: 233
<212> TYPE: PRT
<213> ORGANISM: Canis familiaris

<400> SEQUENCE: 61

```
Met Ala Trp Thr Leu Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Trp Glu Ser Ser
            100                 105                 110

Ala Asp Ala His Asn Asn Ser Gly Arg Lys Ile Gly Ala Pro Gly Ser
        115                 120                 125

Gln Pro Lys Ser Ser Pro Leu Val Thr Leu Phe Pro Pro Ser Ser Glu
    130                 135                 140

Glu Leu Gly Ala Asn Lys Ala Thr Leu Val Cys Leu Ile Ser Asp Phe
145                 150                 155                 160

Tyr Pro Ser Gly Leu Lys Val Ala Trp Lys Ala Asp Gly Ser Thr Ile
                165                 170                 175

Ile Gln Gly Val Glu Thr Thr Lys Pro Ser Lys Gln Ser Asn Asn Lys
            180                 185                 190

Tyr Thr Ala Ser Ser Tyr Leu Ser Leu Thr Pro Asp Lys Trp Lys Ser
        195                 200                 205

His Ser Ser Phe Ser Cys Leu Val Thr His Gln Gly Ser Thr Val Glu
    210                 215                 220

Lys Lys Val Ala Pro Ala Glu Cys Ser
225                 230
```

<210> SEQ ID NO 62
<211> LENGTH: 867
<212> TYPE: DNA
<213> ORGANISM: Canis familiaris
<220> FEATURE:
<221> NAME/KEY: CDS
<222> LOCATION: (1)..(705)
<223> OTHER INFORMATION:

<400> SEQUENCE: 62

```
atg gcc tgg acc ctt ctt ctc ctt gga ttc ctg gct cac tgc aca ggt    48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc    96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg    144
Leu Gly Gln Thr Ala Ser Ile Thr Cys Arg Gly Asn Ser Ile Gly Arg
```

```
                    35                  40                  45
aaa gat gtt cat tgg tac cag cag aag ccg ggc caa gcc ccc ctg ctg        192
Lys Asp Val His Trp Tyr Gln Gln Lys Pro Gly Gln Ala Pro Leu Leu
         50                  55                  60 att atc tat aat gat aac agc cag ccc tca ggg atc cct gag cga ttc        240
Ile Ile Tyr Asn Asp Asn Ser Gln Pro Ser Gly Ile Pro Glu Arg Phe
 65                  70                  75                  80 tct ggg acc aac tca ggg agc acg gcc acc ctg acc atc agt gag gcc        288
Ser Gly Thr Asn Ser Gly Ser Thr Ala Thr Leu Thr Ile Ser Glu Ala
                 85                  90                  95 caa acc aac gat gag gct gac tat tac tgc cag gtg tgg gaa agt agc        336
Gln Thr Asn Asp Glu Ala Asp Tyr Tyr Cys Gln Val Trp Glu Ser Ser
            100                 105                 110 agt aaa aat tgt tgg gta ttc ggt gaa ggg acc cag ctg acc gtc ctc        384
Ser Lys Asn Cys Trp Val Phe Gly Glu Gly Thr Gln Leu Thr Val Leu
        115                 120                 125 ggt cag ccc aag tcc tcc ccc ttg gtc aca ctc ttc ccg ccc tcc tct        432
Gly Gln Pro Lys Ser Ser Pro Leu Val Thr Leu Phe Pro Pro Ser Ser
    130                 135                 140 gag gag ctc ggc gcc aac aag gct acc ctg gtg tgc ctc atc agc gac        480
Glu Glu Leu Gly Ala Asn Lys Ala Thr Leu Val Cys Leu Ile Ser Asp
145                 150                 155                 160 ttc tac ccc agt ggc ctg aaa gtg gct tgg aag gca gat ggc agc acc        528
Phe Tyr Pro Ser Gly Leu Lys Val Ala Trp Lys Ala Asp Gly Ser Thr
                165                 170                 175 atc atc cag ggc gtg gaa acc acc aag ccc tcc aag cag agc aac aac        576
Ile Ile Gln Gly Val Glu Thr Thr Lys Pro Ser Lys Gln Ser Asn Asn
            180                 185                 190 aag tac acg gcc agc agc tac ctg agc ctg acg cct gac aag tgg aaa        624
Lys Tyr Thr Ala Ser Ser Tyr Leu Ser Leu Thr Pro Asp Lys Trp Lys
        195                 200                 205 tct cac agc agc ttc agc tgc ctg gtc acg cac cag ggg agc acc gtg        672
Ser His Ser Ser Phe Ser Cys Leu Val Thr His Gln Gly Ser Thr Val
    210                 215                 220 gag aag aag gtg gcc cct gca gag tgc tct tag gtccctgaga attcctgaga      725
Glu Lys Lys Val Ala Pro Ala Glu Cys Ser
225                 230 tggagccttc ctcacccaga caccccttcc ccagttcacc ttgtgcccct gaaaacccac      785
cctggaccag ctcagaccag gcaggtcact catcctccct gtttctactt gtgctcaata      845
aagactttat catttatcac tg                                               867

<210> SEQ ID NO 63
<211> LENGTH: 234
<212> TYPE: PRT
<213> ORGANISM: Canis familiaris

<400> SEQUENCE: 63

Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
                20                  25                  30

Leu Gly Gln Thr Ala Ser Ile Thr Cys Arg Gly Asn Ser Ile Gly Arg
            35                  40                  45

Lys Asp Val His Trp Tyr Gln Gln Lys Pro Gly Gln Ala Pro Leu Leu
        50                  55                  60

Ile Ile Tyr Asn Asp Asn Ser Gln Pro Ser Gly Ile Pro Glu Arg Phe
 65                 70                  75                  80
```

```
Ser Gly Thr Asn Ser Gly Ser Thr Ala Thr Leu Thr Ile Ser Glu Ala
             85                  90                  95

Gln Thr Asn Asp Glu Ala Asp Tyr Tyr Cys Gln Val Trp Glu Ser Ser
        100                 105                 110

Ser Lys Asn Cys Trp Val Phe Gly Glu Gly Thr Gln Leu Thr Val Leu
        115                 120                 125

Gly Gln Pro Lys Ser Ser Pro Leu Val Thr Leu Phe Pro Pro Ser Ser
    130                 135                 140

Glu Glu Leu Gly Ala Asn Lys Ala Thr Leu Val Cys Leu Ile Ser Asp
145                 150                 155                 160

Phe Tyr Pro Ser Gly Leu Lys Val Ala Trp Lys Ala Asp Gly Ser Thr
                165                 170                 175

Ile Ile Gln Gly Val Glu Thr Thr Lys Pro Ser Lys Gln Ser Asn Asn
            180                 185                 190

Lys Tyr Thr Ala Ser Ser Tyr Leu Ser Leu Thr Pro Asp Lys Trp Lys
        195                 200                 205

Ser His Ser Ser Phe Ser Cys Leu Val Thr His Gln Gly Ser Thr Val
    210                 215                 220

Glu Lys Lys Val Ala Pro Ala Glu Cys Ser
225                 230

<210> SEQ ID NO 64
<211> LENGTH: 861
<212> TYPE: DNA
<213> ORGANISM: Canis familiaris
<220> FEATURE:
<221> NAME/KEY: CDS
<222> LOCATION: (1)..(699)
<223> OTHER INFORMATION:

<400> SEQUENCE: 64 atg gcc tgg acc ctt ctt ctc ctt gga ttc ctg gct cac tgc aca ggt      48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc      96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg     144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg     192
Lys Asp Val His Trp Tyr Gln Gln Lys Pro Gly Gln Ala Pro Leu Leu
    50                  55                  60 att atc tat aat gat aac agc cag ccc tca ggg atc cct gag cga ttc     240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc     288
Ser Gly Thr Asn Ser Gly Ser Thr Ala Thr Leu Thr Ile Ser Glu Ala
                85                  90                  95 caa acc aac gat gag gct gac tat tac tgc cag gtg tgg gaa aat aaa     336
Gln Thr Asn Asp Glu Ala Asp Tyr Tyr Cys Gln Val Trp Glu Asn Lys
            100                 105                 110 tat tgt tgg gta ttc ggt gaa ggg acc cag ctg acc gtc ctc ggt cag     384
Tyr Cys Trp Val Phe Gly Glu Gly Thr Gln Leu Thr Val Leu Gly Gln
        115                 120                 125 ccc aag tcc tcc ccc ttg gtc aca ctc ttc ccg ccc tcc tct gag gag     432
Pro Lys Ser Ser Pro Leu Val Thr Leu Phe Pro Pro Ser Ser Glu Glu
    130                 135                 140 ctc ggc gcc aac aag gct acc ctg gtg tgc ctc atc agc gac ttc tac     480
```

```
Leu Gly Ala Asn Lys Ala Thr Leu Val Cys Leu Ile Ser Asp Phe Tyr
145                 150                 155                 160 ccc agt ggc ctg aaa gtg gct tgg aag gca gat ggc agc acc atc atc    528
Pro Ser Gly Leu Lys Val Ala Trp Lys Ala Asp Gly Ser Thr Ile Ile
                165                 170                 175 cag ggc gtg gaa acc acc aag ccc tcc aag cag agc aac aac aag tac    576
Gln Gly Val Glu Thr Thr Lys Pro Ser Lys Gln Ser Asn Asn Lys Tyr
        180                 185                 190 acg gcc agc agc tac ctg agc ctg acg cct gac aag tgg aaa tct cac    624
Thr Ala Ser Ser Tyr Leu Ser Leu Thr Pro Asp Lys Trp Lys Ser His
            195                 200                 205 agc agc ttc agc tgc ctg gtc acg cac cag ggg agc acc gtg gag aag    672
Ser Ser Phe Ser Cys Leu Val Thr His Gln Gly Ser Thr Val Glu Lys
        210                 215                 220 aag gtg gcc cct gca gag tgc tct tag gtccctgaga attcctgaga          719
Lys Val Ala Pro Ala Glu Cys Ser
225                 230 tggagccttc ctcacccaga caccccttcc ccagttcacc ttgtgcccct gaaaacccac  779
cctggaccag ctcagaccag gcaggtcact catcctccct gtttctactt gtgctcaata  839
aagactttat catttatcac tg                                          861

<210> SEQ ID NO 65
<211> LENGTH: 232
<212> TYPE: PRT
<213> ORGANISM: Canis familiaris

<400> SEQUENCE: 65

Met Ala Trp Thr Leu Leu Leu Gly Phe Leu Ala His Cys Thr Gly
1                5                   10                  15

Ser Val Ala Ser Tyr Val Leu Thr Gln Ser Pro Ser Val Ser Val Thr
                20                  25                  30

Leu Gly Gln Thr Ala Ser Ile Thr Cys Arg Gly Asn Ser Ile Gly Arg
            35                  40                  45

Lys Asp Val His Trp Tyr Gln Gln Lys Pro Gly Gln Ala Pro Leu Leu
        50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Trp Glu Asn Lys
            100                 105                 110

Tyr Cys Trp Val Phe Gly Glu Gly Thr Gln Leu Thr Val Leu Gly Gln
        115                 120                 125

Pro Lys Ser Ser Pro Leu Val Thr Leu Phe Pro Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
    210                 215                 220
```

Lys Val Ala Pro Ala Glu Cys Ser
225                 230

<210> SEQ ID NO 66
<211> LENGTH: 861
<212> TYPE: DNA
<213> ORGANISM: Canis familiaris
<220> FEATURE:
<221> NAME/KEY: CDS
<222> LOCATION: (1)..(699)
<223> OTHER INFORMATION:

<400> SEQUENCE: 66

```
atg gcc tgg acc ctt ctt ctc ctt gga ttc ctg gct cac tgc aca ggt      48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc      96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg     144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg     192
Lys Asp Val His Trp Tyr Gln Gln Lys Pro Gly Gln Ala Pro Leu Leu
    50                  55                  60 att atc tat aat gat aac agc cag ccc tca ggg atc cct gag cga ttc     240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc     288
Ser Gly Thr Asn Ser Gly Ser Thr Ala Thr Leu Thr Ile Ser Glu Ala
                85                  90                  95 caa acc aac gat gag gct gac tat tac tgc cag gtg tgg gaa atc tct     336
Gln Thr Asn Asp Glu Ala Asp Tyr Tyr Cys Gln Val Trp Glu Ile Ser
            100                 105                 110 gtg tgt tgg gta ttc ggt gaa ggg acc cag ctg acc gtc ctc ggt cag     384
Val Cys Trp Val Phe Gly Glu Gly Thr Gln Leu Thr Val Leu Gly Gln
        115                 120                 125 ccc aag tcc tcc ccc ttg gtc aca ctc ttc ccg ccc tcc tct gag gag     432
Pro Lys Ser Ser Pro Leu Val Thr Leu Phe Pro Pro Ser Ser Glu Glu
    130                 135                 140 ctc ggc gcc aac aag gct acc ctg gtg tgc ctc atc agc gac ttc tac     480
Leu Gly Ala Asn Lys Ala Thr Leu Val Cys Leu Ile Ser Asp Phe Tyr
145                 150                 155                 160 ccc agt ggc ctg aaa gtg gct tgg aag gca gat ggc agc acc atc atc     528
Pro Ser Gly Leu Lys Val Ala Trp Lys Ala Asp Gly Ser Thr Ile Ile
                165                 170                 175 cag ggc gtg gaa acc acc aag ccc tcc aag cag agc aac aac aag tac     576
Gln Gly Val Glu Thr Thr Lys Pro Ser Lys Gln Ser Asn Asn Lys Tyr
            180                 185                 190 acg gcc agc agc tac ctg agc ctg acg cct gac aag tgg aaa tct cac     624
Thr Ala Ser Ser Tyr Leu Ser Leu Thr Pro Asp Lys Trp Lys Ser His
        195                 200                 205 agc agc ttc agc tgc ctg gtc acg cac cag ggg agc acc gtg gag aag     672
Ser Ser Phe Ser Cys Leu Val Thr His Gln Gly Ser Thr Val Glu Lys
    210                 215                 220 aag gtg gcc cct gca gag tgc tct tag gtccctgaga attcctgaga            719
Lys Val Ala Pro Ala Glu Cys Ser
225                 230 tggagccttc ctcacccaga caccccttcc ccagttcacc ttgtgccct gaaaacccac    779 cctggaccag ctcagaccag gcaggtcact catcctccct gtttctactt gtgctcaata  839
```

```
aagactttat catttatcac tg                                           861
```

```
<210> SEQ ID NO 67
<211> LENGTH: 232
<212> TYPE: PRT
<213> ORGANISM: Canis familiaris

<400> SEQUENCE: 67

Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
                20                  25                  30

Leu Gly Gln Thr Ala Ser Ile Thr Cys Arg Gly Asn Ser Ile Gly Arg
            35                  40                  45

Lys Asp Val His Trp Tyr Gln Gln Lys Pro Gly Gln Ala Pro Leu Leu
        50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Trp Glu Ile Ser
            100                 105                 110

Val Cys Trp Val Phe Gly Glu Gly Thr Gln Leu Thr Val Leu Gly Gln
        115                 120                 125

Pro Lys Ser Ser Pro Leu Val Thr Leu Phe Pro Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
    210                 215                 220

Lys Val Ala Pro Ala Glu Cys Ser
225                 230
```

```
<210> SEQ ID NO 68
<211> LENGTH: 867
<212> TYPE: DNA
<213> ORGANISM: Canis familiaris
<220> FEATURE:
<221> NAME/KEY: CDS
<222> LOCATION: (1)..(705)
<223> OTHER INFORMATION:

<400> SEQUENCE: 68 atg gcc tgg acc ctt ctt ctc ctt gga ttc ctg gct cac tgc aca ggt     48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc     96
Ser Val Ala Ser Tyr Val Leu Thr Gln Ser Pro Ser Val Ser Val Thr
                20                  25                  30 ctg gga cag acg gcc agc atc acc tgt agg gga aac agc att gga agg    144
Leu Gly Gln Thr Ala Ser Ile Thr Cys Arg Gly Asn Ser Ile Gly Arg
            35                  40                  45
```

```
aaa gat gtt cat tgg tac cag cag aag ccg ggc caa gcc ccc ctg ctg      192
Lys Asp Val His Trp Tyr Gln Gln Lys Pro Gly Gln Ala Pro Leu Leu
 50                  55                  60 att atc tat aat gat aac agc cag ccc tca ggg atc cct gag cga ttc      240
Ile Ile Tyr Asn Asp Asn Ser Gln Pro Ser Gly Ile Pro Glu Arg Phe
 65                  70                  75                  80 tct ggg acc aac tca ggg agc acg gcc acc ctg acc atc agt gag gcc      288
Ser Gly Thr Asn Ser Gly Ser Thr Ala Thr Leu Thr Ile Ser Glu Ala
                 85                  90                  95 caa acc aac gat gag gct gac tat tac tgc cag gag atg cac aca cct      336
Gln Thr Asn Asp Glu Ala Asp Tyr Tyr Cys Gln Glu Met His Thr Pro
            100                 105                 110 gaa tca cag tgt tgg gta ttc ggt gaa ggg acc cag ctg acc gtc ctc      384
Glu Ser Gln Cys Trp Val Phe Gly Glu Gly Thr Gln Leu Thr Val Leu
        115                 120                 125 ggt cag ccc aag tcc tcc ccc ttg gtc aca ctc ttc ccg ccc tcc tct      432
Gly Gln Pro Lys Ser Ser Pro Leu Val Thr Leu Phe Pro Pro Ser Ser
130                 135                 140 gag gag ctc ggc gcc aac aag gct acc ctg gtg tgc ctc atc agc gac      480
Glu Glu Leu Gly Ala Asn Lys Ala Thr Leu Val Cys Leu Ile Ser Asp
145                 150                 155                 160 ttc tac ccc agt ggc ctg aaa gtg gct tgg aag gca gat ggc agc acc      528
Phe Tyr Pro Ser Gly Leu Lys Val Ala Trp Lys Ala Asp Gly Ser Thr
                165                 170                 175 atc atc cag ggc gtg gaa acc acc aag ccc tcc aag cag agc aac aac      576
Ile Ile Gln Gly Val Glu Thr Thr Lys Pro Ser Lys Gln Ser Asn Asn
            180                 185                 190 aag tac acg gcc agc agc tac ctg agc ctg acg cct gac aag tgg aaa      624
Lys Tyr Thr Ala Ser Ser Tyr Leu Ser Leu Thr Pro Asp Lys Trp Lys
        195                 200                 205 tct cac agc agc ttc agc tgc ctg gtc acg cac cag ggg agc acc gtg      672
Ser His Ser Ser Phe Ser Cys Leu Val Thr His Gln Gly Ser Thr Val
    210                 215                 220 gag aag aag gtg gcc cct gca gag tgc tct tag gtccctgaga attcctgaga    725
Glu Lys Lys Val Ala Pro Ala Glu Cys Ser
225                 230 tggagccttc ctcacccaga caccccttcc ccagttcacc ttgtgcccct gaaaacccac    785
cctggaccag ctcagaccag gcaggtcact catcctccct gtttctactt gtgctcaata   845
aagactttat catttatcac tg                                             867

<210> SEQ ID NO 69
<211> LENGTH: 234
<212> TYPE: PRT
<213> ORGANISM: Canis familiaris

<400> SEQUENCE: 69

Met Ala Trp Thr Leu Leu Leu Gly Phe Leu Ala His Cys Thr Gly
 1               5                  10                  15

Ser Val Ala Ser Tyr Val Leu Thr Gln Ser Pro Ser Val Ser Val Thr
                 20                  25                  30

Leu Gly Gln Thr Ala Ser Ile Thr Cys Arg Gly Asn Ser Ile Gly Arg
             35                  40                  45

Lys Asp Val His Trp Tyr Gln Gln Lys Pro Gly Gln Ala Pro Leu Leu
 50                  55                  60

Ile Ile Tyr Asn Asp Asn Ser Gln Pro Ser Gly Ile Pro Glu Arg Phe
 65                  70                  75                  80

Ser Gly Thr Asn Ser Gly Ser Thr Ala Thr Leu Thr Ile Ser Glu Ala
                 85                  90                  95
```

```
Gln Thr Asn Asp Glu Ala Asp Tyr Tyr Cys Gln Glu Met His Thr Pro
            100                 105                 110

Glu Ser Gln Cys Trp Val Phe Gly Glu Gly Thr Gln Leu Thr Val Leu
        115                 120                 125

Gly Gln Pro Lys Ser Ser Pro Leu Val Thr Leu Phe Pro Pro Ser Ser
    130                 135                 140

Glu Glu Leu Gly Ala Asn Lys Ala Thr Leu Val Cys Leu Ile Ser Asp
145                 150                 155                 160

Phe Tyr Pro Ser Gly Leu Lys Val Ala Trp Lys Ala Asp Gly Ser Thr
                165                 170                 175

Ile Ile Gln Gly Val Glu Thr Thr Lys Pro Ser Lys Gln Ser Asn Asn
            180                 185                 190

Lys Tyr Thr Ala Ser Ser Tyr Leu Ser Leu Thr Pro Asp Lys Trp Lys
        195                 200                 205

Ser His Ser Ser Phe Ser Cys Leu Val Thr His Gln Gly Ser Thr Val
    210                 215                 220

Glu Lys Lys Val Ala Pro Ala Glu Cys Ser
225                 230

<210> SEQ ID NO 70
<211> LENGTH: 861
<212> TYPE: DNA
<213> ORGANISM: Canis familiaris
<220> FEATURE:
<221> NAME/KEY: CDS
<222> LOCATION: (1)..(699)
<223> OTHER INFORMATION:

<400> SEQUENCE: 70 atg gcc tgg acc ctt ctt ctc ctt gga ttc ctg gct cac tgc aca ggt        48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc        96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg       144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg       192
Lys Asp Val His Trp Tyr Gln Gln Lys Pro Gly Gln Ala Pro Leu Leu
    50                  55                  60 att atc tat aat gat aac agc cag ccc tca ggg atc cct gag cga ttc       240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc       288
Ser Gly Thr Asn Ser Gly Ser Thr Ala Thr Leu Thr Ile Ser Glu Ala
                85                  90                  95 caa acc aac gat gag gct gac tat tac tgc cag cat tac cac cat gac       336
Gln Thr Asn Asp Glu Ala Asp Tyr Tyr Cys Gln His Tyr His His Asp
            100                 105                 110 tat tgt tgg gta ttc ggt gaa ggg acc cag ctg acc gtc ctc ggt cag       384
Tyr Cys Trp Val Phe Gly Glu Gly Thr Gln Leu Thr Val Leu Gly Gln
        115                 120                 125 ccc aag tcc tcc ccc ttg gtc aca ctc ttc ccg ccc tcc tct gag gag       432
Pro Lys Ser Ser Pro Leu Val Thr Leu Phe Pro Pro Ser Ser Glu Glu
    130                 135                 140 ctc ggc gcc aac aag gct acc ctg gtg tgc ctc atc agc gac ttc tac       480
Leu Gly Ala Asn Lys Ala Thr Leu Val Cys Leu Ile Ser Asp Phe Tyr
145                 150                 155                 160
```

```
ccc agt ggc ctg aaa gtg gct tgg aag gca gat ggc agc acc atc atc      528
Pro Ser Gly Leu Lys Val Ala Trp Lys Ala Asp Gly Ser Thr Ile Ile
            165                 170                 175 cag ggc gtg gaa acc acc aag ccc tcc aag cag agc aac aac aag tac      576
Gln Gly Val Glu Thr Thr Lys Pro Ser Lys Gln Ser Asn Asn Lys Tyr
        180                 185                 190 acg gcc agc agc tac ctg agc ctg acg cct gac aag tgg aaa tct cac      624
Thr Ala Ser Ser Tyr Leu Ser Leu Thr Pro Asp Lys Trp Lys Ser His
            195                 200                 205 agc agc ttc agc tgc ctg gtc acg cac cag ggg agc acc gtg gag aag      672
Ser Ser Phe Ser Cys Leu Val Thr His Gln Gly Ser Thr Val Glu Lys
    210                 215                 220 aag gtg gcc cct gca gag tgc tct tag gtccctgaga attcctgaga            719
Lys Val Ala Pro Ala Glu Cys Ser
225                 230 tggagccttc ctcacccaga caccccttcc ccagttcacc ttgtgcccct gaaaacccac    779
cctggaccag ctcagaccag gcaggtcact catcctccct gtttctactt gtgctcaata    839
aagactttat catttatcac tg                                             861

<210> SEQ ID NO 71
<211> LENGTH: 232
<212> TYPE: PRT
<213> ORGANISM: Canis familiaris

<400> SEQUENCE: 71

Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln His Tyr His His Asp
            100                 105                 110

Tyr Cys Trp Val Phe Gly Glu Gly Thr Gln Leu Thr Val Leu Gly Gln
        115                 120                 125

Pro Lys Ser Ser Pro Leu Val Thr Leu Phe Pro Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
    210                 215                 220

Lys Val Ala Pro Ala Glu Cys Ser
225                 230
```

<210> SEQ ID NO 72
<211> LENGTH: 861
<212> TYPE: DNA
<213> ORGANISM: Canis familiaris
<220> FEATURE:
<221> NAME/KEY: CDS
<222> LOCATION: (1)..(699)
<223> OTHER INFORMATION:

<400> SEQUENCE: 72

```
atg gcc tgg acc ctt ctt ctc ctt gga ttc ctg gct cac tgc aca ggt      48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc      96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg     144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg     192
Lys Asp Val His Trp Tyr Gln Gln Lys Pro Gly Gln Ala Pro Leu Leu
    50                  55                  60 att atc tat aat gat aac agc cag ccc tca ggg atc cct gag cga ttc     240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc     288
Ser Gly Thr Asn Ser Gly Ser Thr Ala Thr Leu Thr Ile Ser Glu Ala
                85                  90                  95 caa acc aac gat gag gct gac tat tac tgc cag gtc cat ggg ggg gga     336
Gln Thr Asn Asp Glu Ala Asp Tyr Tyr Cys Gln Val His Gly Gly Gly
            100                 105                 110 ggg tgt tgg gta ttc ggt gaa ggg acc cag ctg acc gtc ctc ggt cag     384
Gly Cys Trp Val Phe Gly Glu Gly Thr Gln Leu Thr Val Leu Gly Gln
        115                 120                 125 ccc aag tcc tcc ccc ttg gtc aca ctc ttc ccg ccc tcc tct gag gag     432
Pro Lys Ser Ser Pro Leu Val Thr Leu Phe Pro Pro Ser Ser Glu Glu
    130                 135                 140 ctc ggc gcc aac aag gct acc ctg gtg tgc ctc atc agc gac ttc tac     480
Leu Gly Ala Asn Lys Ala Thr Leu Val Cys Leu Ile Ser Asp Phe Tyr
145                 150                 155                 160 ccc agt ggc ctg aaa gtg gct tgg aag gca gat ggc agc acc atc atc     528
Pro Ser Gly Leu Lys Val Ala Trp Lys Ala Asp Gly Ser Thr Ile Ile
                165                 170                 175 cag ggc gtg gaa acc acc aag ccc tcc aag cag agc aac aac aag tac     576
Gln Gly Val Glu Thr Thr Lys Pro Ser Lys Gln Ser Asn Asn Lys Tyr
            180                 185                 190 acg gcc agc agc tac ctg agc ctg acg cct gac aag tgg aaa tct cac     624
Thr Ala Ser Ser Tyr Leu Ser Leu Thr Pro Asp Lys Trp Lys Ser His
        195                 200                 205 agc agc ttc agc tgc ctg gtc acg cac cag ggg agc acc gtg gag aag     672
Ser Ser Phe Ser Cys Leu Val Thr His Gln Gly Ser Thr Val Glu Lys
    210                 215                 220 aag gtg gcc cct gca gag tgc tct tag gtccctgaga attcctgaga            719
Lys Val Ala Pro Ala Glu Cys Ser
225                 230 tggagccttc ctcacccaga cacccettcc ccagttcacc ttgtgcccct gaaaacccac    779
cctggaccag ctcagaccag gcaggtcact catcctccct gtttctactt gtgctcaata    839
aagactttat catttatcac tg                                             861
```

<210> SEQ ID NO 73
<211> LENGTH: 232
<212> TYPE: PRT
<213> ORGANISM: Canis familiaris

<400> SEQUENCE: 73

Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val His Gly Gly Gly
            100                 105                 110

Gly Cys Trp Val Phe Gly Glu Gly Thr Gln Leu Thr Val Leu Gly Gln
        115                 120                 125

Pro Lys Ser Ser Pro Leu Val Thr Leu Phe Pro Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
    210                 215                 220

Lys Val Ala Pro Ala Glu Cys Ser
225                 230

<210> SEQ ID NO 74
<211> LENGTH: 861
<212> TYPE: DNA
<213> ORGANISM: Canis familiaris
<220> FEATURE:
<221> NAME/KEY: CDS
<222> LOCATION: (1)..(699)
<223> OTHER INFORMATION:

<400> SEQUENCE: 74 atg gcc tgg acc ctt ctt ctc ctt gga ttc ctg gct cac tgc aca ggt    48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc    96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg   144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg   192
Lys Asp Val His Trp Tyr Gln Gln Lys Pro Gly Gln Ala Pro Leu Leu

```
                  50                  55                  60
att atc tat aat gat aac agc cag ccc tca ggg atc cct gag cga ttc        240
Ile Ile Tyr Asn Asp Asn Ser Gln Pro Ser Gly Ile Pro Glu Arg Phe
 65                  70                  75                  80 tct ggg acc aac tca ggg agc acg gcc acc ctg acc atc agt gag gcc        288
Ser Gly Thr Asn Ser Gly Ser Thr Ala Thr Leu Thr Ile Ser Glu Ala
                 85                  90                  95 caa acc aac gat gag gct gac tat tac tgc cag aaa cat cgg ggt gca        336
Gln Thr Asn Asp Glu Ala Asp Tyr Tyr Cys Gln Lys His Arg Gly Ala
            100                 105                 110 ggt tgt tgg gta ttc ggt gaa ggg acc cag ctg acc gtc ctc ggt cag        384
Gly Cys Trp Val Phe Gly Glu Gly Thr Gln Leu Thr Val Leu Gly Gln
        115                 120                 125 ccc aag tcc tcc ccc ttg gtc aca ctc ttc ccg ccc tcc tct gag gag        432
Pro Lys Ser Ser Pro Leu Val Thr Leu Phe Pro Pro Ser Ser Glu Glu
    130                 135                 140 ctc ggc gcc aac aag gct acc ctg gtg tgc ctc atc agc gac ttc tac        480
Leu Gly Ala Asn Lys Ala Thr Leu Val Cys Leu Ile Ser Asp Phe Tyr
145                 150                 155                 160 ccc agt ggc ctg aaa gtg gct tgg aag gca gat ggc agc acc atc atc        528
Pro Ser Gly Leu Lys Val Ala Trp Lys Ala Asp Gly Ser Thr Ile Ile
                165                 170                 175 cag ggc gtg gaa acc acc aag ccc tcc aag cag agc aac aac aag tac        576
Gln Gly Val Glu Thr Thr Lys Pro Ser Lys Gln Ser Asn Asn Lys Tyr
            180                 185                 190 acg gcc agc agc tac ctg agc ctg acg cct gac aag tgg aaa tct cac        624
Thr Ala Ser Ser Tyr Leu Ser Leu Thr Pro Asp Lys Trp Lys Ser His
        195                 200                 205 agc agc ttc agc tgc ctg gtc acg cac cag ggg agc acc gtg gag aag        672
Ser Ser Phe Ser Cys Leu Val Thr His Gln Gly Ser Thr Val Glu Lys
    210                 215                 220 aag gtg gcc cct gca gag tgc tct tag gtccctgaga attcctgaga             719
Lys Val Ala Pro Ala Glu Cys Ser
225                 230 tggagccttc ctcacccaga cacccottcc ccagttcacc ttgtgcccct gaaaacccac      779
cctggaccag ctcagaccag gcaggtcact catcctccct gtttctactt gtgctcaata      839
aagactttat catttatcac tg                                               861

<210> SEQ ID NO 75
<211> LENGTH: 232
<212> TYPE: PRT
<213> ORGANISM: Canis familiaris

<400> SEQUENCE: 75

Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
                20                  25                  30

Leu Gly Gln Thr Ala Ser Ile Thr Cys Arg Gly Asn Ser Ile Gly Arg
            35                  40                  45

Lys Asp Val His Trp Tyr Gln Gln Lys Pro Gly Gln Ala Pro Leu Leu
        50                  55                  60

Ile Ile Tyr Asn Asp Asn Ser Gln Pro Ser Gly Ile Pro Glu Arg Phe
 65                  70                  75                  80

Ser Gly Thr Asn Ser Gly Ser Thr Ala Thr Leu Thr Ile Ser Glu Ala
                 85                  90                  95

Gln Thr Asn Asp Glu Ala Asp Tyr Tyr Cys Gln Lys His Arg Gly Ala
```

```
                100                 105                 110
Gly Cys Trp Val Phe Gly Glu Gly Thr Gln Leu Thr Val Leu Gly Gln
            115                 120                 125

Pro Lys Ser Ser Pro Leu Val Thr Leu Phe Pro Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
    210                 215                 220

Lys Val Ala Pro Ala Glu Cys Ser
225                 230

<210> SEQ ID NO 76
<211> LENGTH: 858
<212> TYPE: DNA
<213> ORGANISM: Canis familiaris
<220> FEATURE:
<221> NAME/KEY: CDS
<222> LOCATION: (1)..(696)
<223> OTHER INFORMATION:

<400> SEQUENCE: 76 atg gcc tgg acc ctt ctt ctc ctt gga ttc ctg gct cac tgc aca ggt        48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc        96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg       144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg       192
Lys Asp Val His Trp Tyr Gln Gln Lys Pro Gly Gln Ala Pro Leu Leu
    50                  55                  60 att atc tat aat gat aac agc cag ccc tca ggg atc cct gag cga ttc       240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc       288
Ser Gly Thr Asn Ser Gly Ser Thr Ala Thr Leu Thr Ile Ser Glu Ala
                85                  90                  95 caa acc aac gat gag gct gac tat tac tgc cag gtg tcc ctt ggg tct       336
Gln Thr Asn Asp Glu Ala Asp Tyr Tyr Cys Gln Val Ser Leu Gly Ser
            100                 105                 110 tgt tgg gta ttc ggt gaa ggg acc cag ctg acc gtc ctc ggt cag ccc       384
Cys Trp Val Phe Gly Glu Gly Thr Gln Leu Thr Val Leu Gly Gln Pro
        115                 120                 125 aag tcc tcc ccc ttg gtc aca ctc ttc ccg ccc tct gag gag ctc           432
Lys Ser Ser Pro Leu Val Thr Leu Phe Pro Pro Ser Ser Glu Glu Leu
    130                 135                 140 ggc gcc aac aag gct acc ctg gtg tgc ctc atc agc gac ttc tac ccc       480
Gly Ala Asn Lys Ala Thr Leu Val Cys Leu Ile Ser Asp Phe Tyr Pro
145                 150                 155                 160 agt ggc ctg aaa gtg gct tgg aag gca gat ggc agc acc atc atc cag       528
```

-continued

```
Ser Gly Leu Lys Val Ala Trp Lys Ala Asp Gly Ser Thr Ile Ile Gln
            165                 170                 175 ggc gtg gaa acc acc aag ccc tcc aag cag agc aac aac aag tac acg       576
Gly Val Glu Thr Thr Lys Pro Ser Lys Gln Ser Asn Asn Lys Tyr Thr
        180                 185                 190 gcc agc agc tac ctg agc ctg acg cct gac aag tgg aaa tct cac agc       624
Ala Ser Ser Tyr Leu Ser Leu Thr Pro Asp Lys Trp Lys Ser His Ser
        195                 200                 205 agc ttc agc tgc ctg gtc acg cac cag ggg agc acc gtg gag aag aag       672
Ser Phe Ser Cys Leu Val Thr His Gln Gly Ser Thr Val Glu Lys Lys
        210                 215                 220 gtg gcc cct gca gag tgc tct tag gtccctgaga attcctgaga tggagccttc      726
Val Ala Pro Ala Glu Cys Ser
225                 230 ctcacccaga cacccttcc ccagttcacc ttgtgcccct gaaaacccac cctggaccag       786
ctcagaccag gcaggtcact catcctccct gtttctactt gtgctcaata aagactttat     846
catttatcac tg                                                          858
```

<210> SEQ ID NO 77
<211> LENGTH: 231
<212> TYPE: PRT
<213> ORGANISM: Canis familiaris

<400> SEQUENCE: 77

```
Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Ser Leu Gly Ser
            100                 105                 110

Cys Trp Val Phe Gly Glu Gly Thr Gln Leu Thr Val Leu Gly Gln Pro
        115                 120                 125

Lys Ser Ser Pro Leu Val Thr Leu Phe Pro Pro Ser Ser Glu Glu Leu
    130                 135                 140

Gly Ala Asn Lys Ala Thr Leu Val Cys Leu Ile Ser Asp Phe Tyr Pro
145                 150                 155                 160

Ser Gly Leu Lys Val Ala Trp Lys Ala Asp Gly Ser Thr Ile Ile Gln
                165                 170                 175

Gly Val Glu Thr Thr Lys Pro Ser Lys Gln Ser Asn Asn Lys Tyr Thr
            180                 185                 190

Ala Ser Ser Tyr Leu Ser Leu Thr Pro Asp Lys Trp Lys Ser His Ser
        195                 200                 205

Ser Phe Ser Cys Leu Val Thr His Gln Gly Ser Thr Val Glu Lys Lys
    210                 215                 220

Val Ala Pro Ala Glu Cys Ser
225                 230
```

<210> SEQ ID NO 78
<211> LENGTH: 858
<212> TYPE: DNA
<213> ORGANISM: Canis familiaris
<220> FEATURE:
<221> NAME/KEY: CDS
<222> LOCATION: (1)..(696)
<223> OTHER INFORMATION:

<400> SEQUENCE: 78

```
atg gcc tgg acc ctt ctt ctc ctt gga ttc ctg gct cac tgc aca ggt      48
Met Ala Trp Thr Leu Leu Leu Leu Gly Phe Leu Ala His Cys Thr Gly
 1               5                  10                  15 tcc gtg gcc tcc tat gtg ctg act cag tca ccc tca gtg tca gtg acc      96
Ser Val Ala Ser Tyr Val Leu Thr Gln Ser Pro Ser Val Ser Val Thr
                20                  25                  30 ctg gga cag acg gcc agc atc acc tgt agg gga aac agc att gga agg     144
Leu Gly Gln Thr Ala Ser Ile Thr Cys Arg Gly Asn Ser Ile Gly Arg
            35                  40                  45 aaa gat gtt cat tgg tac cag cag aag ccg ggc caa gcc ccc ctg ctg     192
Lys Asp Val His Trp Tyr Gln Gln Lys Pro Gly Gln Ala Pro Leu Leu
        50                  55                  60 att atc tat aat gat aac agc cag ccc tca ggg atc cct gag cga ttc     240
Ile Ile Tyr Asn Asp Asn Ser Gln Pro Ser Gly Ile Pro Glu Arg Phe
 65                  70                  75                  80 tct ggg acc aac tca ggg agc acg gcc acc ctg acc atc agt gag gcc     288
Ser Gly Thr Asn Ser Gly Ser Thr Ala Thr Leu Thr Ile Ser Glu Ala
                 85                  90                  95 caa acc aac gat gag gct gac tat tac tgc cag gta ttg atg gga ggg     336
Gln Thr Asn Asp Glu Ala Asp Tyr Tyr Cys Gln Val Leu Met Gly Gly
               100                 105                 110 tgt tgg gta ttc ggt gaa ggg acc cag ctg acc gtc ctc ggt cag ccc     384
Cys Trp Val Phe Gly Glu Gly Thr Gln Leu Thr Val Leu Gly Gln Pro
            115                 120                 125 aag tcc tcc ccc ttg gtc aca ctc ttc ccg ccc tcc tct gag gag ctc     432
Lys Ser Ser Pro Leu Val Thr Leu Phe Pro Pro Ser Ser Glu Glu Leu
        130                 135                 140 ggc gcc aac aag gct acc ctg gtg tgc ctc atc agc gac ttc tac ccc     480
Gly Ala Asn Lys Ala Thr Leu Val Cys Leu Ile Ser Asp Phe Tyr Pro
145                 150                 155                 160 agt ggc ctg aaa gtg gct tgg aag gca gat ggc agc acc atc atc cag     528
Ser Gly Leu Lys Val Ala Trp Lys Ala Asp Gly Ser Thr Ile Ile Gln
                165                 170                 175 ggc gtg gaa acc acc aag ccc tcc aag cag agc aac aac aag tac acg     576
Gly Val Glu Thr Thr Lys Pro Ser Lys Gln Ser Asn Asn Lys Tyr Thr
            180                 185                 190 gcc agc agc tac ctg agc ctg acg cct gac aag tgg aaa tct cac agc     624
Ala Ser Ser Tyr Leu Ser Leu Thr Pro Asp Lys Trp Lys Ser His Ser
        195                 200                 205 agc ttc agc tgc ctg gtc acg cac cag ggg agc acc gtg gag aag aag     672
Ser Phe Ser Cys Leu Val Thr His Gln Gly Ser Thr Val Glu Lys Lys
    210                 215                 220 gtg gcc cct gca gag tgc tct tag gtccctgaga attcctgaga tggagccttc    726
Val Ala Pro Ala Glu Cys Ser
225                 230 ctcacccaga cacccttcc ccagttcacc ttgtgcccct gaaaacccac cctggaccag    786
ctcagaccag gcaggtcact catcctccct gtttctactt gtgctcaata aagactttat    846
catttatcac tg                                                        858
```

<210> SEQ ID NO 79

<211> LENGTH: 231
<212> TYPE: PRT
<213> ORGANISM: Canis familiaris

<400> SEQUENCE: 79

```
Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
                20                  25                  30

Leu Gly Gln Thr Ala Ser Ile Thr Cys Arg Gly Asn Ser Ile Gly Arg
            35                  40                  45

Lys Asp Val His Trp Tyr Gln Gln Lys Pro Gly Gln Ala Pro Leu Leu
50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Leu Met Gly Gly
            100                 105                 110

Cys Trp Val Phe Gly Glu Gly Thr Gln Leu Thr Val Leu Gly Gln Pro
        115                 120                 125

Lys Ser Ser Pro Leu Val Thr Leu Phe Pro Pro Ser Ser Glu Glu Leu
130                 135                 140

Gly Ala Asn Lys Ala Thr Leu Val Cys Leu Ile Ser Asp Phe Tyr Pro
145                 150                 155                 160

Ser Gly Leu Lys Val Ala Trp Lys Ala Asp Gly Ser Thr Ile Ile Gln
                165                 170                 175

Gly Val Glu Thr Thr Lys Pro Ser Lys Gln Ser Asn Asn Lys Tyr Thr
            180                 185                 190

Ala Ser Ser Tyr Leu Ser Leu Thr Pro Asp Lys Trp Lys Ser His Ser
        195                 200                 205

Ser Phe Ser Cys Leu Val Thr His Gln Gly Ser Thr Val Glu Lys Lys
    210                 215                 220

Val Ala Pro Ala Glu Cys Ser
225                 230
```

<210> SEQ ID NO 80
<211> LENGTH: 834
<212> TYPE: DNA
<213> ORGANISM: Canis familiaris
<220> FEATURE:
<221> NAME/KEY: CDS
<222> LOCATION: (1)..(672)
<223> OTHER INFORMATION:

<400> SEQUENCE: 80

```
atg tcc tct ctt gca ggt tcc atg gct gcc aac aag ctg act caa tcc      48
Met Ser Ser Leu Ala Gly Ser Met Ala Ala Asn Lys Leu Thr Gln Ser
1               5                   10                  15 ctg ttt atg tca gtg gcc ctg gga cag atg gcc agg atc acc tgt ggg      96
Leu Phe Met Ser Val Ala Leu Gly Gln Met Ala Arg Ile Thr Cys Gly
                20                  25                  30 aga gac aac tct gga aga aaa agt gct cac tgg tac cag cag aag cca     144
Arg Asp Asn Ser Gly Arg Lys Ser Ala His Trp Tyr Gln Gln Lys Pro
            35                  40                  45 agc cag gct ccc gtg atg ctt atc gat gat gat tgc ttc cag ccc tca     192
Ser Gln Ala Pro Val Met Leu Ile Asp Asp Asp Cys Phe Gln Pro Ser
        50                  55                  60
```

```
gga ttc tct gag caa ttc tca ggc act aac tcg ggg aac aca gcc acc      240
Gly Phe Ser Glu Gln Phe Ser Gly Thr Asn Ser Gly Asn Thr Ala Thr
 65                  70                  75                  80 ctg acc att agt ggg ccc cca gcg agg acg cag gtc agg tat gcc cag      288
Leu Thr Ile Ser Gly Pro Pro Ala Arg Thr Gln Val Arg Tyr Ala Gln
                 85                  90                  95 ccc ggg gct cca ggg gca ggg act tgt tgg gta ttc ggt gaa ggg acc      336
Pro Gly Ala Pro Gly Ala Gly Thr Cys Trp Val Phe Gly Glu Gly Thr
            100                 105                 110 cag ctg acc gtc ctc ggt cag ccc aag tcc tcc ccc ttg gtc aca ctc      384
Gln Leu Thr Val Leu Gly Gln Pro Lys Ser Ser Pro Leu Val Thr Leu
        115                 120                 125 ttc ccg ccc tcc tct gag gag ctc ggc gcc aac aag gct acc ctg gtg      432
Phe Pro Pro Ser Ser Glu Glu Leu Gly Ala Asn Lys Ala Thr Leu Val
    130                 135                 140 tgc ctc atc agc gac ttc tac ccc agt ggc ctg aaa gtg gct tgg aag      480
Cys Leu Ile Ser Asp Phe Tyr Pro Ser Gly Leu Lys Val Ala Trp Lys
145                 150                 155                 160 gca gat ggc agc acc atc atc cag ggc gtg gaa acc acc aag ccc tcc      528
Ala Asp Gly Ser Thr Ile Ile Gln Gly Val Glu Thr Thr Lys Pro Ser
                165                 170                 175 aag cag agc aac aac aag tac acg gcc agc agc tac ctg agc ctg acg      576
Lys Gln Ser Asn Asn Lys Tyr Thr Ala Ser Ser Tyr Leu Ser Leu Thr
            180                 185                 190 cct gac aag tgg aaa tct cac agc agc ttc agc tgc ctg gtc acg cac      624
Pro Asp Lys Trp Lys Ser His Ser Ser Phe Ser Cys Leu Val Thr His
        195                 200                 205 cag ggg agc acc gtg gag aag aag gtg gcc cct gca gag tgc tct tag      672
Gln Gly Ser Thr Val Glu Lys Lys Val Ala Pro Ala Glu Cys Ser
    210                 215                 220 gtccctgaga attcctgaga tggagccttc ctcacccaga caccccttcc ccagttcacc    732
ttgtgcccct gaaaacccac cctggaccag ctcagaccag gcaggtcact catcctccct    792
gtttctactt gtgctcaata aagactttat catttatcac tg                       834

<210> SEQ ID NO 81
<211> LENGTH: 223
<212> TYPE: PRT
<213> ORGANISM: Canis familiaris

<400> SEQUENCE: 81

Met Ser Ser Leu Ala Gly Ser Met Ala Ala Asn Lys Leu Thr Gln Ser
 1               5                  10                  15

Leu Phe Met Ser Val Ala Leu Gly Gln Met Ala Arg Ile Thr Cys Gly
                20                  25                  30

Arg Asp Asn Ser Gly Arg Lys Ser Ala His Trp Tyr Gln Gln Lys Pro
            35                  40                  45

Ser Gln Ala Pro Val Met Leu Ile Asp Asp Cys Phe Gln Pro Ser
    50                  55                  60

Gly Phe Ser Glu Gln Phe Ser Gly Thr Asn Ser Gly Asn Thr Ala Thr
 65                  70                  75                  80

Leu Thr Ile Ser Gly Pro Pro Ala Arg Thr Gln Val Arg Tyr Ala Gln
                 85                  90                  95

Pro Gly Ala Pro Gly Ala Gly Thr Cys Trp Val Phe Gly Glu Gly Thr
            100                 105                 110

Gln Leu Thr Val Leu Gly Gln Pro Lys Ser Ser Pro Leu Val Thr Leu
        115                 120                 125

Phe Pro Pro Ser Ser Glu Glu Leu Gly Ala Asn Lys Ala Thr Leu Val
```

```
                     130                 135                 140
Cys Leu Ile Ser Asp Phe Tyr Pro Ser Gly Leu Lys Val Ala Trp Lys
145                 150                 155                 160

Ala Asp Gly Ser Thr Ile Ile Gln Gly Val Glu Thr Thr Lys Pro Ser
                165                 170                 175

Lys Gln Ser Asn Asn Lys Tyr Thr Ala Ser Ser Tyr Leu Ser Leu Thr
            180                 185                 190

Pro Asp Lys Trp Lys Ser His Ser Ser Phe Ser Cys Leu Val Thr His
        195                 200                 205

Gln Gly Ser Thr Val Glu Lys Lys Val Ala Pro Ala Glu Cys Ser
    210                 215                 220

<210> SEQ ID NO 82
<211> LENGTH: 780
<212> TYPE: DNA
<213> ORGANISM: Canis familiaris
<220> FEATURE:
<221> NAME/KEY: CDS
<222> LOCATION: (1)..(618)
<223> OTHER INFORMATION:

<400> SEQUENCE: 82
```

| | | | | | | | | | | | | | | | | |
|---|---|---|---|---|---|---|---|---|---|---|---|---|---|---|---|---|
| atg | tca | gtg | gcc | ctg | gga | cag | atg | gcc | agg | atc | acc | tgt | ggg | aga | gac | 48 |
| Met | Ser | Val | Ala | Leu | Gly | Gln | Met | Ala | Arg | Ile | Thr | Cys | Gly | Arg | Asp | |
| 1 | | | | 5 | | | | | 10 | | | | | 15 | | |
| aac | tct | gga | aga | aaa | agt | gct | cac | tgg | tac | cag | cag | aag | cca | agc | cag | 96 |
| Asn | Ser | Gly | Arg | Lys | Ser | Ala | His | Trp | Tyr | Gln | Gln | Lys | Pro | Ser | Gln | |
| | | | 20 | | | | | 25 | | | | | 30 | | | |
| gct | ccc | gtg | atg | ctt | atc | gat | gat | gat | tgc | ttc | cag | ccc | tca | gga | ttc | 144 |
| Ala | Pro | Val | Met | Leu | Ile | Asp | Asp | Asp | Cys | Phe | Gln | Pro | Ser | Gly | Phe | |
| | | 35 | | | | | 40 | | | | | 45 | | | | |
| tct | gag | caa | ttc | tca | ggc | act | aac | tcg | ggg | aac | aca | gcc | acc | ctg | acc | 192 |
| Ser | Glu | Gln | Phe | Ser | Gly | Thr | Asn | Ser | Gly | Asn | Thr | Ala | Thr | Leu | Thr | |
| | 50 | | | | | 55 | | | | | 60 | | | | | |
| att | aaa | gaa | atg | gac | gca | ttc | ctg | gaa | acc | tcc | ttc | tat | tgc | tgg | atg | 240 |
| Ile | Lys | Glu | Met | Asp | Ala | Phe | Leu | Glu | Thr | Ser | Phe | Tyr | Cys | Trp | Met | |
| 65 | | | | | 70 | | | | | 75 | | | | | 80 | |
| tgg | cag | cct | gaa | tca | cag | tgt | tgg | gta | ttc | ggt | gaa | ggg | acc | cag | ctg | 288 |
| Trp | Gln | Pro | Glu | Ser | Gln | Cys | Trp | Val | Phe | Gly | Glu | Gly | Thr | Gln | Leu | |
| | | | | 85 | | | | | 90 | | | | | 95 | | |
| acc | gtc | ctc | ggt | cag | ccc | aag | tcc | tcc | ccc | ttg | gtc | aca | ctc | ttc | ccg | 336 |
| Thr | Val | Leu | Gly | Gln | Pro | Lys | Ser | Ser | Pro | Leu | Val | Thr | Leu | Phe | Pro | |
| | | | 100 | | | | | 105 | | | | | 110 | | | |
| ccc | tcc | tct | gag | gag | ctc | ggc | gcc | aac | aag | gct | acc | ctg | gtg | tgc | ctc | 384 |
| Pro | Ser | Ser | Glu | Glu | Leu | Gly | Ala | Asn | Lys | Ala | Thr | Leu | Val | Cys | Leu | |
| | | 115 | | | | | 120 | | | | | 125 | | | | |
| atc | agc | gac | ttc | tac | ccc | agt | ggc | ctg | aaa | gtg | gct | tgg | aag | gca | gat | 432 |
| Ile | Ser | Asp | Phe | Tyr | Pro | Ser | Gly | Leu | Lys | Val | Ala | Trp | Lys | Ala | Asp | |
| | 130 | | | | | 135 | | | | | 140 | | | | | |
| ggc | agc | acc | atc | atc | cag | ggc | gtg | gaa | acc | acc | aag | ccc | tcc | aag | cag | 480 |
| Gly | Ser | Thr | Ile | Ile | Gln | Gly | Val | Glu | Thr | Thr | Lys | Pro | Ser | Lys | Gln | |
| 145 | | | | | 150 | | | | | 155 | | | | | 160 | |
| agc | aac | aac | aag | tac | acg | gcc | agc | agc | tac | ctg | agc | ctg | acg | cct | gac | 528 |
| Ser | Asn | Asn | Lys | Tyr | Thr | Ala | Ser | Ser | Tyr | Leu | Ser | Leu | Thr | Pro | Asp | |
| | | | | 165 | | | | | 170 | | | | | 175 | | |
| aag | tgg | aaa | tct | cac | agc | agc | ttc | agc | tgc | ctg | gtc | acg | cac | cag | ggg | 576 |
| Lys | Trp | Lys | Ser | His | Ser | Ser | Phe | Ser | Cys | Leu | Val | Thr | His | Gln | Gly | |
| | | | 180 | | | | | 185 | | | | | 190 | | | |
| agc | acc | gtg | gag | aag | aag | gtg | gcc | cct | gca | gag | tgc | tct | tag | | | 618 |
| Ser | Thr | Val | Glu | Lys | Lys | Val | Ala | Pro | Ala | Glu | Cys | Ser | | | | |

```
                    195                 200                 205
gtccctgaga attcctgaga tggagccttc ctcacccaga caccccttcc ccagttcacc      678
ttgtgcccct gaaaacccac cctggaccag ctcagaccag gcaggtcact catcctccct      738
gtttctactt gtgctcaata aagactttat catttatcac tg                        780

<210> SEQ ID NO 83
<211> LENGTH: 205
<212> TYPE: PRT
<213> ORGANISM: Canis familiaris

<400> SEQUENCE: 83

Met Ser Val Ala Leu Gly Gln Met Ala Arg Ile Thr Cys Gly Arg Asp
1               5                   10                  15

Asn Ser Gly Arg Lys Ser Ala His Trp Tyr Gln Gln Lys Pro Ser Gln
            20                  25                  30

Ala Pro Val Met Leu Ile Asp Asp Asp Cys Phe Gln Pro Ser Gly Phe
        35                  40                  45

Ser Glu Gln Phe Ser Gly Thr Asn Ser Gly Asn Thr Ala Thr Leu Thr
    50                  55                  60

Ile Lys Glu Met Asp Ala Phe Leu Glu Thr Ser Phe Tyr Cys Trp Met
65                  70                  75                  80

Trp Gln Pro Glu Ser Gln Cys Trp Val Phe Gly Glu Gly Thr Gln Leu
                85                  90                  95

Thr Val Leu Gly Gln Pro Lys Ser Ser Pro Leu Val Thr Leu Phe Pro
            100                 105                 110

Pro Ser Ser Glu Glu Leu Gly Ala Asn Lys Ala Thr Leu Val Cys Leu
        115                 120                 125

Ile Ser Asp Phe Tyr Pro Ser Gly Leu Lys Val Ala Trp Lys Ala Asp
    130                 135                 140

Gly Ser Thr Ile Ile Gln Gly Val Glu Thr Thr Lys Pro Ser Lys Gln
145                 150                 155                 160

Ser Asn Asn Lys Tyr Thr Ala Ser Ser Tyr Leu Ser Leu Thr Pro Asp
                165                 170                 175

Lys Trp Lys Ser His Ser Ser Phe Ser Cys Leu Val Thr His Gln Gly
            180                 185                 190

Ser Thr Val Glu Lys Lys Val Ala Pro Ala Glu Cys Ser
        195                 200                 205

<210> SEQ ID NO 84
<211> LENGTH: 786
<212> TYPE: DNA
<213> ORGANISM: Canis familiaris
<220> FEATURE:
<221> NAME/KEY: CDS
<222> LOCATION: (1)..(624)
<223> OTHER INFORMATION:

<400> SEQUENCE: 84 atg tca gtg gcc ctg gga cag atg gcc agg atc acc tgt ggg aga gac       48
Met Ser Val Ala Leu Gly Gln Met Ala Arg Ile Thr Cys Gly Arg Asp
1               5                   10                  15 aac tct gga aga aaa agt gct cac tgg tac cag cag aag cca agc cag       96
Asn Ser Gly Arg Lys Ser Ala His Trp Tyr Gln Gln Lys Pro Ser Gln
            20                  25                  30 gct ccc gtg atg ctt atc gat gat gat tgc ttc cag ccc tca gga ttc      144
Ala Pro Val Met Leu Ile Asp Asp Asp Cys Phe Gln Pro Ser Gly Phe
        35                  40                  45
```

```
tct gag caa ttc tca ggc act aac tcg ggg aac aca gcc acc ctg acc      192
Ser Glu Gln Phe Ser Gly Thr Asn Ser Gly Asn Thr Ala Thr Leu Thr
     50                  55                  60 att agt gtg tca aac att gac gac acg ctt tac ata tat aga acg gaa      240
Ile Ser Val Ser Asn Ile Asp Asp Thr Leu Tyr Ile Tyr Arg Thr Glu
65                  70                  75                  80 gtg agc aac att cct gaa tca cag tgt tgg gta ttc ggt gaa ggg acc      288
Val Ser Asn Ile Pro Glu Ser Gln Cys Trp Val Phe Gly Glu Gly Thr
                85                  90                  95 cag ctg acc gtc ctc ggt cag ccc aag tcc tcc ccc ttg gtc aca ctc      336
Gln Leu Thr Val Leu Gly Gln Pro Lys Ser Ser Pro Leu Val Thr Leu
            100                 105                 110 ttc ccg ccc tcc tct gag gag ctc ggc gcc aac aag gct acc ctg gtg      384
Phe Pro Pro Ser Ser Glu Glu Leu Gly Ala Asn Lys Ala Thr Leu Val
        115                 120                 125 tgc ctc atc agc gac ttc tac ccc agt ggc ctg aaa gtg gct tgg aag      432
Cys Leu Ile Ser Asp Phe Tyr Pro Ser Gly Leu Lys Val Ala Trp Lys
    130                 135                 140 gca gat ggc agc acc atc atc cag ggc gtg gaa acc acc aag ccc tcc      480
Ala Asp Gly Ser Thr Ile Ile Gln Gly Val Glu Thr Thr Lys Pro Ser
145                 150                 155                 160 aag cag agc aac aac aag tac acg gcc agc agc tac ctg agc ctg acg      528
Lys Gln Ser Asn Asn Lys Tyr Thr Ala Ser Ser Tyr Leu Ser Leu Thr
                165                 170                 175 cct gac aag tgg aaa tct cac agc agc ttc agc tgc ctg gtc acg cac      576
Pro Asp Lys Trp Lys Ser His Ser Ser Phe Ser Cys Leu Val Thr His
            180                 185                 190 cag ggg agc acc gtg gag aag aag gtg gcc cct gca gag tgc tct tag      624
Gln Gly Ser Thr Val Glu Lys Lys Val Ala Pro Ala Glu Cys Ser
        195                 200                 205 gtccctgaga attcctgaga tggagccttc ctcacccaga caccccttcc ccagttcacc    684
ttgtgcccct gaaacccac cctggaccag ctcagaccag gcaggtcact catcctccct    744
gtttctactt gtgctcaata aagactttat catttatcac tg                      786

<210> SEQ ID NO 85
<211> LENGTH: 207
<212> TYPE: PRT
<213> ORGANISM: Canis familiaris

<400> SEQUENCE: 85

Met Ser Val Ala Leu Gly Gln Met Ala Arg Ile Thr Cys Gly Arg Asp
1               5                   10                  15

Asn Ser Gly Arg Lys Ser Ala His Trp Tyr Gln Gln Lys Pro Ser Gln
                20                  25                  30

Ala Pro Val Met Leu Ile Asp Asp Cys Phe Gln Pro Ser Gly Phe
            35                  40                  45

Ser Glu Gln Phe Ser Gly Thr Asn Ser Gly Asn Thr Ala Thr Leu Thr
     50                  55                  60

Ile Ser Val Ser Asn Ile Asp Asp Thr Leu Tyr Ile Tyr Arg Thr Glu
65                  70                  75                  80

Val Ser Asn Ile Pro Glu Ser Gln Cys Trp Val Phe Gly Glu Gly Thr
                85                  90                  95

Gln Leu Thr Val Leu Gly Gln Pro Lys Ser Ser Pro Leu Val Thr Leu
            100                 105                 110

Phe Pro Pro Ser Ser Glu Glu Leu Gly Ala Asn Lys Ala Thr Leu Val
        115                 120                 125

Cys Leu Ile Ser Asp Phe Tyr Pro Ser Gly Leu Lys Val Ala Trp Lys
```

```
                    130                 135                 140
Ala Asp Gly Ser Thr Ile Ile Gln Gly Val Glu Thr Thr Lys Pro Ser
145                 150                 155                 160

Lys Gln Ser Asn Asn Lys Tyr Thr Ala Ser Ser Tyr Leu Ser Leu Thr
                165                 170                 175

Pro Asp Lys Trp Lys Ser His Ser Ser Phe Ser Cys Leu Val Thr His
            180                 185                 190

Gln Gly Ser Thr Val Glu Lys Lys Val Ala Pro Ala Glu Cys Ser
        195                 200                 205

<210> SEQ ID NO 86
<211> LENGTH: 783
<212> TYPE: DNA
<213> ORGANISM: Canis familiaris
<220> FEATURE:
<221> NAME/KEY: CDS
<222> LOCATION: (1)..(621)
<223> OTHER INFORMATION:

<400> SEQUENCE: 86 atg tca gtg gcc ctg gga cag atg gcc agg atc acc tgt ggg aga gac     48
Met Ser Val Ala Leu Gly Gln Met Ala Arg Ile Thr Cys Gly Arg Asp
1               5                   10                  15 aac tct gga aga aaa agt gct cac tgg tac cag cag aag cca agc cag     96
Asn Ser Gly Arg Lys Ser Ala His Trp Tyr Gln Gln Lys Pro Ser Gln
            20                  25                  30 gct ccc gtg atg ctt atc gat gat gat tgc ttc cag ccc tca gga ttc    144
Ala Pro Val Met Leu Ile Asp Asp Asp Cys Phe Gln Pro Ser Gly Phe
        35                  40                  45 tct gag caa ttc tca ggc act aac tcg ggg aac aca gcc acc ctg acc    192
Ser Glu Gln Phe Ser Gly Thr Asn Ser Gly Asn Thr Ala Thr Leu Thr
    50                  55                  60 att agt gga cac cgt gca gaa cca gag gca gaa cat ttc tct ctg tgg    240
Ile Ser Gly His Arg Ala Glu Pro Glu Ala Glu His Phe Ser Leu Trp
65                  70                  75                  80 cca tgc aag tca gat cct ggt tgt tgg gta ttc ggt gaa ggg acc cag    288
Pro Cys Lys Ser Asp Pro Gly Cys Trp Val Phe Gly Glu Gly Thr Gln
                85                  90                  95 ctg acc gtc ctc ggt cag ccc aag tcc tcc ccc ttg gtc aca ctc ttc    336
Leu Thr Val Leu Gly Gln Pro Lys Ser Ser Pro Leu Val Thr Leu Phe
            100                 105                 110 ccg ccc tcc tct gag gag ctc ggc gcc aac aag gct acc ctg gtg tgc    384
Pro Pro Ser Ser Glu Glu Leu Gly Ala Asn Lys Ala Thr Leu Val Cys
        115                 120                 125 ctc atc agc gac ttc tac ccc agt ggc ctg aaa gtg gct tgg aag gca    432
Leu Ile Ser Asp Phe Tyr Pro Ser Gly Leu Lys Val Ala Trp Lys Ala
    130                 135                 140 gat ggc agc acc atc atc cag ggc gtg gaa acc acc aag ccc tcc aag    480
Asp Gly Ser Thr Ile Ile Gln Gly Val Glu Thr Thr Lys Pro Ser Lys
145                 150                 155                 160 cag agc aac aac aag tac acg gcc agc agc tac ctg agc ctg acg cct    528
Gln Ser Asn Asn Lys Tyr Thr Ala Ser Ser Tyr Leu Ser Leu Thr Pro
                165                 170                 175 gac aag tgg aaa tct cac agc agc ttc agc tgc ctg gtc acg cac cag    576
Asp Lys Trp Lys Ser His Ser Ser Phe Ser Cys Leu Val Thr His Gln
            180                 185                 190 ggg agc acc gtg gag aag aag gtg gcc cct gca gag tgc tct tag        621
Gly Ser Thr Val Glu Lys Lys Val Ala Pro Ala Glu Cys Ser
        195                 200                 205 gtccctgaga attcctgaga tggagccttc ctcacccaga caccccttcc ccagttcacc    681
```

```
ttgtgccct gaaacccac cctggaccag ctcagaccag gcaggtcact catcctccct    741
gtttctactt gtgctcaata aagactttat catttatcac tg                     783
```

<210> SEQ ID NO 87
<211> LENGTH: 206
<212> TYPE: PRT
<213> ORGANISM: Canis familiaris

<400> SEQUENCE: 87

```
Met Ser Val Ala Leu Gly Gln Met Ala Arg Ile Thr Cys Gly Arg Asp
1               5                   10                  15

Asn Ser Gly Arg Lys Ser Ala His Trp Tyr Gln Gln Lys Pro Ser Gln
            20                  25                  30

Ala Pro Val Met Leu Ile Asp Asp Asp Cys Phe Gln Pro Ser Gly Phe
        35                  40                  45

Ser Glu Gln Phe Ser Gly Thr Asn Ser Gly Asn Thr Ala Thr Leu Thr
    50                  55                  60

Ile Ser Gly His Arg Ala Glu Pro Glu Ala Glu His Phe Ser Leu Trp
65                  70                  75                  80

Pro Cys Lys Ser Asp Pro Gly Cys Trp Val Phe Gly Glu Gly Thr Gln
                85                  90                  95

Leu Thr Val Leu Gly Gln Pro Lys Ser Ser Pro Leu Val Thr Leu Phe
            100                 105                 110

Pro Pro Ser Ser Glu Glu Leu Gly Ala Asn Lys Ala Thr Leu Val Cys
        115                 120                 125

Leu Ile Ser Asp Phe Tyr Pro Ser Gly Leu Lys Val Ala Trp Lys Ala
    130                 135                 140

Asp Gly Ser Thr Ile Ile Gln Gly Val Glu Thr Thr Lys Pro Ser Lys
145                 150                 155                 160

Gln Ser Asn Asn Lys Tyr Thr Ala Ser Ser Tyr Leu Ser Leu Thr Pro
                165                 170                 175

Asp Lys Trp Lys Ser His Ser Ser Phe Ser Cys Leu Val Thr His Gln
            180                 185                 190

Gly Ser Thr Val Glu Lys Lys Val Ala Pro Ala Glu Cys Ser
        195                 200                 205
```

<210> SEQ ID NO 88
<211> LENGTH: 780
<212> TYPE: DNA
<213> ORGANISM: Canis familiaris
<220> FEATURE:
<221> NAME/KEY: CDS
<222> LOCATION: (1)..(618)
<223> OTHER INFORMATION:

<400> SEQUENCE: 88

```
atg tca gtg gcc ctg gga cag atg gcc agg atc acc tgt ggg aga gac    48
Met Ser Val Ala Leu Gly Gln Met Ala Arg Ile Thr Cys Gly Arg Asp
1               5                   10                  15 aac tct gga aga aaa agt gct cac tgg tac cag cag aag cca agc cag    96
Asn Ser Gly Arg Lys Ser Ala His Trp Tyr Gln Gln Lys Pro Ser Gln
            20                  25                  30 gct ccc gtg atg ctt atc gat gat gat tgc ttc cag ccc tca gga ttc   144
Ala Pro Val Met Leu Ile Asp Asp Asp Cys Phe Gln Pro Ser Gly Phe
        35                  40                  45 tct gag caa ttc tca ggc act aac tcg ggg aac aca gcc acc ctg acc   192
Ser Glu Gln Phe Ser Gly Thr Asn Ser Gly Asn Thr Ala Thr Leu Thr
    50                  55                  60
```

```
att agt cag atc cca ccc tac tct gaa gtg act cgc ttc act cgg gcc     240
Ile Ser Gln Ile Pro Pro Tyr Ser Glu Val Thr Arg Phe Thr Arg Ala
65                  70                  75                  80 tgg gca gac act agc tgt tgt tgg gta ttc ggt gaa ggg acc cag ctg     288
Trp Ala Asp Thr Ser Cys Cys Trp Val Phe Gly Glu Gly Thr Gln Leu
                85                  90                  95 acc gtc ctc ggt cag ccc aag tcc tcc ccc ttg gtc aca ctc ttc ccg     336
Thr Val Leu Gly Gln Pro Lys Ser Ser Pro Leu Val Thr Leu Phe Pro
            100                 105                 110 ccc tcc tct gag gag ctc ggc gcc aac aag gct acc ctg gtg tgc ctc     384
Pro Ser Ser Glu Glu Leu Gly Ala Asn Lys Ala Thr Leu Val Cys Leu
        115                 120                 125 atc agc gac ttc tac ccc agt ggc ctg aaa gtg gct tgg aag gca gat     432
Ile Ser Asp Phe Tyr Pro Ser Gly Leu Lys Val Ala Trp Lys Ala Asp
130                 135                 140 ggc agc acc atc atc cag ggc gtg gaa acc acc aag ccc tcc aag cag     480
Gly Ser Thr Ile Ile Gln Gly Val Glu Thr Thr Lys Pro Ser Lys Gln
145                 150                 155                 160 agc aac aac aag tac acg gcc agc agc tac ctg agc ctg acg cct gac     528
Ser Asn Asn Lys Tyr Thr Ala Ser Ser Tyr Leu Ser Leu Thr Pro Asp
                165                 170                 175 aag tgg aaa tct cac agc agc ttc agc tgc ctg gtc acg cac cag ggg     576
Lys Trp Lys Ser His Ser Ser Phe Ser Cys Leu Val Thr His Gln Gly
            180                 185                 190 agc acc gtg gag aag aag gtg gcc cct gca gag tgc tct tag             618
Ser Thr Val Glu Lys Lys Val Ala Pro Ala Glu Cys Ser
        195                 200                 205 gtccctgaga attcctgaga tggagccttc ctcacccaga caccccttcc ccagttcacc    678
ttgtgcccct gaaacccac cctggaccag ctcagaccag gcaggtcact catcctccct     738
gtttctactt gtgctcaata aagactttat catttatcac tg                       780

<210> SEQ ID NO 89
<211> LENGTH: 205
<212> TYPE: PRT
<213> ORGANISM: Canis familiaris

<400> SEQUENCE: 89

Met Ser Val Ala Leu Gly Gln Met Ala Arg Ile Thr Cys Gly Arg Asp
1               5                   10                  15

Asn Ser Gly Arg Lys Ser Ala His Trp Tyr Gln Gln Lys Pro Ser Gln
            20                  25                  30

Ala Pro Val Met Leu Ile Asp Asp Asp Cys Phe Gln Pro Ser Gly Phe
        35                  40                  45

Ser Glu Gln Phe Ser Gly Thr Asn Ser Gly Asn Thr Ala Thr Leu Thr
    50                  55                  60

Ile Ser Gln Ile Pro Pro Tyr Ser Glu Val Thr Arg Phe Thr Arg Ala
65                  70                  75                  80

Trp Ala Asp Thr Ser Cys Cys Trp Val Phe Gly Glu Gly Thr Gln Leu
                85                  90                  95

Thr Val Leu Gly Gln Pro Lys Ser Ser Pro Leu Val Thr Leu Phe Pro
            100                 105                 110

Pro Ser Ser Glu Glu Leu Gly Ala Asn Lys Ala Thr Leu Val Cys Leu
        115                 120                 125

Ile Ser Asp Phe Tyr Pro Ser Gly Leu Lys Val Ala Trp Lys Ala Asp
130                 135                 140

Gly Ser Thr Ile Ile Gln Gly Val Glu Thr Thr Lys Pro Ser Lys Gln
```

```
                145                 150                 155                 160
Ser Asn Asn Lys Tyr Thr Ala Ser Ser Tyr Leu Ser Leu Thr Pro Asp
                165                 170                 175
Lys Trp Lys Ser His Ser Ser Phe Ser Cys Leu Val Thr His Gln Gly
            180                 185                 190
Ser Thr Val Glu Lys Lys Val Ala Pro Ala Glu Cys Ser
        195                 200                 205

<210> SEQ ID NO 90
<211> LENGTH: 851
<212> TYPE: DNA
<213> ORGANISM: Canis familiaris
<220> FEATURE:
<221> NAME/KEY: CDS
<222> LOCATION: (24)..(719)
<223> OTHER INFORMATION:

<400> SEQUENCE: 90
agcagaatca gggtgcctcc acc atg gcc tgg acc cac ctc ctc ctg agc ctc       53
                        Met Ala Trp Thr His Leu Leu Leu Ser Leu
                         1               5                  10 ctg gct ctc tgc aca ggt tct gtg gcc tcc tat gtg ctg aca cag ctg        101
Leu Ala Leu Cys Thr Gly Ser Val Ala Ser Tyr Val Leu Thr Gln Leu
                15                  20                  25 cca tcc aaa aat gtg acc ctg aag cag ccg gcc cac atc acc tgt ggg        149
Pro Ser Lys Asn Val Thr Leu Lys Gln Pro Ala His Ile Thr Cys Gly
         30                  35                  40 gga gac aac att gga agt aaa agt gtt cac tgg tac cag cag aag ctg        197
Gly Asp Asn Ile Gly Ser Lys Ser Val His Trp Tyr Gln Gln Lys Leu
     45                  50                  55 ggc cag gcc cct gta ctg att atc tat tat gat agc agc agg ccg aca        245
Gly Gln Ala Pro Val Leu Ile Ile Tyr Tyr Asp Ser Ser Arg Pro Thr
 60                  65                  70 ggg atc cct gag cga ttc tcc ggc gcc aac tcg ggg aac acg gcc acc        293
Gly Ile Pro Glu Arg Phe Ser Gly Ala Asn Ser Gly Asn Thr Ala Thr
 75                  80                  85                  90 ctg acc atc agc ggg gcc ctg gcc gag gac gag gct gac tat tac tgc        341
Leu Thr Ile Ser Gly Ala Leu Ala Glu Asp Glu Ala Asp Tyr Tyr Cys
                 95                 100                 105 cag gtg tgg gac agc agt gct ctt gtg ttc ggc gga ggc acc cat ctg        389
Gln Val Trp Asp Ser Ser Ala Leu Val Phe Gly Gly Gly Thr His Leu
             110                 115                 120 acc gtc ctc ggt cag ccc aag gcc tcc ccc tcg gtc aca ctc ttc ccg        437
Thr Val Leu Gly Gln Pro Lys Ala Ser Pro Ser Val Thr Leu Phe Pro
         125                 130                 135 ccc tcc tct gag gag ctc ggc gcc aac aag gcc acc ctg gtg tgc ctc        485
Pro Ser Ser Glu Glu Leu Gly Ala Asn Lys Ala Thr Leu Val Cys Leu
     140                 145                 150 atc agc gac ttc tac ccc agt ggc gtg acg gtg gcc tgg aag gca gac        533
Ile Ser Asp Phe Tyr Pro Ser Gly Val Thr Val Ala Trp Lys Ala Asp
155                 160                 165                 170 ggc agc ccc gtc acc cag ggc gtg gag acc acc aag ccc tcc aag cag        581
Gly Ser Pro Val Thr Gln Gly Val Glu Thr Thr Lys Pro Ser Lys Gln
                175                 180                 185 agc aac aac aag tac gcg gcc agc agc tac ctg agc ctg acg cct gac        629
Ser Asn Asn Lys Tyr Ala Ala Ser Ser Tyr Leu Ser Leu Thr Pro Asp
            190                 195                 200 aag tgg aaa tct cac agc agc ttc agc tgc ctg gtc aca cac gag ggg        677
Lys Trp Lys Ser His Ser Ser Phe Ser Cys Leu Val Thr His Glu Gly
        205                 210                 215
```

```
agc acc gtg gag aag aag gtg gcc ccc gca gag tgc tct tag        719
Ser Thr Val Glu Lys Lys Val Ala Pro Ala Glu Cys Ser
    220             225                 230 gttcccgacg cccccgccca cctaagggggg cccggagcct caggacctcc aggaggatct  779
tgcctcctat ctgggtcatc ccgcccttct ccccacaccc aggcagcact caataaagtg  839
ttctttgttc aa                                                      851

<210> SEQ ID NO 91
<211> LENGTH: 231
<212> TYPE: PRT
<213> ORGANISM: Canis familiaris

<400> SEQUENCE: 91

Met Ala Trp Thr His Leu Leu Leu Ser Leu Leu Ala Leu Cys Thr Gly
1               5                   10                  15

Ser Val Ala Ser Tyr Val Leu Thr Gln Leu Pro Ser Lys Asn Val Thr
            20                  25                  30

Leu Lys Gln Pro Ala His Ile Thr Cys Gly Gly Asp Asn Ile Gly Ser
        35                  40                  45

Lys Ser Val His Trp Tyr Gln Gln Lys Leu Gly Gln Ala Pro Val Leu
    50                  55                  60

Ile Ile Tyr Tyr Asp Ser Ser Arg Pro Thr Gly Ile Pro Glu Arg Phe
65                  70                  75                  80

Ser Gly Ala Asn Ser Gly Asn Thr Ala Thr Leu Thr Ile Ser Gly Ala
                85                  90                  95

Leu Ala Glu Asp Glu Ala Asp Tyr Tyr Cys Gln Val Trp Asp Ser Ser
            100                 105                 110

Ala Leu Val Phe Gly Gly Gly Thr His Leu Thr Val Leu Gly Gln Pro
        115                 120                 125

Lys Ala Ser Pro Ser Val Thr Leu Phe Pro Pro Ser Ser Glu Glu Leu
    130                 135                 140

Gly Ala Asn Lys Ala Thr Leu Val Cys Leu Ile Ser Asp Phe Tyr Pro
145                 150                 155                 160

Ser Gly Val Thr Val Ala Trp Lys Ala Asp Gly Ser Pro Val Thr Gln
                165                 170                 175

Gly Val Glu Thr Thr Lys Pro Ser Lys Gln Ser Asn Asn Lys Tyr Ala
            180                 185                 190

Ala Ser Ser Tyr Leu Ser Leu Thr Pro Asp Lys Trp Lys Ser His Ser
        195                 200                 205

Ser Phe Ser Cys Leu Val Thr His Glu Gly Ser Thr Val Glu Lys Lys
    210                 215                 220

Val Ala Pro Ala Glu Cys Ser
225                 230

<210> SEQ ID NO 92
<211> LENGTH: 881
<212> TYPE: DNA
<213> ORGANISM: Canis familiaris
<220> FEATURE:
<221> NAME/KEY: CDS
<222> LOCATION: (18)..(719)
<223> OTHER INFORMATION:

<400> SEQUENCE: 92
atcagggtgc ctccacc atg gcc tgg acc cac ctc ctc ctg agc ctc ctg      50
                   Met Ala Trp Thr His Leu Leu Leu Ser Leu Leu
                   1               5                   10
```

```
gct ctc tgc aca ggt tct gtg gcc tcc tat gtg ctg aca cag ctg cca    98
Ala Leu Cys Thr Gly Ser Val Ala Ser Tyr Val Leu Thr Gln Leu Pro
            15                  20                  25 tcc aaa aat gtg acc ctg aag cag ccg gcc cac atc acc tgt ggg gga   146
Ser Lys Asn Val Thr Leu Lys Gln Pro Ala His Ile Thr Cys Gly Gly
        30                  35                  40 gac aac att gga agt aaa agt gtt cac tgg tac cag cag aag ctg ggc   194
Asp Asn Ile Gly Ser Lys Ser Val His Trp Tyr Gln Gln Lys Leu Gly
    45                  50                  55 cag gcc cct gta ctg att atc tat tat gat agc agc agg ccg aca ggg   242
Gln Ala Pro Val Leu Ile Ile Tyr Tyr Asp Ser Ser Arg Pro Thr Gly
60                  65                  70                  75 atc cct gag cga ttc tcc ggc gcc aac tcg ggg aac acg gcc acc ctg   290
Ile Pro Glu Arg Phe Ser Gly Ala Asn Ser Gly Asn Thr Ala Thr Leu
                80                  85                  90 acc atc agc ggg gcc ctg gcc gag gac gag gct gac tat tac tgc cag   338
Thr Ile Ser Gly Ala Leu Ala Glu Asp Glu Ala Asp Tyr Tyr Cys Gln
            95                 100                 105 gtg tgg gac agc agt ggt cat tgt tgg gta ttc ggt gaa ggg acc cag   386
Val Trp Asp Ser Ser Gly His Cys Trp Val Phe Gly Glu Gly Thr Gln
        110                 115                 120 ctg acc gtc ctc ggt cag ccc aag tcc tcc ccc ttg gtc aca ctc ttc   434
Leu Thr Val Leu Gly Gln Pro Lys Ser Ser Pro Leu Val Thr Leu Phe
    125                 130                 135 ccg ccc tcc tct gag gag ctc ggc gcc aac aag gct acc ctg gtg tgc   482
Pro Pro Ser Ser Glu Glu Leu Gly Ala Asn Lys Ala Thr Leu Val Cys
140                 145                 150                 155 ctc atc agc gac ttc tac ccc agt ggc ctg aaa gtg gct tgg aag gca   530
Leu Ile Ser Asp Phe Tyr Pro Ser Gly Leu Lys Val Ala Trp Lys Ala
                160                 165                 170 gat ggc agc acc atc atc cag ggc gtg gaa acc acc aag ccc tcc aag   578
Asp Gly Ser Thr Ile Ile Gln Gly Val Glu Thr Thr Lys Pro Ser Lys
            175                 180                 185 cag agc aac aac aag tac acg gcc agc agc tac ctg agc ctg acg cct   626
Gln Ser Asn Asn Lys Tyr Thr Ala Ser Ser Tyr Leu Ser Leu Thr Pro
        190                 195                 200 gac aag tgg aaa tct cac agc agc ttc agc tgc ctg gtc acg cac cag   674
Asp Lys Trp Lys Ser His Ser Ser Phe Ser Cys Leu Val Thr His Gln
    205                 210                 215 ggg agc acc gtg gag aag aag gtg gcc cct gca gag tgc tct tag       719
Gly Ser Thr Val Glu Lys Lys Val Ala Pro Ala Glu Cys Ser
220                 225                 230 gtccctgaga attcctgaga tggagccttc ctcacccaga caccccttcc ccagttcacc   779
ttgtgcccct gaaacccac cctggaccag ctcagaccag gcaggtcact catcctccct     839
gtttctactt gtgctcaata aagactttat catttatcac tg                      881

<210> SEQ ID NO 93
<211> LENGTH: 233
<212> TYPE: PRT
<213> ORGANISM: Canis familiaris

<400> SEQUENCE: 93

Met Ala Trp Thr His Leu Leu Leu Ser Leu Leu Ala Leu Cys Thr Gly
1               5                   10                  15

Ser Val Ala Ser Tyr Val Leu Thr Gln Leu Pro Ser Lys Asn Val Thr
            20                  25                  30

Leu Lys Gln Pro Ala His Ile Thr Cys Gly Gly Asp Asn Ile Gly Ser
        35                  40                  45
```

```
Lys Ser Val His Trp Tyr Gln Gln Lys Leu Gly Gln Ala Pro Val Leu
    50                  55                  60

Ile Ile Tyr Tyr Asp Ser Ser Arg Pro Thr Gly Ile Pro Glu Arg Phe
65                  70                  75                  80

Ser Gly Ala Asn Ser Gly Asn Thr Ala Thr Leu Thr Ile Ser Gly Ala
                85                  90                  95

Leu Ala Glu Asp Glu Ala Asp Tyr Tyr Cys Gln Val Trp Asp Ser Ser
            100                 105                 110

Gly His Cys Trp Val Phe Gly Gly Thr Gln Leu Thr Val Leu Gly
        115                 120                 125

Gln Pro Lys Ser Ser Pro Leu Val Thr Leu Phe Pro Pro Ser Ser Glu
    130                 135                 140

Glu Leu Gly Ala Asn Lys Ala Thr Leu Val Cys Leu Ile Ser Asp Phe
145                 150                 155                 160

Tyr Pro Ser Gly Leu Lys Val Ala Trp Lys Ala Asp Gly Ser Thr Ile
                165                 170                 175

Ile Gln Gly Val Glu Thr Thr Lys Pro Ser Lys Gln Ser Asn Asn Lys
            180                 185                 190

Tyr Thr Ala Ser Ser Tyr Leu Ser Leu Thr Pro Asp Lys Trp Lys Ser
        195                 200                 205

His Ser Ser Phe Ser Cys Leu Val Thr His Gln Gly Ser Thr Val Glu
    210                 215                 220

Lys Lys Val Ala Pro Ala Glu Cys Ser
225                 230

<210> SEQ ID NO 94
<211> LENGTH: 935
<212> TYPE: DNA
<213> ORGANISM: Bos taurus
<220> FEATURE:
<221> NAME/KEY: CDS
<222> LOCATION: (55)..(762)
<223> OTHER INFORMATION:

<400> SEQUENCE: 94
ggctctgctc agctgtgggg ccacagacgg caggacgccc tgaccatgtc cacc atg      57
                                                              Met
                                                              1 gcc tgg tcc cct ctg ctc ctc acc ctg gtc gct ctc tgc aca gga tcc     105
Ala Trp Ser Pro Leu Leu Leu Thr Leu Val Ala Leu Cys Thr Gly Ser
        5                  10                  15 tgg gcc cag gct gtg ctg act cag ccg tcc tcc gtg tcc ggc tcc ctg     153
Trp Ala Gln Ala Val Leu Thr Gln Pro Ser Ser Val Ser Gly Ser Leu
    20                  25                  30 ggc cag agg gtc tcc atc acc tgc tct gga agc agc acg aat atc ggc     201
Gly Gln Arg Val Ser Ile Thr Cys Ser Gly Ser Ser Thr Asn Ile Gly
35                  40                  45 att tat ggt gta aac tgg tac caa cag gtc cca gga tcg ggc ctc aaa     249
Ile Tyr Gly Val Asn Trp Tyr Gln Gln Val Pro Gly Ser Gly Leu Lys
50                  55                  60                  65 acc atc atc tat gaa gat aag tat cga ccc tcg ggg gtc ccc gac cga     297
Thr Ile Ile Tyr Glu Asp Lys Tyr Arg Pro Ser Gly Val Pro Asp Arg
                70                  75                  80 ttc tcc ggc tcc aag tct ggc aac aca gcc acc cta acc atc aac tcg     345
Phe Ser Gly Ser Lys Ser Gly Asn Thr Ala Thr Leu Thr Ile Asn Ser
            85                  90                  95 ctc cag gct gag gac gag gcg gat tat ttc tgt gca gct ggt gac tac     393
Leu Gln Ala Glu Asp Glu Ala Asp Tyr Phe Cys Ala Ala Gly Asp Tyr
        100                 105                 110
```

```
agt gtc aat act gcc gtt ttc ggc ggc ggg acc aca ctg acc gtc ctg        441
Ser Val Asn Thr Ala Val Phe Gly Gly Gly Thr Thr Leu Thr Val Leu
    115                 120                 125 ggt cag ccc aag tcc cca ccc tcg gtc acc ctg ttc ccg ccc tcc acg        489
Gly Gln Pro Lys Ser Pro Pro Ser Val Thr Leu Phe Pro Pro Ser Thr
130                 135                 140                 145 gag gag ctc aac ggc aac aag gcc acc ctg gtg tgt ctc atc agc gac        537
Glu Glu Leu Asn Gly Asn Lys Ala Thr Leu Val Cys Leu Ile Ser Asp
                150                 155                 160 ttc tac ccg ggt agc gtg acc gtg gtc tgg aag gca gac ggc agc acc        585
Phe Tyr Pro Gly Ser Val Thr Val Val Trp Lys Ala Asp Gly Ser Thr
        165                 170                 175 atc acc cgc aac gtg gag acc acc cgg gcc tcc aaa cag agc aac agc        633
Ile Thr Arg Asn Val Glu Thr Thr Arg Ala Ser Lys Gln Ser Asn Ser
                180                 185                 190 aag tac gcg gcc agc agc tac ctg agc ctg acg agc agc gac tgg aaa        681
Lys Tyr Ala Ala Ser Ser Tyr Leu Ser Leu Thr Ser Ser Asp Trp Lys
            195                 200                 205 tcg aaa ggc agt tac agc tgc gag gtc acg cac gag ggg agc acc gtg        729
Ser Lys Gly Ser Tyr Ser Cys Glu Val Thr His Glu Gly Ser Thr Val
210                 215                 220                 225 acg aag aca gtg aag ccc tca gag tgt tct tag ggccctggac ccccaccctc      782
Thr Lys Thr Val Lys Pro Ser Glu Cys Ser
                230                 235 gggggccctc tggcccacac ccctccccc  acctctccat ggacccctga gcccctaccc      842
aggtcgcctc acaccagggg cctctcctcc ctccctgttc ctgcttctcc tgaataaaga      902
ccttctcatt tatcaacaaa aaaaaaaaaa aaa                                   935

<210> SEQ ID NO 95
<211> LENGTH: 235
<212> TYPE: PRT
<213> ORGANISM: Bos taurus

<400> SEQUENCE: 95

Met Ala Trp Ser Pro Leu Leu Leu Thr Leu Val Ala Leu Cys Thr Gly
1               5                   10                  15

Ser Trp Ala Gln Ala Val Leu Thr Gln Pro Ser Ser Val Ser Gly Ser
            20                  25                  30

Leu Gly Gln Arg Val Ser Ile Thr Cys Ser Gly Ser Ser Thr Asn Ile
        35                  40                  45

Gly Ile Tyr Gly Val Asn Trp Tyr Gln Gln Val Pro Gly Ser Gly Leu
    50                  55                  60

Lys Thr Ile Ile Tyr Glu Asp Lys Tyr Arg Pro Ser Gly Val Pro Asp
65                  70                  75                  80

Arg Phe Ser Gly Ser Lys Ser Gly Asn Thr Ala Thr Leu Thr Ile Asn
                85                  90                  95

Ser Leu Gln Ala Glu Asp Glu Ala Asp Tyr Phe Cys Ala Ala Gly Asp
            100                 105                 110

Tyr Ser Val Asn Thr Ala Val Phe Gly Gly Gly Thr Thr Leu Thr Val
        115                 120                 125

Leu Gly Gln Pro Lys Ser Pro Pro Ser Val Thr Leu Phe Pro Pro Ser
    130                 135                 140

Thr Glu Glu Leu Asn Gly Asn Lys Ala Thr Leu Val Cys Leu Ile Ser
145                 150                 155                 160

Asp Phe Tyr Pro Gly Ser Val Thr Val Val Trp Lys Ala Asp Gly Ser
                165                 170                 175
```

```
Thr Ile Thr Arg Asn Val Glu Thr Thr Arg Ala Ser Lys Gln Ser Asn
            180                 185                 190

Ser Lys Tyr Ala Ala Ser Ser Tyr Leu Ser Leu Thr Ser Ser Asp Trp
        195                 200                 205

Lys Ser Lys Gly Ser Tyr Ser Cys Glu Val Thr His Glu Gly Ser Thr
    210                 215                 220

Val Thr Lys Thr Val Lys Pro Ser Glu Cys Ser
225                 230                 235

<210> SEQ ID NO 96
<211> LENGTH: 20
<212> TYPE: DNA
<213> ORGANISM: Artificial
<220> FEATURE:
<223> OTHER INFORMATION: T3 primer

<400> SEQUENCE: 96
aattaaccct cactaaaggg                                              20

<210> SEQ ID NO 97
<211> LENGTH: 19
<212> TYPE: DNA
<213> ORGANISM: Artificial
<220> FEATURE:
<223> OTHER INFORMATION: T7 primer

<400> SEQUENCE: 97
taatacgact cactatagg                                               19

<210> SEQ ID NO 98
<211> LENGTH: 18
<212> TYPE: DNA
<213> ORGANISM: Artificial
<220> FEATURE:
<223> OTHER INFORMATION: primer

<400> SEQUENCE: 98
ctgaccgtcc tcggtcag                                                18

<210> SEQ ID NO 99
<211> LENGTH: 18
<212> TYPE: DNA
<213> ORGANISM: Artificial
<220> FEATURE:
<223> OTHER INFORMATION: primer

<400> SEQUENCE: 99
ccttcttctc cacggtgc                                                18

<210> SEQ ID NO 100
<211> LENGTH: 18
<212> TYPE: DNA
<213> ORGANISM: Artificial
<220> FEATURE:
<223> OTHER INFORMATION: primer

<400> SEQUENCE: 100
tggtaaccca tggcctgc                                                18

<210> SEQ ID NO 101
<211> LENGTH: 18
<212> TYPE: DNA
<213> ORGANISM: Artificial
<220> FEATURE:
```

<223> OTHER INFORMATION: primer

<400> SEQUENCE: 101
accgtcttct ccacggtg                                            18

<210> SEQ ID NO 102
<211> LENGTH: 18
<212> TYPE: DNA
<213> ORGANISM: Artificial
<220> FEATURE:
<223> OTHER INFORMATION: GAPDH primer

<400> SEQUENCE: 102
gggctgcttt taactctg                                            18

<210> SEQ ID NO 103
<211> LENGTH: 18
<212> TYPE: DNA
<213> ORGANISM: Artificial
<220> FEATURE:
<223> OTHER INFORMATION: GAPDH primer

<400> SEQUENCE: 103
ccaggaaatg agcttgac                                            18

<210> SEQ ID NO 104
<211> LENGTH: 24
<212> TYPE: DNA
<213> ORGANISM: Artificial
<220> FEATURE:
<223> OTHER INFORMATION: primer

<400> SEQUENCE: 104
catatgttcg gcggaggcac ccac                                     24

<210> SEQ ID NO 105
<211> LENGTH: 24
<212> TYPE: DNA
<213> ORGANISM: Artificial
<220> FEATURE:
<223> OTHER INFORMATION: primer

<400> SEQUENCE: 105
ggtaccagag cactctgcgg gggc                                     24

<210> SEQ ID NO 106
<211> LENGTH: 23
<212> TYPE: DNA
<213> ORGANISM: Artificial
<220> FEATURE:
<223> OTHER INFORMATION: primer

<400> SEQUENCE: 106
gaattcctgc tgcgcccaac agc                                      23

<210> SEQ ID NO 107
<211> LENGTH: 24
<212> TYPE: DNA
<213> ORGANISM: Artificial
<220> FEATURE:
<223> OTHER INFORMATION: primer

<400> SEQUENCE: 107
gtcgacctat gaacattctg cagg                                     24

```
<210> SEQ ID NO 108
<211> LENGTH: 10
<212> TYPE: PRT
<213> ORGANISM: Homo sapiens

<400> SEQUENCE: 108

Leu Leu Arg Pro Thr Ala Ala Ser Gln Ser
1               5                   10

<210> SEQ ID NO 109
<211> LENGTH: 9
<212> TYPE: PRT
<213> ORGANISM: Homo sapiens

<400> SEQUENCE: 109

Ala Leu Gly Pro Gly Ala Pro Gly Gly
1               5

<210> SEQ ID NO 110
<211> LENGTH: 10
<212> TYPE: PRT
<213> ORGANISM: Homo sapiens

<400> SEQUENCE: 110

Ser Leu Arg Ser Arg Trp Gly Arg Phe Leu
1               5                   10

<210> SEQ ID NO 111
<211> LENGTH: 10
<212> TYPE: PRT
<213> ORGANISM: Homo sapiens

<400> SEQUENCE: 111

Ser Lys His Asn Ser Val Thr His Val Phe
1               5                   10

<210> SEQ ID NO 112
<211> LENGTH: 9
<212> TYPE: PRT
<213> ORGANISM: Homo sapiens

<400> SEQUENCE: 112

Lys His Asn Ser Val Thr His Val Phe
1               5

<210> SEQ ID NO 113
<211> LENGTH: 10
<212> TYPE: PRT
<213> ORGANISM: Homo sapiens

<400> SEQUENCE: 113

Ser Val Thr His Val Phe Gly Ser Gly Thr
1               5                   10

<210> SEQ ID NO 114
<211> LENGTH: 9
<212> TYPE: PRT
<213> ORGANISM: Homo sapiens

<400> SEQUENCE: 114

Val Thr His Val Phe Gly Ser Gly Thr
1               5

<210> SEQ ID NO 115
<211> LENGTH: 9
```

```
<212> TYPE: PRT
<213> ORGANISM: Homo sapiens

<400> SEQUENCE: 115

Val Phe Gly Ser Gly Thr Gln Leu Thr
1               5

<210> SEQ ID NO 116
<211> LENGTH: 9
<212> TYPE: PRT
<213> ORGANISM: Homo sapiens

<400> SEQUENCE: 116

Gly Ser Gly Thr Gln Leu Thr Val Leu
1               5

<210> SEQ ID NO 117
<211> LENGTH: 10
<212> TYPE: PRT
<213> ORGANISM: Homo sapiens

<400> SEQUENCE: 117

Gln Leu Thr Val Ile Ser Gln Pro Lys Ala
1               5                   10

<210> SEQ ID NO 118
<211> LENGTH: 9
<212> TYPE: PRT
<213> ORGANISM: Homo sapiens

<400> SEQUENCE: 118

Ala Tyr Met Arg Glu His Asn Gln Leu
1               5
```